US010919938B2

(12) United States Patent
Wester et al.

(10) Patent No.: US 10,919,938 B2
(45) Date of Patent: Feb. 16, 2021

(54) MODIFIED CYCLOPENTAPEPTIDES AND USES THEREOF

(71) Applicant: TECHNISCHE UNIVERSITÄT MÜNCHEN, Munich (DE)

(72) Inventors: Hans-Jürgen Wester, Immünster (DE); Margret Schottelius, Munich (DE); Theresa Osl, Munich (DE); Andreas Poschenrieder, Munich (DE); Marina Willibald, Weßling (DE)

(73) Assignee: TECHNISCHE UNIVERSITÄT MÜNCHEN, München (DE)

( * ) Notice: Subject to any disclaimer, the term of this patent is extended or adjusted under 35 U.S.C. 154(b) by 90 days.

(21) Appl. No.: 15/315,290

(22) PCT Filed: Jun. 6, 2014

(86) PCT No.: PCT/EP2014/061875
§ 371 (c)(1),
(2) Date: Nov. 30, 2016

(87) PCT Pub. No.: WO2015/185162
PCT Pub. Date: Dec. 10, 2015

(65) Prior Publication Data
US 2018/0037608 A1    Feb. 8, 2018

(51) Int. Cl.
*A61K 51/08* (2006.01)
*C07K 7/64* (2006.01)

(52) U.S. Cl.
CPC .............. *C07K 7/64* (2013.01); *A61K 51/08* (2013.01); *A61K 51/082* (2013.01)

(58) Field of Classification Search
CPC ...... A61K 51/00; A61K 51/08; A61K 51/082; A61K 38/00; A61K 2123/00; A61K 2121/00; A61K 49/00; A61K 38/03; A61K 38/04; C07K 7/64
USPC ........ 424/1.11, 1.65, 1.69, 9.1, 9.2, 9.3, 9.4, 424/9.5, 9.6; 514/1, 1.1, 19.2, 21.1, 21.8; 530/300, 317, 330; 534/7, 10–34
See application file for complete search history.

(56) References Cited

U.S. PATENT DOCUMENTS

| 7,038,078 | B2  |  5/2006 | Aldrich et al. |
| 7,589,061 | B2* |  9/2009 | Wester ................. A61K 51/083 514/1.1 |
| 8,575,100 | B2* | 11/2013 | Wester ................. A61K 51/088 514/11.1 |
| 8,628,750 | B2* |  1/2014 | Wester ................. A61K 51/088 424/1.11 |
| 9,266,924 | B2* |  2/2016 | Demmer ................. C07K 7/64 |

FOREIGN PATENT DOCUMENTS

| WO | WO 89/07456 A1 | 8/1989 | |
| WO | WO 97/31657 A2 | 9/1997 | |
| WO | WO 2006/017619 A2 | 2/2006 | |
| WO | WO 2007/096662 A2 | 8/2007 | |
| WO | WO 2008/008854 A2 | 1/2008 | |
| WO | WO 2009/027706 A2 | 3/2009 | |
| WO | WO 2009/109332 A1 | 9/2009 | |
| WO | WO 2009/134382 A2 | 11/2009 | |
| WO | WO 2011/131731 A1 | 10/2011 | |
| WO | WO 2011/131735 A1 | 10/2011 | |
| WO | WO-2011131735 A1 * | 10/2011 | ........... A61K 51/088 |

OTHER PUBLICATIONS

Burger-Kentischer et al., "Expression of Macrophage Migration Inhibitory Factor in Different Stages of Human Atherosclerosis", Circulation, vol. 105, Apr. 2, 2002, pp. 1561-1566.
Darpan et al., "A New Synthesis for TE2A-a Potential Bifunctional Chelator for $^{64}Cu$", Nuclear Medicine and Molecular Imaging, vol. 44, No. 3, 2010, pp. 185-192.
Demmer et al., "Introduction of Functional Groups into Peptides via N-Alkylation", Organic Letters, vol. 10, No. 10, 2008, pp. 2015-2018.
Fujii et al., "Molecular-Size Reduction of a Potent CXCR4-Chemokine Antagonist Using Orthogonal Combination of Conformation- and Sequence-Based Libraries", Angewandte Chemie-International Edition, vol. 42, 2003, pp. 3251-3253.
Hansson et al., "Inflammation, Atherosclerosis, and Coronary Artery Disease", The New England Journal of Medicine, vol. 352, No. 16, 2005, pp. 1685-1695.
International Search Report issued in PCT/EP2014/061875, dated Jan. 5, 2015.
Kim et al., "Chemokine Receptor CXCR4 Expression in Colorectal Cancer Patients Increases the Risk for Recurrence and for Poor Survival", Journal of Clinical Oncology, vol. 23, No. 12, Apr. 20, 2005, pp. 2744-2753.
Kuehl et al., "Can PET/CT Replace Separate Diagnostic CT for Cancer Imaging? Optimizing CT Protocols for Imaging Cancers of the Chest and Abdomen", J. Nucl. Med., vol. 48, 2007, pp. 45S-57S.

(Continued)

*Primary Examiner* — D. L. Jones
(74) *Attorney, Agent, or Firm* — Birch, Stewart, Kolasch & Birch, LLP

(57) ABSTRACT

The present invention, among others, relates to a compound having a structure according to formula (I) or a pharmaceutically acceptable salt thereof, wherein $Xaa^1$ are the iodo-substituted or methyl-substituted amino acids D- and L-Tyr, iodo-substituted or methyl-substituted D- and L-homotyrosine, iodo-substituted or methyl-substituted D- and L-Phe, iodo-substituted or methyl-substituted D- and L-p-OH-phenylglycine, and iodo-substituted or methyl-substituted D- or L-Trp, $Xaa^2$ to $Xaa^4$ are independently of each other, an optionally N-alkylated natural or unnatural amino acid, R is H or methyl, L is a linker moiety, Ar is a spacer comprising an aromatic moiety, and D comprises, preferably is i) a combination of an organic complexation agent and a radioactive or a detectable label; or ii) a radioactive or a detectable label, an organic complexation agent or an active substance, said active substance particularly being selected from cytotoxic agents, lipids, sugars, sugar conjugates, sugar derivatives, proteins and combinations thereof.

11 Claims, 5 Drawing Sheets

(56) References Cited

OTHER PUBLICATIONS

Levesque et al., "Mobilization of hematopoietic stem cells: state of the art", Current Opinion in Organ Transplantation, vol. 13, 2008, pp. 53-58.
Libby, "Inflammation in atherosclerosis", Nature, vol. 420, Dec. 2002, pp. 868-874.
Mizukami et al., Paramagnetic Relaxation-Based $^{19}$F MRI Probe to Detect Protease Activity, Journal of the American Chemical Society, vol. 130, No. 3, 2008, pp. 794-795.
Phillips et al., "The Stromal Derived Factor-1/CXCL12-CXC Chemokine Receptor 4 Biological Axis in Non-Small Cell Lung Cancer Metastases", American Journal of Respiratory and Critical Care Medicine, vol. 167, 2003, pp. 1676-1686.
Ross, "The pathogenesis of atherosclerosis: a perspective for the 1990s", Nature, vol. 362, Apr. 29, 1993, pp. 801-809.
Schober et al., "Chemokine-like functions of MIF in atherosclerosis", J. Mol. Med., vol. 86, 2008, pp. 761-770.
Shah et al., "Molecular Optical Imaging: Applications Leading to the Development of Present Day Therapeutics", NeuroRx: The Journal of the American Society for Experimental NeuroTherapeutics, vol. 2, Apr. 2005, pp. 215-225.
Taniuchi et al., "The role of a mutation of the CXCR4 gene in WHIM syndrome", Haematologica, vol. 90, No. 9, 2005, pp. 1271-1272.
Van der Plas et al., "Synthesis of a Tripodal Scaffold for Solid Phase Synthesis of Artificial Receptors", European Journal of Organic Chemistry, 2008, pp. 1582-1588.
Weissleder et al., "Imaging in the era of molecular oncology", Nature, vol. 452, Apr. 3, 2008, pp. 580-589.
Weissleder et al., "Shedding light onto live molecular targets", Nature Medicine, vol. 9, No. 1, Jan. 2003, pp. 123-128.
Written Opinion of the International Searching Authority issued in PCT/EP2014/061875 (PCT/ISA/237), dated Jan. 5, 2015.
Yang et al., "Solid-Phase Synthesis of Azidomethylene Inhibitors Targeting Cysteine Proteases", Organic Letters, vol. 10, No. 10, 2008, pp. 1881-1884.
Zhang et al., "Iron(III) Complexes as Superoxide Dismutase Mimics: Synthesis, Characterization, Crystal Structure, and Superoxide Dismutase (SOD) Activity of Iron(III) Complexes Containing Pentaaza Macrocyclic Ligands", Inorganic Chemistry, vol. 37, No. 5, 1998, pp. 956-963.

\* cited by examiner

MODIFIED CYCLOPENTAPEPTIDES AND USES THEREOF

The present invention is, among others, concerned with derivatized cyclopeptides, with processes for their preparation, pharmaceutical compositions comprising same and various embodiments relating to the application of said derivatives including imaging and medical applications. Specifically, the present invention relates to a compound having a structure according to general formula (I)

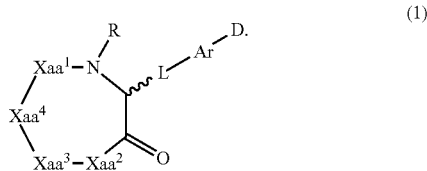

(1)

The compounds of the invention are believed to be capable of binding to the seven trans-membrane G-protein coupled chemokine receptor CXCR4 with high affinity and are thus considered CXCR4 ligands. They preferably act as antagonists, or may also act as agonists or inverse agonists.

The interaction between CXCR4 and its natural ligand α-chemokine stromal-derived factor (SDF-1α/CXCL12) is a key factor in diverse bodily functions. Starting at the beginning of life with normal stem cell trafficking during embryogenesis it is also responsible for normal cardiovascular, hematopoietic and brain development as well as functions in the nervous and immune system.

The CXCR4 receptor has been found to be involved in a variety of diseases. For example, it mediates HIV-1 entry into T-cells as a co-receptor where it was first identified. Further-more, in rheumatoid arthritis (RA) CXCR4 expressing $CD4^+$ memory T cells accumulate in the inflamed synovium because of the high local CXCL12 concentration. Additionally CXCR4 is overexpressed on numerous different tumor cell types ranging from melanoma over prostate and pancreatic cancer to brain tumor cells.

Coronary heart disease has become a leading cause of death worldwide. The pathologic basis for coronary heart disease (CHD) is the growth of atherosclerotic plaques in the vascular wall over a period of many years resulting in bloss-flow-limiting stenosis or plaques disruption with acute thrombotic occlusion (Ross, 1993; Libby, 2002; Hansson 2005). Substantial evidence supports the concept that chronic inflammation of the vessel wall characterized by the influx of circulating immune cells is responsible for the development of atherosclerotic lesions (Schober et al., 2008).

In the pathogenesis of atherosclerosis, chronic inflammation of the arterial wall characterized by chemokine-mediated influx of leukocytes plays a central role. The cytokine macrophage migration inhibitory factor (MIF) is a unique pro-inflammatory regulator of many acute and chronic inflammatory diseases that contribute to lesion progression and plaque inflammation. These chemokine-like functions are mediated through interaction of MIF with the chemokine receptors CXCR2 and CXCR4, thus demonstrating the role of CXCR4 in native atherosclerosis, plaque destabilization and aneurysm formation.

Via binding of MIF, CXCR4 and other chemokine receptors, like CXCR2 play a role in atherosclerotic plaque development, vascular remodeling after injury, in atherosclerosis plaque destabilization and aneurysm formation (Schober et al., 2008).

Like chemokines, the interaction of MIF with the chemokine receptors CXCR2 and CXCR4 as a noncanonical ligand induces recruitment of monocytes and T cells to atherosclerotic lesions, Furthermore, MIF regulates smooth muscle cell migration and proliferation, which may promote lesion growth. Increased foam-cell transformation of lesional macrophages and enhanced degradation of extracellular matrix proteins by MIF contribute to the progression into an unstable plaque phenotype. These data were largely confirmed in a study using human specimens from patients undergoing heart transplantation, carotis endarterectomy, or from autopsied individuals (Burger-Kentischer et al, 2002).

Accordingly, due to their potential use for medicinal applications, a variety of peptidic and non-peptidic CXCR4 antagonists have been developed. One example is the bicyclam AMD3100 (plerixafor)

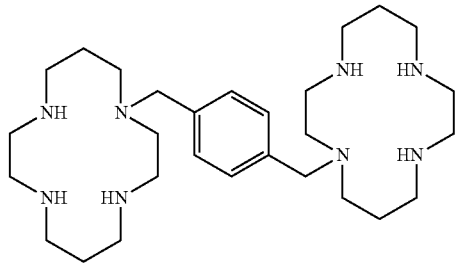 [SMILES: c1cc(CN2CCCNCCNCCCNCC2)ccc1CN1CCCNCCNCCCNCC1]

that has been approved by the FDA and the EMEA for the treatment of the two blood cancer types non-Hodgkin's lymphoma and multiple myeloma. Based on the structure of AMD3100 further CXCR4 antagonists such as peptidic CXCR4 antagonists have been developed. Examples include T140 and its derivatives which are side-chain cyclized peptides that contain one or two cyclization sites. Further downsizing of T140 gave the head-to-tail cyclized pentapeptide FC131 with good antagonistic activity (Fujii et al., 2003). A potential advantage of CXCR4 antagonists derived from T140, like FC131, may be their suggested mechanism of action as inverse agonists in contrast to agents like AMD3100 which are partial agonists. Furthermore, a number of modifications of FC131 have been described (WO 2007/096662). Besides, certain multimeric and in particular dimeric compounds of such cyclized pentapeptides have been described, wherein a spacer moiety between the monomeric ligands is selected such that the ligands are spaced apart to avoid an interference between both ligands. (WO 2009/027706).

Barry et al. describes cyclic RGD peptides labeled with a DOTA as chelator coupled via a non aromatic spacer moiety, wherein the spacer moiety is attached to the cyclic RGD peptide with a (—$CH_2$)$_4$NH-group (Barry et al, 2009).

Also known are radiolabeld cyclic polypeptides, which use non-aromatic heterocycles as spacer moiety (WO 2009/134382).

So far, therapeutic potential of CXCR4 ligands, such as antagonists, has been shown e.g. for the treatment of HIV infection, cancer, and rheumatoid arthritis. Other anti-inflammatory uses of CXCR4 ligands have been described for asthma and multiple sclerosis. Furthermore, CXCR4 ligands can mobilize stem cells, e.g. for stem cell transplantations. Moreover, attenuation of pain has been observed (in rodents)

by a specific CXCR4 ligand. In addition CXCR4 ligands are also discussed for the treatment of neurological diseases.

CXCR4 ligands comprising additional moieties may be particularly suitable in the treatment of the above diseases. Examples for the latter ligands include but are not limited to those comprising cytotoxic, (oligo)nucleotide, radioactive, and (radio)metal-chelate moieties or combinations thereof. The general concepts pursued with such moieties are known from certain other peptidic and peptidomimetic ligands.

In addition to the therapeutic potential of CXCR4 ligands, their affinity towards the receptor may be used for other applications. These include but are not limited to the imaging of CXCR4 receptors, e.g. for the diagnosis of related diseases or the visualization of CXCR4 and CXCR4 containing tissue, as well as affinity purification of CXCR4 receptors. In most of these cases, the CXCR4 ligands are modified with additional (functional) moieties and/or moieties that immobilize the CXCR4 ligands.

However, the attachment of such additional moieties to the CXCR4 ligands may result in that the ligands substantially loose their affinity to the CXCR4 receptor. Therefore, there is a need in the art to develop new CXCR4 ligands, particularly ligands having high affinity to CXCR4, more particularly such ligands that allow the introduction of additional (functional) moieties while retaining sufficient affinity to the CXCR4 receptor.

The present invention provides such new CXCR4 ligands and their uses in medicinal and scientific applications as well as such ligands comprising additional (functional) moieties and their uses in medicinal and scientific applications.

The compounds of the invention are considered capable of binding with high affinity to CXCR4 and, hence, are considered CXCR4 ligands. They may be capable of functioning as CXCR4 antagonists, agonists or inverse agonists. Surprisingly, compounds of the invention are shown herein to have high affinity to the CXCR4 receptor despite the attachment of linkers and additional moieties such as a radiometal isotope, independently whether a radioisotope with imaging (gamma- or positron emission) or therapeutic (beta" or alpha emission) properties is used. As shown herein, surprisingly, compounds of the invention are considered particularly suitable for medical applications such as imaging and therapeutic applications, such as endoradiotherapy.

The present invention provides compounds, compositions, uses and methods as defined in the claims. In one aspect, the present invention thus provides a compound, or a pharmaceutically acceptable salt thereof, having a structure according to formula I

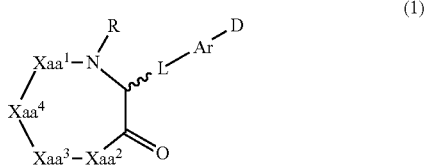

or a pharmaceutically acceptable salt thereof, wherein $Xaa^1$ refers to the iodo-substituted or methyl-substituted amino acids D- and L-Tyr, iodo-substituted or methyl-substituted D- and and L-homotyrosine, iodo-substituted or methyl-substituted D- and L-Phe, iodo-substitued or methyl-substituted D- and L-p-OH-phenylglycine, and iodo-substituted or methyl-substituted D- or L-Trp. $Xaa^2$ to $Xaa^4$ are independently of each other, an optionally N-alkylated natural or unnatural amino acid, R is H or methyl, L is a linker moiety, Ar is a spacer comprising an aromatic or aliphatic moiety, and D comprises, preferably is i) a combination of an organic complexation agent and a radioactive or non-radioactive metal ion or $Al^{18}F^{2+}$;
Or
ii) a radioactive or non-radioactive metal ion or $Al^{18}F^{2+}$, an organic complexation agent or an active substance, said active substance particularly being selected from cytotoxic agents, lipids, sugars, sugar conjugates, sugar derivatives, proteins and combinations thereof.

In the compounds of the invention having a structure according to formula I the carbonyl carbon atom of $Xaa^2$ is linked to the $N^{alpha}$ atom of $Xaa^3$, the carbonyl carbon atom of $Xaa^3$ is linked to the $N^{alpha}$ atom of $Xaa^4$, and the carbonyl carbon atom of $Xaa^4$ is linked to the $N^{alpha}$ atom of $Xaa^1$.

Furthermore, the present invention relates to methods for preparing the above mentioned compound. The invention also relates to compositions, methods and uses related to said compounds.

DETAILED DESCRIPTION OF THE INVENTION

Figure 1:
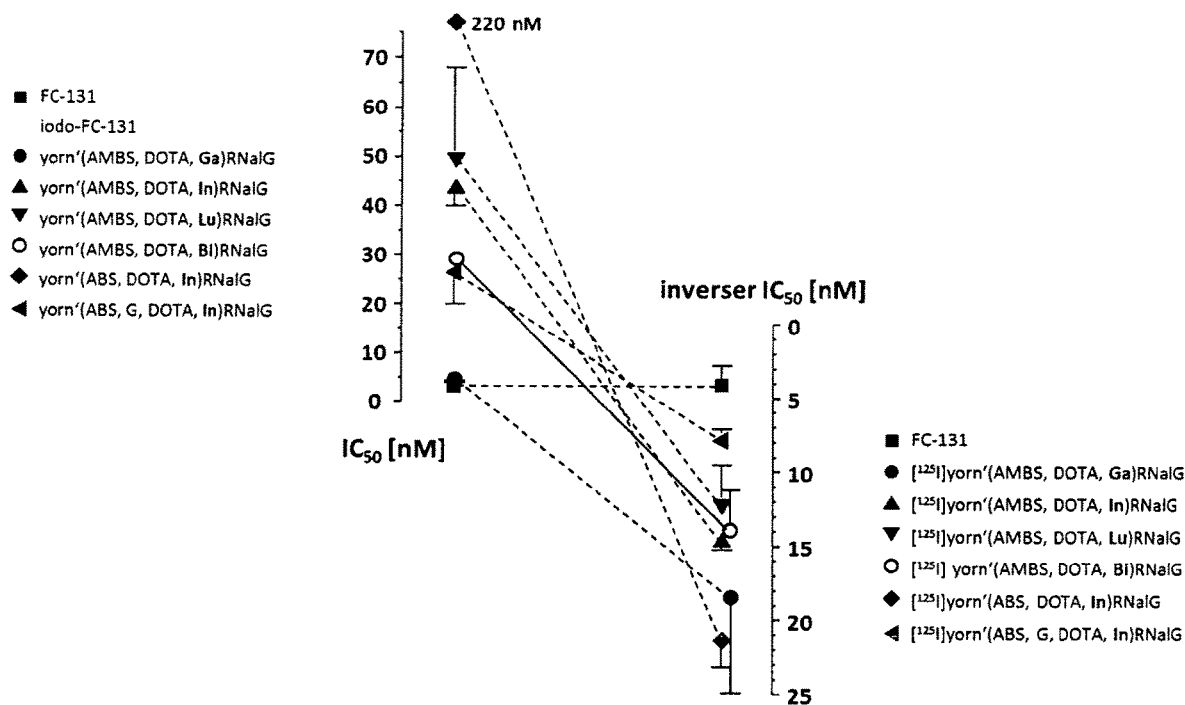
FIG. 1: Correlation of $IC_{50}$ and inverse $IC_{50}$ (higher $IC_{50,inv}$ values indicate an increased hCXCR4-affinity) of different radioiodinated CXCR4-ligands to hCXCR4-expressing Jurkat T-cell leukemia cells.

The present invention provides compounds, compositions, uses and methods as defined and described in the items and hereinbelow.

1. A compound having a structure according to formula I

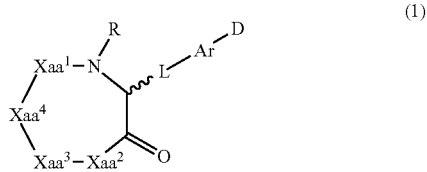

or a pharmaceutically acceptable salt thereof, wherein Xaa¹ is selected from the group consisting of iodo-substituted or methyl-substituted amino acids D- and L-Tyr, iodo-substituted or methyl-substituted D- and L-homotyrosine, iodo-substituted or methyl-substituted D- and L-Phe, iodo-substituted or methyl-substituted D- and L- p-OH-phenylglycine, and iodo-substituted or methyl-substituted D- or L- Trp;

Xaa² to Xaa⁴ are independently of each other, an optionally N-alkylated natural or unnatural amino acid, R is H or methyl, L is a linker moiety Ar is a spacer comprising an aromatic moiety and D comprises, preferably is i) a combination of an organic complexation agent and a radioactive or detectable label; or ii) a radioactive or detectable label, an organic complexation agent or an active substance, said active substance particularly being selected from cytotoxic agents, lipids, sugars, sugar conjugates, sugar derivatives, proteins and combinations thereof.

In one aspect of the invention, in particular in any of item 1 (above) and items 2-20 (below), the compound is as defined herein (formula I), but is not (3$^{125}$iodo-y)-orn' (AMBS, DOTA, $^{68}$Ga)RNalG, i.e. is not iodinated[$^{68}$Ga] pentixafor. In one aspect of the invention, in particular in any of item 1 (above) and items 2-20 (below), the compound is as defined herein (formula I), but is not (iodo-y)-orn' (AMBS, DO-TA, $^{68}$Ga)RNalG, is not ($^{125}$iodo-y)-or-tAAMBS, DOTA, $^{68}$Ga)RNalG and is not ($^{131}$iodoy)-orn' (AMBS, DOTA, $^{68}$Ga)RNalG. In one aspect of the invention, in particular in any of item 1 (above) and items 2-20 (below), the compound is as defined herein (formula I), but is not (3-$^{125}$iodo-y)-orni(AMBS, DOTA, $^{68}$Ga)RNalG, or (3$^{131}$iodo-y)-orn'(AMBS, DOTA, $^{68}$Ga)RNalG.

2. The compound of item 1, wherein Xaa² and Xaa³ are, independently of each other, an optionally N-methylated amino acid comprising an aromatic moiety in its side chain.

3. The compound of item 1 or 2, wherein Xaa³ are, independently of each other, selected from the group phenylalanine, D-phenylalanine, tyrosine, D-tyrosine, tryptophan, D-tryptophan, D-phenylglycine, phenylglycine, naphthylalanine (Nal) and D-naphthylalanine (D-Nal), preferably wherein Xaa³ is tryptophan or naphthylalanine.

4. The compound of any of items 1 to 3, wherein Xaa² is a natural or unnatural basic amino acid, preferably wherein Xaa² is arginine.

5. The compound of any of items 1 to 4, wherein Xaa⁴ is glycine or a D-amino acid, preferably wherein Xaa⁴ is glycine.

6. The compound of any of items 1 to 5, wherein i) L comprises the group —(CH$_2$)$_n$— with n being from 1 to 10; and/or ii) wherein L comprises a functional group being an amino group —NH$_2$ or a derivative of an amino groups comprising the structure unit —NH—; and/or iii) wherein L is selected from the following structures:

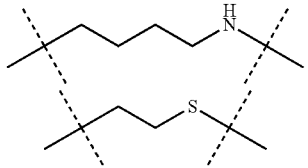

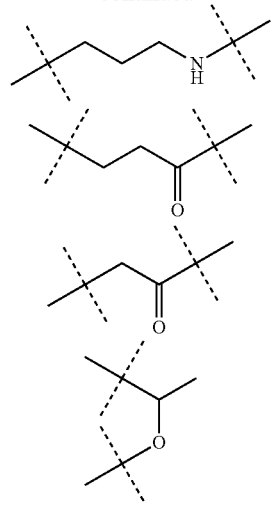

7. The compound of any of items 1 to 6, wherein Ar comprises a phenyl group; and/or wherein Ar further comprises a spacer moiety linking the optionally substituted aryl or heteroaryl moiety to D, said spacer moiety optionally comprising a bifunctional linker;

especially wherein Ar is a group having the formula:

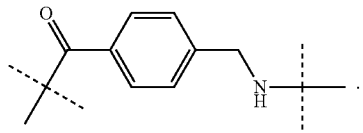

8. The compound of any of items 1 to 7, wherein D comprises, preferably is i) an organic complexation agent selected from the group consisting of NODASA, NODAGA, TETA, TRITA, TRAP, DTPA, CHX-DTPA EDTA, CDTA, CPTA, DOTP, DOTPI, EGTA, HBED, TTHA, DTPA, DOTA, DOTAGA, NOTA, HP-DOA3, CBTE2a, TE2A, TMT, DPDP, HYNIC, DFO, HEDTA, NOPO. MAG3, NCS-MP-NODA, NH2-MPAA-NODA, and particularly from DOTA, DOTAGA, NOTA, DTPA, CHX-DTPA, NODA and functionalized NODA, TRAP, DOTPI, DOTP, NOPO and TETA; and/or ii) a radionuclide selected from the group consisting of $^{11}$C, $^{18}$F, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{72}$As, $^{77}$As, $^{75}$Br, $^{76}$Br, $^{77}$Br, $^{82}$Br, $^{89}$Zr, $^{90}$Y, $^{94m}$Tc, $^{99m}$Tc, $^{97}$Ru, $^{105}$Rh, $^{109}$Pd, $^{111}$Ag, $^{110m}$In, $^{111}$In, $^{113}$In, $^{114m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}_{Re}$, $^{191}$Pt, $^{197}$Hg, $^{198}$Au, $^{199}$Au, $^{201}$Tl, $^{203}$Pb, $^{211}$At, $^{212}$Bi and $^{225}$Ac and the radioactive ion Al$^{18}$F$^{2+}$; particularly from the group consisting of $^{18}$F, $^{68}$Ga, $^{67}$Ga, $^{64}$Cu, $^{89}$Zr, $^{90}$Y, $^{99m}$Tc, $^{111}$In, $^{123}$I, $^{124}$I, $^{131}$I, $^{177}$Lu and the radioactive ion Al$^{18}$F$^{2+}$; especially from the group consisting of $^{64}$Cu, $^{67}$Ga, $^{68}$Ga, $^{99m}$Tc, $^{111}$In, $^{123}$I, $^{131}$I, $^{90}$Y, $^{177}$Lu, $^{212}$Bi, $^{225}$Ac and the radioactive ion Al$^{18}$F$^{2+}$; and/or iii) a combination of a radionuclide and a complexation agent, with the complexation agent being covalently bound to Ar, especially wherein the radionuclide is a Lu radionuclide, an Y-radionuclide, an In radionuclide, an Ga radionuclide, a Bi radionuclide, a Cu radionuclide, an Zr radionuclide, a Tc radionuclide, a Tb radionuclide, a Ho radionuclide or an $Al^{18}F^{2+}$ ion, particularly wherein the following combinations are selected: Ga with DOTA, NODASA, NODAGA, DOTAGA, NOTA, NOPO, TRAP and in particular Ga with DOTA, NOPO, TRAP, NODAGA, DOTAGA and NOPO, Lu with DOTA, DOTPI, DOTAGA, DTPA and CHX-DTPA and in particular Lu with DOTA, DOTPI, DOTAGA, Y with DOTA, DOTPI, DOTAGA, DTPA and CHX-DTPA and in particular Y with DOTA, DOTPI, DOTAGA, In with DOTA, DOTPI, DOTAGA, DTPA and CHX-DTPA and in particular In with DOTA, DTPA, DOTPI, DOTAGA, Bi with DOTA, DOTPI, DOTP, DOTAGA, DTPA and CHX-DTPA and in particular Bi with DOTA, DOTPI, DOTP, DOTAGA, Cu with NOTA, TRAP, NOPO, DOTPI and NODAGA and in particular Cu with NOTA, TRAP, NOPO, DOTPI, Zr with DFO, Tc with DTPA, HYNIC and $MAG_3$, Tb with DOTA, DOTPI, DOTAGA, DTPA and CHX-DTPA and in particular Tb with DOTA, DOTPI, DOTAGA, Ho with DOTA, DOTPI, DOTAGA, DTPA and CHX-DTPA and in particular Ho with DOTA, DOTPI, DOTAGA, wherein particularly preferred combinations are selected from $Al^{18}F^{2+}$ with functionalized NODA, such as NH2-MPAA-NODA or NCS-MP-NODA, or NODAGA, DOTA or CHX-DTPA, and in particular $Al^{18}F^{2+}$ with functionalized NODA, NODAGA, DOTA or CHX-DTPA.

9. The compound of any of items 1 to 8,
i) having the structure:

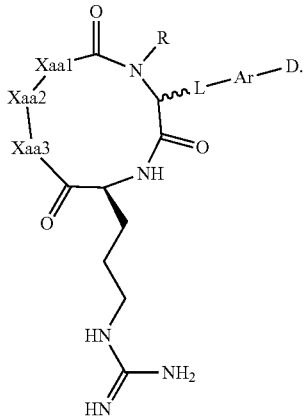

10. The compound of item 1, wherein
$Xaa^1$ is an iodo-substituted D- or L-tyrosine amino acid or an iodo-substituted D- or L-homotyrosine amino acid;
$Xaa^2$ is arginine;
$Xaa^3$ is naphthylalanine;
$Xaa^4$ is glycine;
L is a linker moiety selected from the following structures:

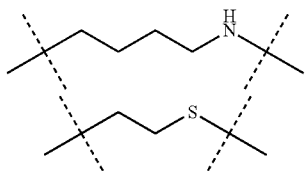

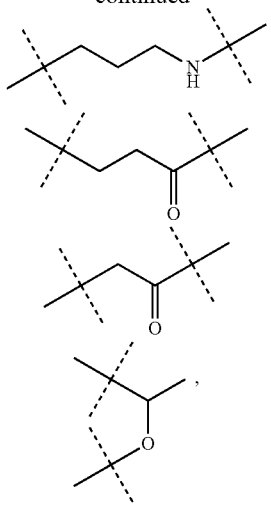

preferably L is:

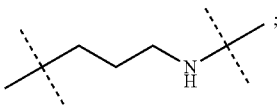

Ar is

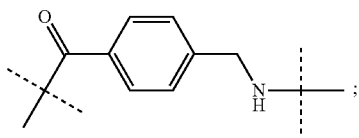

wherein D is a combination of a radionuclide and a complexation agent, with the complexation agent being covalently bound to Ar, wherein
i) the complexation agent is selected from the group consisting of NODASA, NODAGA, TETA, TRITA, TRAP, DTPA, CHX-DTPA EDTA, CDTA, CPTA, DOTP, DOTPI, EG-TA, HBED, TTHA, DTPA, DOTA, DOTAGA, NOTA, HP-DOA3, CBTE2a, TE2A, TMT, DPDP, HYNIC, DFO, HEDTA, NOPO. MAG3, NCS-MP-NODA, NH2-MPAA-NODA, and particularly from DOTA, DOTAGA, NOTA, DTPA, CHX-DTPA, NODA and functionalized NODA, TRAP, DOTPI, DOTP, NOPO and TETA, particularly selected from DOTA, NOTA, DTPA, and TETA, more preferably DOTA; most preferably DOTA when L is:

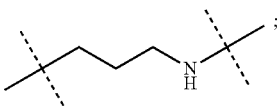

and
ii) the radionuclide is selected from the group of radionuclides comprising the diagnostic and therapeutic radionuclides and therapeutic radionuclides $^{11}C$, $^{18}F$, $^{47}Sc$, $^{51}Cr$, $^{52m}Mn$, $^{58}Co$, $^{52}Fe$, $^{56}Ni$, $^{57}Ni$, $^{62}Cu$, $^{64}Cu$, $^{67}CU$, $^{66}Ga$, $^{68}Ga$, $^{67}Ga$, $^{72}As$, $^{77}As$, $^{75}Br$, $^{76}Br$, $^{77}Br$, $^{82}Br$, $^{89}Zr$, $^{90}Y$, $^{94m}$Tc, $^{99}$Tc, $^{97}$Ru, $^{105}$Rh, $^{109}$Pd, $^{111}$Ag, $^{110m}$In, $^{111}$In, $^{113m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $_{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $_{-188}$Re, $^{191}$Pt, $^{197}$Hg, $^{198}$Au, $^{199}$Au, $^{201}$Tl, $^{203}$Pb, $^{211}$At, $_{212}$Bi and $^{225}$Ac and the radioactive ion $Al^{18}F^{2+}$; particularly from the group consisting of $^{18}$F, $^{68}$Ga, $^{67}$Ga, 64Cu, $_{89}$Zr, $^{90}$Y, $^{99m}$Tc, $^{111}$In, $^{123}$I, $^{124}$I, $^{131}$I, $_{177}$Lu and the radioactive ion $Al^{18}F^{2+}$; especially from the group consisting of $^{64}$Cu, $^{67}$Ga, $^{68}$Ga, $^{99m}$Tc, $^{111}$In, $^{123}$I, $^{131}$I, $^{90}$Y, $^{177}$Lu, $^{212}$Bi, $^{225}$Ac and the radioactive ion $Al^{18}F^{2+}$, wherein preferred combinations of radionuclides and complexation agents are defined in item 8, preferably the radionuclides are therapeutic radionuclides.

11. The compound of item 10, wherein $Xaa^1$ is the 3-iodinated D- or L-tyrosine amino acid or the 3-iodinated D- or L-homotyrosine amino acid, preferably is 3-iodinated tyrosine;

$Xaa^2$ is arginine;

$Xaa^3$ is naphthylalanine;

$Xaa^4$ is glycine;

L is a linker moiety selected from the following structures:

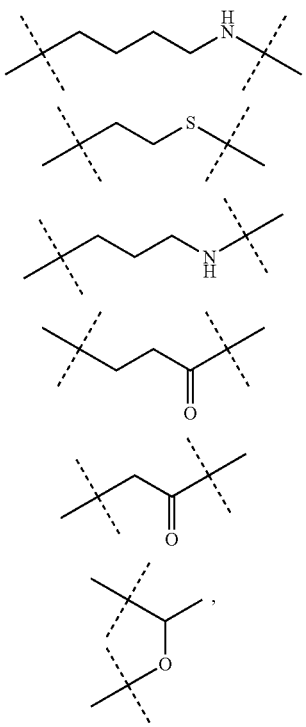

preferably L is:

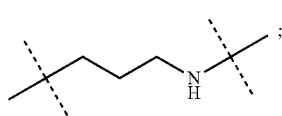

Ar is

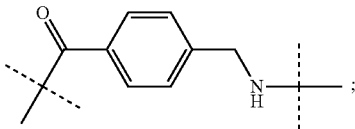

wherein D is a combination of a radionuclide and a complexation agent, with the complexation agent being covalently bound to Ar, wherein i) the complexation agent is selected from the group consisting of NODASA, NODAGA, TETA, TRITA, TRAP, DTPA, CHX-DTPA EDTA, CDTA, CPTA, DOTP, DOTPI, EG-TA, HBED, TTHA, DTPA, DOTA, DOTAGA, NOTA, HP-DOA3, CBTE2a, TE2A, TMT, DPDP, HYNIC, DFO, HEDTA, NOPO. MAG3, NCS-MP-NODA, NH2-MPAA-NODA, and particularly from DOTA, DOTAGA, NOTA, DTPA, CHX-DTPA, NODA and functionalized NODA, TRAP, DOTPI, DOTP, NOPO and TETA; and ii) the radionuclide is selected from the group consisting of the diagnostic and therapeutic radionuclides $^{11}$C, $^{18}$F, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{72}$As, $^{77}$As, $^{75}$Br, $^{76}$Br, 77Br, $^{82}$Br, $^{89}$Zr, $^{90}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi and $^{225}$Ac and the radioactive ion $Al^{18}F^{2+}$; particularly from the group consisting of $^{18}$F, $^{68}$Ga, $^{67}$Ga, $^{64}$Cu, $^{89}$Zr, $^{90}$Y, $^{99m}$Tc, $^{111}$In, $^{123}$I, $^{124}$I, $^{131}$I, $^{177}$Lu and the radioactive ion $Al^{18}F^{2+}$; especially from the group consisting of $^{64}$Cu, $^{67}$Ga, $^{68}$Ga, $^{99m}$Tc, $^{111}$In, $^{123}$I, $^{131}$I, $^{90}$Y, $^{177}$Lu, $^{212}$Bi, $^{225}$Ac and the radioactive ion $Al^{18}F^{2+}$, wherein preferred combinations of radionuclides and complexation agents are defined in item 8, preferably the radionuclides are therapeutic radionuclides.

12. The compound of item 10 or 11, wherein $Xaa^1$ is an iodo-substituted D- or L-tyrosine amino acid or an iodo-substituted D- or L-homotyrosine amino acid, wherein the tryrosine or homotyrosine, preferably tyrosine, is substituted with $^{127}$I, most preferably is 3-iodinated with $^{127}$I;

$Xaa^2$ is arginine;

$Xaa^3$ is naphthylalanine;

$Xaa^4$ is glycine;

L is a linker moiety selected from the following structures:

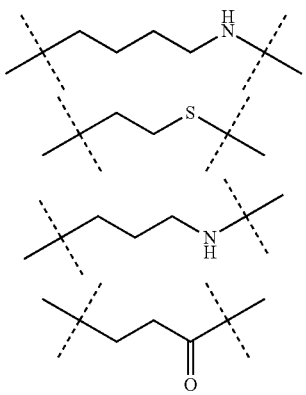

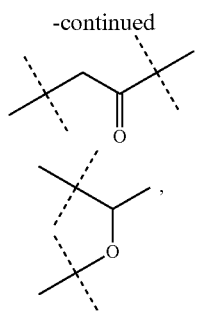

preferably L is:

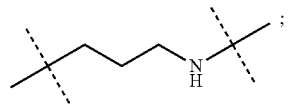

Ar is

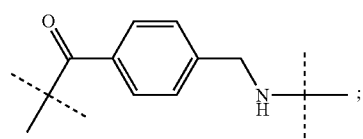

wherein D is a combination of a radionuclide and a complexation agent, with the complexation agent being covalently bound to Ar, wherein
i) the complexation agent is selected from the group consisting of NODASA, NODAGA, TETA, TRITA, TRAP, DTPA, CHX-DTPA EDTA, CDTA, CPTA, DOTP, DOTPI, EG-TA, HBED, TTHA, DTPA, DOTA, DOTAGA, NOTA, HP-DOA3, CBTE2a, TE2A, TMT, DPDP, HYNIC, DFO, HEDTA, NOPO. MAG3, NCS-MP-NODA, NH2-MPAA-NODA, and particularly from DOTA, DOTAGA, NOTA, DTPA, CHX-DTPA, NODA and functionalized NODA, TRAP, DOTPI, DOTP, NOPO and TETA, particularly selected from DOTA, NOTA, DTPA, and TETA, most preferably DOTA; and
ii) the radionuclide is selected from the group consisting of the diagnostic and therapeutic radionuclides $^{11}C$, $^{18}F$, $^{47}Sc$, $^{51}Cr$, $^{52m}Mn$, $^{58}Co$, $^{52}Fe$, $^{56}Ni$, $^{57}Ni$, $^{62}Cu$, $^{64}Cu$, $^{67}Cu$, $^{66}Ga$, $^{68}Ga$, $^{67}Ga$, $^{72}As$, $^{77}As$, $^{75}Br$, $^{76}Br$, 77Br, $^{82}Br$, $^{89}Zr$, $^{90}Y$, $^{94m}Tc$, $^{99m}Tc$, $^{97}Ru$, $^{105}Rh$, $^{109}Pd$, $^{111}Ag$, $^{110m}In$, $^{111}In$, $^{113m}In$, $^{114m}In$, $^{120}I$, $^{123}I$, $^{124}I$, $^{125}I$, $^{131}I$, $^{117m}Sn$, $^{121}Sn$, $^{127}Te$, $^{142}Pr$, $^{143}Pr$, $^{149}Pm$, $^{151}Pm$, $^{149}Tb$, $^{153}Sm$, $^{157}Gd$, $^{161}Tb$, $^{166}Ho$, $^{165}Dy$, $^{169}Er$, $^{169}Yb$, $^{175}Yb$, $^{172}Tm$, $^{177}Lu$, $^{186}Re$, $^{188}Re$, $^{191}Pt$, $^{197}Hg$, $^{198}Au$, $^{199}Au$, $^{201}Tl$, $^{203}Pb$, $^{211}At$, $^{212}Bi$ and $^{225}Ac$ and the radioactive ion $Al^{18}F^{2+}$; particularly from the group consisting of $^{18}F$, $^{68}Ga$, $^{67}Ga$, $^{64}Cu$, $^{89}Zr$, $^{90}Y$, $^{99m}Tc$, $^{111}In$, $^{123}I$, $^{124}I$, $^{131}I$, $^{177}Lu$ and the radioactive ion $Al^{18}F^{2+}$; especially from the group consisting of $^{64}Cu$, $^{67}Ga$, $^{68}Ga$, $^{99m}Tc$, $^{111}In$, $^{123}I$, $^{131}I$, $^{90}Y$, $^{177}Lu$, $^{212}Bi$, $^{225}Ac$ and the radioactive ion $Al^{18}F^{2+}$, wherein preferred combinations of radionuclides and complexation agents are defined in item 8, preferably the radionuclides are therapeutic radionuclides.

13. The compound of any of items 10-12, wherein $Xaa^1$ is an iodo-substituted D- or L-tyrosine amino acid or an iodo-substituted D- or L-homotyrosine amino acid, wherein preferably the tryrosine or homotyrosine, preferably tyrosine, is substituted with $^{127}I$, most preferably is 3-iodinated with $^{127}I$;

$Xaa^2$ is arginine;
$Xaa^3$ is naphthylalanine;
$Xaa^4$ is glycine;
L is a linker moiety selected from the following structures:

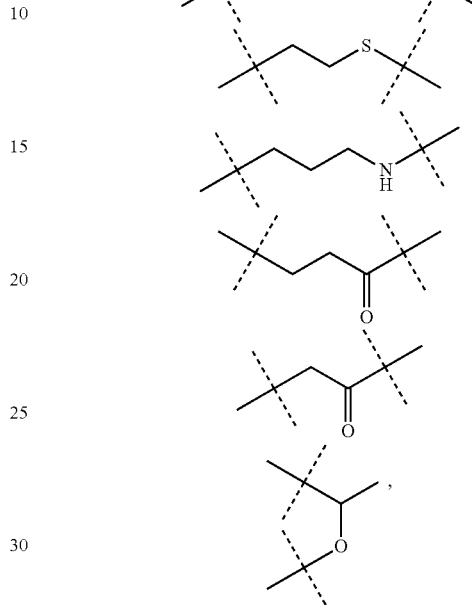

preferably L is:

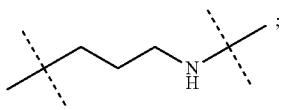

Ar is

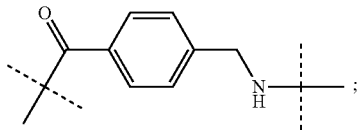

wherein D is a combination of a radionuclide and a complexation agent, with the complexation agent being covalently bound to Ar, wherein
i) the complexation agent is selected from the group consisting of NODASA, NODAGA, TETA, TRITA, TRAP, DTPA, CHX-DTPA EDTA, CDTA, CPTA, DOTP, DOTPI, EG-TA, HBED, TTHA, DTPA, DOTA, DOTAGA, NOTA, HP-DOA3, CBTE2a, TE2A, TMT, DPDP, HYNIC, DFO, HEDTA, NOPO. MAG3, NCS-MP-NODA, NH2-MPAA-NODA, and particularly from DOTA, DOTAGA, NOTA, DTPA, CHX-DTPA, NODA and functionalized NODA, TRAP, DOTPI, DOTP, NOPO and TETA, particularly selected from DOTA, NOTA, DTPA, and TETA, most preferably DOTA; and
ii) the radionuclide is selected from the group consisting of the diagnostic and therapeutic radionuclides $^{11}C$, $^{18}F$, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{72}$As, $^{77}$As, $^{75}$Br, $^{76}$Br, 77Br, $^{82}$Br, $^{89}$Zr, $^{90}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi and $^{225}$Ac and the radioactive ion $Al^{18}F^{2+}$; particularly from the group consisting of $^{18}$F, $^{68}$Ga, $^{67}$Ga, $^{64}$Cu, $^{89}$Zr, $^{90}$Y, $^{99m}$Tc, $^{111}$In, $^{123}$I, $^{124}$I, $^{131}$I, $^{177}$Lu and the radioactive ion $Al^{18}F^{2+}$; especially from the group consisting of $^{64}$Cu, $^{67}$Ga, $^{68}$Ga, $^{99m}$Tc, $^{111}$In, $^{123}$I, $^{131}$I, $^{90}$Y, $^{177}$Lu, $^{212}$Bi, $^{225}$Ac and the radioactiveion $Al^{18}F^{2+}$, wherein preferred combinations of radionuclides, wherein Ga is excluded, and complexation agents are defined in item 8, preferably the radionuclides are therapeutic radionuclides.

14. The compound of any of items 10-13, wherein $Xaa^1$ is the 3-iodinated D- or L-tyrosine amino acid or the 3-iodinated D- or L-homotyrosine amino acid, preferably is 3-iodinated tyrosine;

$Xaa^2$ is arginine;

$Xaa^3$ is naphthylalanine;

$Xaa^4$ is glycine;

L is a linker moiety selected from the following structures:

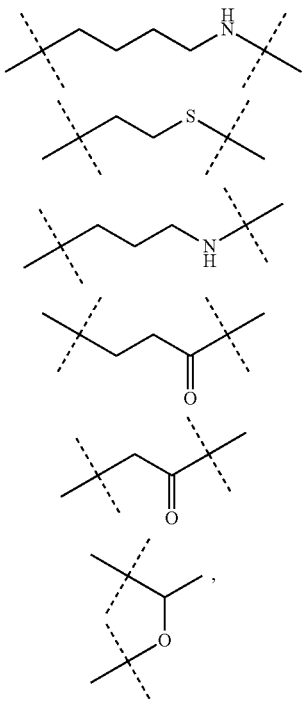

preferably L is:

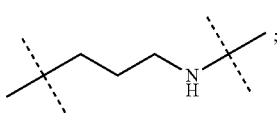

Ar is

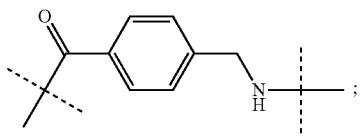

wherein D is a combination of a radionuclide and a complexation agent, with the complexation agent being covalently bound to Ar, wherein i) the complexation agent is selected from the group consisting of NODASA, NODAGA, TETA, TRITA, TRAP, DTPA, CHX-DTPA EDTA, CDTA, CPTA, DOTP, DOTPI, EG-TA, HBED, TTHA, DTPA, DOTA, DOTAGA, NOTA, HP-DOA3, CBTE2a, TE2A, TMT, DPDP, HYNIC, DFO, HEDTA, NOPO. MAG3, NCS-MP-NODA, NH2-MPAA-NODA, and particularly from DOTA, DOTAGA, NOTA, DTPA, CHX-DTPA, NODA and functionalized NODA, TRAP, DOTPI, DOTP, NOPO and TETA, particularly selected from DOTA, NOTA, DTPA, and TETA, most preferably DOTA; and ii) the radionuclide is selected from the group consisting of the diagnostic and therapeutic radionuclides $^{11}$C, $^{18}$F, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{72}$As, $^{77}$As, $^{75}$Br, $^{76}$Br, $^{77}$Br, $^{82}$Br, $^{89}$Zr, $^{90}$Y, $^{94m}$Tc, $^{99m}$Tc, $^{97}$Ru, $^{105}$Rh, $^{109}$Pd, $^{111}$Ag, $^{110m}$In, $^{113m}$In, $^{114m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl $^{203}$Pb, $^{211}$At, $^{212}$Bi and $^{225}$Ac and the radioactive ion $Al^{18}F^{2+}$; particularly from the group consisting of $^{18}$F, $^{64}$Cu, $^{89}$Zr, $^{90}$Y, $^{99m}$Tc, $^{111}$In, $^{123}$I, $^{124}$I, $^{131}$I, $^{177}$Lu and the radioactive ion $Al^{18}F^{2+}$; especially from the group consisting of $^{111}$In, $^{64}$Cu, $^{90}$Y, $^{99m}$Tc, $^{177}$Lu, $^{212}$Bi, $^{225}$Ac and the radioactive ion $Al^{18}F^{2+}$, wherein preferred combinations of radionuclides, wherein Ga is excluded, and complexation agents are defined in item 8, in particular Lu with DOTA, DOTPI, DOTAGA, DTPA and CHX-DTPA and in particular Lu with DOTA, DOTPI, DOTAGA, Y with DOTA, DOTPI, DOTAGA, DTPA and CHX-DTPA and in particular Y with DOTA, DOTPI, DOTAGA, In with DOTA, DOTPI, DOTAGA, DTPA and CHX-DTPA and in particular In with DOTA, DTPA, DOTPI, DOTAGA, Bi with DOTA, DOTPI, DOTP, DOTAGA, DTPA and CHX-DTPA and in particular Bi with DOTA, DOTPI, DOTP, DOTAGA, Cu with NOTA, TRAP, NOPO, DOTPI and NODAGA and in particular Cu with NOTA, TRAP, NOPO, DOTPI, Tc with DTPA, HYNIC and $MAG_3$, And combinations from $Al^{18}F^{2+}$ with functionalized NODA, such as NH2-MPAA-NODA or NCS-MP-NODA, or NODAGA, DOTA or CHX-DTPA, and in particular $Al^{18}F^{2+}$ with functionalized NODA, NODAGA, DOTA or CHX-DTPA.

15. A compound having a structure according to formula (II)

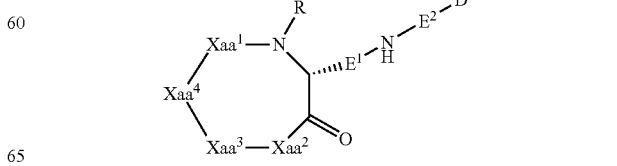

or a pharmaceutically acceptable salt thereof, wherein Xaa¹ is selected from the group consisting of iodo-substituted or methyl-substituted amino acids D- and L-Tyr, iodo-substituted or methyl-substituted D- and L-homotyrosine, iodo-substituted or methyl-substituted D- and L-Phe, iodo-substituted or methyl-substituted D- and L-p-OH-phenylglycine, and iodo-substituted or methyl-substituted D- or L-Trp Xaa² to Xaa⁴ are independently of each other, an optionally N-alkylated natural or unnatural amino acid, R is H or methyl, $E^1$ is —$(CH_2)_e$— with e being selected from 1, 2 and 3, particularly with e being 3, $E^2$ is a spacing moiety composed of 0 to 20 units of bifunctional linkers, preferably wherein E is selected from —(C═O)—$CH_2$—NH—, —(C═O)—$(CH_2)_2$—NH—, —(C═O)—$(CH_2)_3$—NH—, —(C═O)—$(CH_2)_4$—NH—C(═O)—$(CH_2)_4$—NH—, —C(═O)—$CH_2$—O—$(CH_2)_2$—O—$(CH_2)_2$—NH— and —(C═O)—$CH_2$—NH—C(═O)—$CH_2$—O—$(CH_2)_2$—O—$(CH_2)_2$—NH—, and D comprises, preferably is i) a combination of an organic complexation agent and a radioactive or detectable label; or ii) a radioactive or detectable label, an organic complexation agent or an active substance, said active substance particularly being selected from cytotoxic agents, lipids, sugars, sugar conjugates, sugar derivatives, proteins and combinations thereof particularly wherein the compound has a structure according to formula (II')

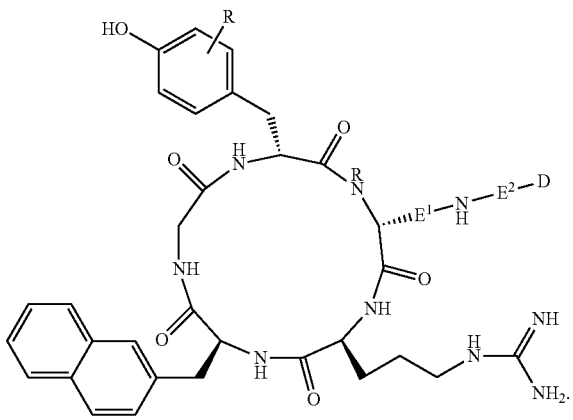

(II')

16. The compound of item 15, wherein Xaa¹ is selected from the group consisting of the iodo-substituted or methyl-substitued amino acids D- and L-Tyr, iodo-substituted or methyl-substituted D- and L-homotyrsine, iodo-substituted or methyl-substituted D- and L-Phe, iodo-substituted or methyl-substituted D- and L-p-OH-phenylglycine, and iodo-substituted or methyl-substituted D- or L- Trp Xaa² to Xaa⁴, R and D are as defined in any one of items 2 to 9;

particularly wherein D is selected from chelators as defined in item 8 and a combination of any chelator as defined in item 8 with any radionuclide as defined in item 8;

17. A pharmaceutical composition comprising a compound as defined in any of items 1 to 16 and at least one pharmaceutically acceptable excipient.

18. A compound as defined in any of items 1 to 16 or composition as defined in item 17 i) for use as a medicament; or ii) for use in a method for the prevention of a CXCR4 receptor-related disease or disorder; or iii) for use in a method for treatment of a CXCR4 receptor-related disease or disorder, preferably an peptide receptor radionuclide therapy, practiced on the human or animal body for the treatment of a CXCR4 receptor-related or mediated disease or disorder iv) for use in a diagnostic method practiced on the human or animal body for the diagnosis of a CXCR4 receptor-related or mediated disease or disorder; or v) for use in a method of imaging CXCR4 receptors, in particular of medical imaging, especially of diagnostic imaging, said method involving at least one step of treatment of the human or animal body by surgery, radioguided surgery or therapy.

19. Use of a compound as defined in any of items 1 to 16 or of a composition as defined in item 17, wherein the compound comprises a radioactive or detectable label, for the imaging of CXCR4 receptors and CXCR4 receptor related or mediated diseases or disorders, in particular for medical imaging, especially for diagnostic imaging.

20. A method of imaging CXCR4 receptors, in particular of medical imaging, especially of diagnostic imaging, peptide receptor radionuclide therapy or radioguided surgery, the method comprising administering a compound as defined in any of items 1 to 16 to a sample or a subject, wherein the compound comprises a radioactive or detectable label.

The Structural Unit-Xaa-:

As far as the structural units-Xaa²-, -Xaa³-and-Xaa⁴- are concerned, in the context of the present invention, the general structure-Xaa- is denoted to encompass natural as well as unnatural amino acids, optionally being substituted at the alpha nitrogen (N-alpha) of said amino acid with an alkyl group, such as a methyl group or ethyl group.

In this context, the term "alkyl group" preferably refers to a linear or branched, optionally substituted, saturated aliphatic chain of preferably 1 to 12, more preferably 1 to 8, and more preferably 1 to 6 carbon atoms and includes, but is not limited to, optionally substituted methyl, ethyl, propyl, isopropyl, n-butyl, sec-butyl, tert-butyl, pentyl, isopentyl, and hexyl. The alkyl group may be interrupted by one or more heteroatoms, cyclic groups and/or heterocyclic groups. The term "substituted" as used in this context preferably refers to alkyl groups being substituted in any position by one or more substituents, preferably by 1, 2, 3, 4, 5 or 6 substituents, more preferably by 1, 2, or 3 substituents. If two or more substituents are present, each substituent may be the same or may be different from the at least one other substituent. Suitable substituents are known to the skilled person. A substituent may be, for example, a halogen atom, a hydroxy, an amino group or an alkoxy group. In this context, the term "alkoxy" preferably represents a linear or branched alkyl group, preferably having from 1 to 6 carbon atoms attached to an oxygen atom. Typical alkoxy groups include methoxy, ethoxy, propoxy, isopropoxy, butoxy, t-butoxy, pentoxy, and the like. The term "halogen atom" preferably refers to a chlorine, iodine, bromine or fluorine atom. Preferred halogen atoms are fluorine and/or chlorine atoms.

Preferably the amino acids-Xaa²-, -Xaa³- and -Xaa⁴- are, independently of each other either N-alpha-methylated amino acids or are substituted with a hydrogen (H) in N-alpha-position. Preferably all amino acids-Xaa$^2$-, -Xaa$^3$- and -Xaa$^4$-are substituted in N-alpha-position with a hydrogen.

The term "natural amino acid" refers to naturally occurring amino acids or residues which typically occur in proteins including their stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val).

The term unnatural amino acid includes any conceivable amino acid. This term includes amino acids bearing a side chain comprising acidic, basic, neutral and/or aromatic moieties. Conceivable amino acids to be mentioned are, for example, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, nor-valine, nor-leucine, ornithine, naphthylalanine, diaminopropionic acid, N-(fluoropropionyl)-diaminobutyric acid, N-fluorobenzoyl-diaminobutyric acid, N-fluorobenzoyl-diaminopropionic acid, citrulliune and pipecolic acid.

As regards the general amino acid abbreviations Xaa$^1$, Xaa$^2$, Xaa$^3$, Xaa$^4$, said abbreviations encompass the L-enantiomer as well as the respective D-enantiomers.

The Amino Acid Xaa$^1$:

Xaa$^1$ refers to the iodo-substituted or methyl-substituted amino acids D- and L-Tyr, iodo-subsititued or methyl-substituted D- and L- homotyrosine, iodo-substituted or methyl-substituted D- and L-Phe, iodo-substituted or methyl-substituted D- and L- p-OH-phenylglycine, and iodo-substituted or methyl-substituted D- or L-Trp. In the context of the present invention, the term "iodo-substituted" refers to the use of a radioactive or non-radioactive iodine isotope as substituent of an amino acid.

The amino acids are identified by their commonly used abbreviations: alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). The term "iodo-substituted" further refers to the substitution of one amino acid with one iodine. Likewise, "methyl-substituted refers to the substitution of one amino acid with one methyl group. Thus, in case D- or L-Tyr, D- and L-homotyrosine, D- or L-Phe, D- and L- p-OH-phenylglycine, or D- or L-Trp being substituted at one position of the aromatic ring with an iodine, the iodine may be selected from the group consisting of natural iodine ($^{127}$I), $^{123}$I, $^{120}$I, $^{124}$I, $^{125}$I, and $^{131}$I. Similarly, the aforementioned amino acids are substituted at one position of the aromatic ring with a methyl group. Most preferably, Xaa$^1$ is an 3-iodinated or 3-methylated D-tyrosine.

The term "alkyl chain" and the term "alkyl", as used in this context of the invention preferably refers to alkyl chains or alkyl groups of 1 to 5 carbon atoms, preferably of 1 to 3 carbon atoms, more preferably of 1 to 2 carbon atoms, most preferably of 1 carbon atom.

Preferably, Xaa$^1$ is present in enantiomerically pure form.

The term "enantiomerically pure" as used in the context of the present invention refers to compounds having an enantiomeric excess of at least 95% (i.e. minimum 97.5% of one enantiomer and maximum 2.5% of the other enantiomer) up to an enantiomeric excess of 100% (i.e. 100% of one enantiomer and none of the other), in particular compounds having an enantiomeric excess of at least 98%, more in particular having an enantiomeric excess of at least 99.% and most in particular having an enantiomeric excess of at least 99.9%, especially of 100%.

Most preferably, the amino acid Xaa$^1$ is present in D-configuration. Thus, the present invention also relates to a compound having the following structure with Xaa$^1$, Xaa$^2$ to Xaa$^4$, L, Ar, D and R being as described above and below:

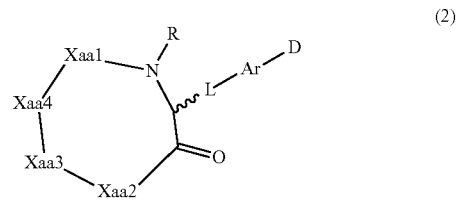

(2)

A preferred embodiment is-a compound having the general structure:

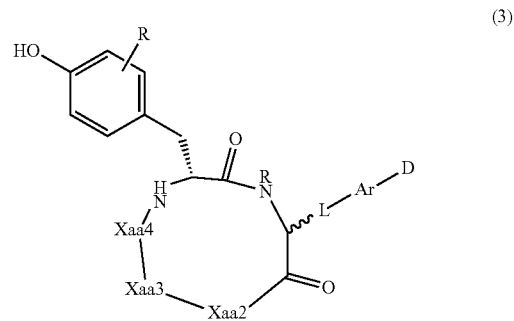

(3)

with Xaa$^2$ to Xaa$^4$, L, Ar, D and R being as described above and below. Most preferably, Xaa$^1$ is an 3-iodinated or 3-methylated D-tyrosine.

The Amino Acid Xaa$^2$:

Xaa$^2$ preferably is a natural or unnatural basic amino acid. In the context of the present invention the term "natural or unnatural basic amino acid" refers to residues of any naturally occurring or synthetic amino acid comprising a basic group in its side chain and their respective D and L stereoisomers if their structures allow such stereoisomeric forms.

The term "basic amino acid" refers to any amino acid having a basic residue such as a primary, secondary or tertiary amine, or a cyclic nitrogen containing ring and their respective isomeric forms. Basic preferably means a group, which has a net positive charge at pH 6 or lower in aqueous solvents. Naturally occurring basic amino acids or residues which typically occur in proteins include arginine (Arg), histidine (His) and lysine (Lys).

The terra unnatural basic amino acid includes any conceivable basic amino acid, thus this term includes amino acids comprising at least one basic moiety in its side chain.

In this context of the invention, the term residues refers to building blocks being incorporated in the cyclic pentapeptide having the structure:

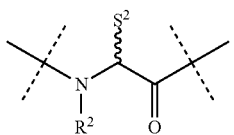

(4)

wherein S² is the side chain of the natural or unnatural basic amino acid. S² may form a cyclic ring with the group N, in particular in case Xaa² is a proline derivative.

R² in the above shown structure is a hydrogen atom or an alkyl group, preferably a hydrogen atom or a methyl group, in particular a hydrogen atom. Thus, more preferably Xaa² is a building block having the structure:

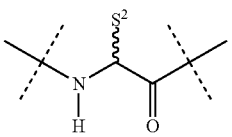

(4')

said building block being incorporated in the cyclic pentapeptide of formula (1).

Preferably S² comprises at least one basic group, preferably one basic group selected from the group consisting of amino groups, guanidine groups or guanidine mimics. According to one preferred embodiment, S² comprises a guanidine group.

According to a preferred embodiment of the invention S² is an alkyl chain being substituted with the at least one basic group, thus, preferably with one basic group selected from the group consisting of amino groups, guanidine groups guanidine mimics, most preferably with a guanidine group. Basic group and basic moiety are used interchangeably herein.

The amino acid Xaa² may have multiple asymmetric centers. As a consequence, the resulting cyclopeptides may occur as racemates, mixtures of enantiomers and as individual enantiomers, as well as diastereomers and mixtures of diastereomers. All asymmetric forms, possible stereoisomers, single isomers and mixtures of isomers are included within the scope of the present invention. The designation "⤳" shown in formulas (IV) and (IV') above refers to a bond to which the stereochemistry is not specifically designated.

Preferably, the amino acid Xaa² is present in L-configuration. Thus, the present invention also relates to a compound having the following structure:

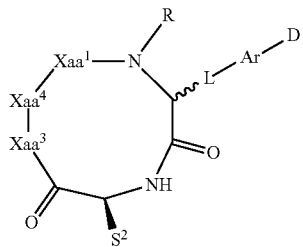

(5)

As regards, the side chain S², preferably said side chain is an alkyl chain having from 1 to 6, preferably from 1 to 4, carbon atoms, wherein said alkyl chain is substituted with a functional group selected from the group of —NH₂ and guanidine.

Especially preferred amino acids to be mentioned for Xaa² are, for example, ornithine (Orn or D-Orn), diaminopropionic acid (Dap or D-Dap), arginine, lysine or homolysine.

More preferably Xaa² is L-arginine or D-arginine, in particular L-arginine.

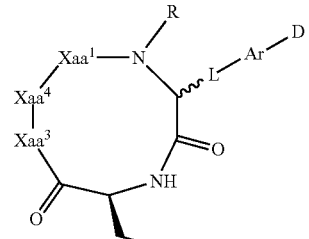

(6)

or

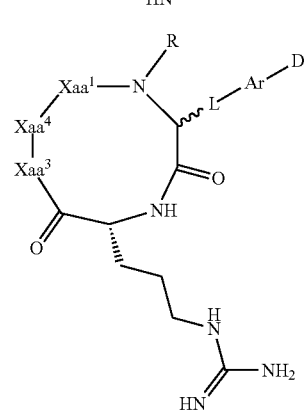

(6')

The Amino Acid Xaa³:

Xaa³ is a natural or unnatural amino acid. As already described above, the term "natural or unnatural amino acid" refers to residues of any naturally occurring or synthetic amino acid and their respective D and L stereoisomers if their structures allow such stereoisomeric forms.

In this context of the invention, the term residues refers to building blocks being incorporated in the cyclic pentapeptide having the structure:

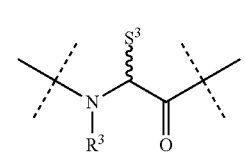

(7)

wherein S³ is the side chain of the natural or unnatural amino acid. For example in case the amino acid is glycine S³ is H. S³ may form a cyclic ring with the group N, in particular in case Xaa³ is proline or a proline derivative.

R³ in the above shown structure is a hydrogen atom or an alkyl group as defined above, preferably a hydrogen atom or a methyl group, in particular a hydrogen atom.

Thus, more preferably Xaa³ is a building block having the structure:

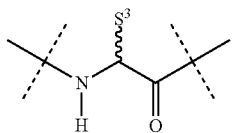

(7')

said building block being incorporated in the cyclic pentapeptide of formula (1).

Preferably Xaa³ is a naturally or unnaturally amino acid comprising an aromatic moiety in its side chain S³. As regards, the term "amino acid comprising an aromatic moiety in its side chain" this term refers to an amino acid, the side chain of which comprises an aromatic group as described above. This includes side chains, with the aromatic moiety being directly attached to the $C^{alpha}$ of the amino acid, thus with S³ being the aromatic moiety, as well as side chains S³ being substituted in any position with at least one aromatic moiety, such as for example alkyl chains being substituted with an aromatic moiety.

The term aromatic moiety as used in this context of the invention, refers to an optionally substituted aryl group and/or optionally substituted heteroaryl group, with the terms, terms "aryl" and "substituted aryl", "heteroaryl" and "substituted heteroaryl" being as defined above.

The amino acid Xaa³ may have multiple asymmetric centers. As a consequence, the resulting cyclopetides may occur as racemates, mixtures of enantiomers and as individual enantiomers, as well as diastereomers and mixtures of diastereomers. All asymmetric forms, possible stereoisomers, single isomers and mixtures of isomers are included within the scope of the present invention. The designation "~~~" shown in formula (VII) and (VII') above refers to a bond to which the stereochemistry is not specifically designated.

Preferably, Xaa³ is present in enantiomerically pure form. Preferably, the amino acid Xaa³ is present in L-configuration. Thus, the present invention also relates to a compound having the following structure:

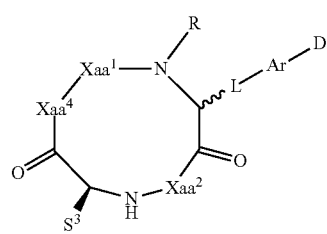

(8)

As regards the side chain S³, according to a preferred embodiment of the present invention, said side chain comprises an aromatic group being selected from, optionally substituted, phenyl, naphthyl and indole, most preferably, S³ comprises an aromatic group being naphthyl.

According to a preferred embodiment, Xaa³ is selected from the group consisting of phenylalanine, tyrosine, tryptophan, phenylglycine, and naphthylalanine, i.e. Xaa³ is most preferably selected from the group consisting of L-phenylalanine (Phe), D-phenylalanine (D-Phe), L-tyrosine (Tyr), D-tyrosine (D-Tyr), L-tryptophan (Trp), D-tryptophan (D-Trp), D-phenylglycine (D-Phg), L-phenylglycine (Phg), L-naphthylalanine (Nal) and D-naphthylalanine (D-Nal).

Thus, the present invention relates to a compound, as described above, wherein Xaa³ is independently of each other, selected from the group phenylalanine, D-phenylalanine, tyrosine, D-tyrosine, tryptophan, D-tryptophan, D-phenylglycine, phenylglycine, naphthylalanine (Nal) and D-naphthylalanine (D-Nal).

According to preferred embodiments, Xaa³ is tryptophan or naphthylalanine.

According to a particular preferred embodiment, Xaa³ is L-naphthylalanine (Nal) or D-naphthylalanine (D-Nal), more preferably L-naphthylalanine.

In case, Xaa³ is Nal, e.g. the following structures are conceivable:

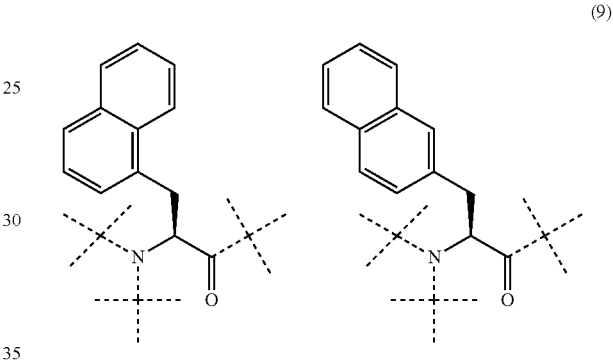

(9)

with L-2-naphtylalanine (2-Nal) being particularly preferred.

Thus according to a particular preferred embodiment, the present invention relates to a compound having the structure:

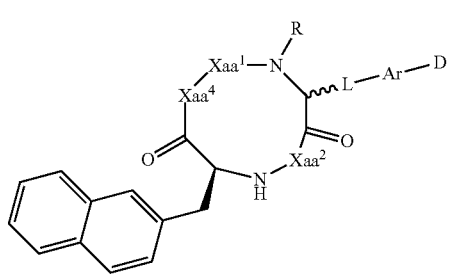

(10)

According to other particularly preferred embodiments of the invention, Xaa³ is tryptophan.

The Amino Acid Xaa⁴:

Xaa⁴ preferably is glycine or a D-amino acid of a natural or unnatural amino acid. As already described above, the term "natural or unnatural amino acid" refers to residues of any naturally occurring or synthetic amino acid. In this context of the invention, the term residues refers to building blocks being incorporated into the cyclic pentapeptide having the structure:

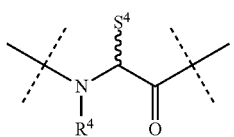

(11)

wherein $S^4$ is the side chain of the natural or unnatural amino acid. For example, in case the amino acid is glycine, $S^4$ is H. $S^4$ may form a cyclic ring with the group N, in particular in case $Xaa^4$ is a proline derivative $R^4$ in the above shown structure is a hydrogen atom or an alkyl group as defined above, preferably a hydrogen atom or a methyl group, in particular a hydrogen atom.

Thus, more preferably $Xaa^4$ is a building block having the structure:

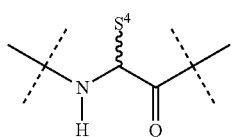

(11')

said building block being incorporated in the cyclic pentapeptide of formula (1).

According to one preferred embodiment, $S^4$ is the side chain of the natural or unnatural amino acid.

In case $Xaa^4$ is a D-amino acid, the D-amino acid is preferably selected from the group consisting of D-diaminopropionic acid, D-diaminobutyric acid, D-ornithine, and D-lysine.

The amino acid $Xaa^4$ may have multiple asymmetric centers. As a consequence, the resulting cyclopeptides may occur as racemates, mixtures of enantiomers and as individual enantiomers, as well as diastereomers and mixtures of diastereomers. All asymmetric forms, possible stereoisomers, single isomers and mixtures of isomers are included within the scope of the present invention. The designation "⁓" in formula (VI) and (VI') above refers to a bond to which the stereochemistry is not specifically designated. Preferably, the stereocenter in $C^{alpha}$ position, which is shown as "⁓" in formula (VI) and (VI') is selected in the way that, in case $Xaa^4$ is not glycine, the resulting amino acid $Xaa^4$ is present in D-conformation.

Preferably, $Xaa^4$ is present in enantiomerically pure form. Preferably, the amino acid $Xaa^4$ is present in D-configuration. Thus, the present invention also relates to a compound having the following structure:

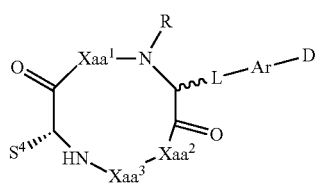

(12)

According to a preferred embodiment, $Xaa^4$ is selected from the group consisting of D-diaminopropionic acid, D-diaminobutyric acid, D-ornithine, D-lysine.

According to another preferred embodiment, $Xaa^4$ is glycine.

The Residue R:

As regards residue R, this residue is a methyl group or a hydrogen, preferably a methyl group.

The Structural Unit L-Ar

In general, there are no particular restrictions as to the chemical nature of the linker L and Ar with the proviso that the structural unit-L-Ar- is suitable for linking the further compound D to the alpha-carbon-atom of the backbone of the pentapeptide and provides suitable chemical properties for the novel derivatives as far as their intended uses are concerned.

Preferably the linker L is a spacer comprising at least one structural unit having the formula —$(C(R^5R^6))_n$— wherein $R^5$ and $R^6$ are, independently from each other, a hydrogen or a residue selected from the group consisting of, optionally substituted, alkyl, alkenyl, alkynyl, aryl, arylalkyl, and alkylaryl. More preferably $R^5$ and $R^6$ are, independently from each other, H or an alkyl group, most preferably, both $R^5$ and $R^6$ are H.

As far as integer n is concerned, n is preferably from 1 to 20, preferably from 1 to 15, more preferably from 1 to 10, more preferably from 1 to 5, such as 1, 2, 3, 4 or 5, more preferably 3.

If integer n is greater than 1, the groups —$C(R^5R^6)$— may be the same or different from each other. Furthermore, these groups may be linked directly to each other or at least two such structure units may be separated by a heteroatom such as O or S.

According to a preferred embodiment of the present invention, groups —$C(R^5R^6)$— directly linked to each other have the same constitution. Most preferably L thus comprises the group —$(CH_2)_n$— with n being from 1 to 10, preferably from 1 to 5, in particular 3.

Therefore, according to a particularly preferred embodiment of the present invention, spacer L comprises the group —$CH_2$—$CH_2$—$CH_2$—.

According to an alternative embodiment, L comprises at least one structure unit —$[(CR^5R^6)_n$—O—$(CR^5R^6)_m]_p$—, preferably —$[(CH_2)_n$—O—$(CH_2)_m]_p$— wherein n is equal to or different from m and wherein m and n are, independently of each other from 0 to 10, with the proviso that when one of n and m is 0, the other one is not 0, preferably wherein m+n=2; and wherein p is from 1 to 10, preferably from 1 to 5, more preferably from 1 to 2.

Besides the structural unit —$(C(R^5R^6))_n$— L preferably further comprises at least one chemical moiety different from —$(CR^5R^6)$—. Said chemical moiety is preferably a functional group X. The functional group X is preferably linking L and Ar.

In general, there no particular restrictions as to the chemical nature of the functional group X, with the proviso that, if present, the functional group X is suitable for linking the linker L to the moiety Ar. Preferably the functional group X is linked to a functional group Y optionally being present in the moiety Ar.

The functional group X may be, for example a group derived from a group selected from the group consisting of C—C-double bond, thio group, hydroxy group, hydrazide, azides; amino group —$NH_2$, derivatives of an amino groups comprising the structure unit —NH—, a hydroxylamino group —O—$NH_2$, a carboxy group, a carbonyl group, a thio reactive group such as a maleimide group, a halogen group, an alkynyl group or the like. According to a most preferred embodiment, L comprises a functional group being an amino group —NH$_2$ or a derivative of an amino group comprising the structure unit —NH—.

Likewise the functional group Y of the Ar moiety may be, for example a group derived from a group selected from the group consisting of C—C-double bond, thio group, hydroxy group, hydrazide, azides; amino group —NH$_2$, derivatives of an amino groups comprising the structure unit —NH—, a hydroxylamino group —O—NH$_2$, a carboxy group, a carbonyl group, a thio reactive group such as a maleimide group, a halogen group, an alkynyl group or the like.

If present, both functional groups X and Y preferably form a linking group selected from the group consisting of =N—, —N=, —Z—, —C(=Z)—NH—, —NH—C(=Z)—, —NH—C(=Z)—Z'—, —Z'—C(=Z)—NH—, —Z'—C(=Z)—, —C(=Z)—Z'—, —C(=Z), —S—S—, —S—CH$_2$—C(=O)—O, —O—C(=O)—CH$_2$—S—, —S-maleimide-, -maleimide-S—, —C=NH—O—, —O—NH=C— and 1,2,3-triazole, with Z and Z' being independently of each other selected from the group consisting of NH, O and S, preferably wherein L comprises a —NH—C(=O)— group.

Thus, the present invention also relates to a compound having the following structure:

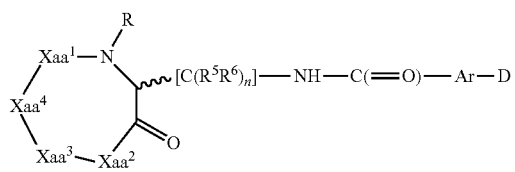
(13)

Thus, the present invention also relates to a compound, as described above, wherein L is a linker moiety comprising at least one functional group, the at least one functional group being selected from the group consisting of =N—, —N=, —Z—, —C(=Z)—NH—, —NH—C(=Z)—, —NH—C(=Z)—Z'—, —Z'—C(=Z)—NH—, —Z'—C(=Z)—, —C(=Z)—Z'—, —C(=Z)—, —S—S—, —S—CH$_2$—C(=O)—O, —O—C(=O)—CH$_2$—S—, —S-maleimide-, -maleimide-S—, —C=NH—O—, —O—NH=C—, and 1,2,3-triazole, with Z and Z' being independently of each other selected from the group consisting of NH, O and S, preferably wherein L comprises a —NH—C(=O)—group.

Most preferably the linker L is the side chain of an amino acid such as lysine, homolysine, glutamic acid, aspartic acid, cysteine, serine, ornithine, threonine. Thus, the linker L is preferably selected from the following structures:

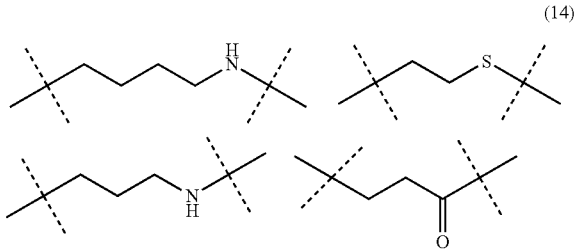
(14)

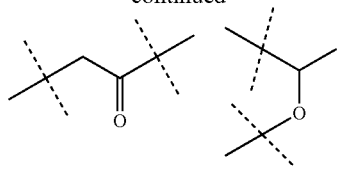

Most preferably L is selected from the followings structures:

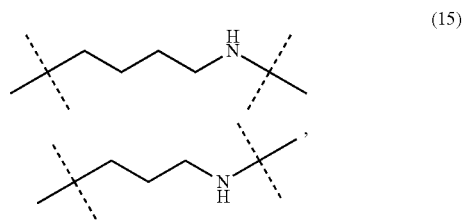
(15)

with

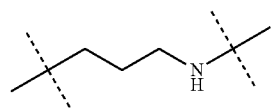

being preferred.

As regards the moiety Ar, there are no particular restrictions as to the chemical nature of Ar with the proviso that Ar comprises an aromatic moiety.

The term aromatic moiety as used in this context of the invention, refers to an optionally substituted aryl group and/or heteroaryl group, wherein the term "aryl", in turn, refers to, but is not limited to, optionally suitably substituted 5- and 6-membered single-ring aromatic groups as well as optionally suitably substituted multicyclic groups, for example bicyclic or tricyclic aryl groups. The term "aryl" thus includes, for example, optionally substituted phenyl groups or optionally suitably substituted naphthyl groups. Aryl groups can also be fused or bridged with alicyclic or heterocycloalkyl rings which are not aromatic so as to form a polycycle, e.g., benzodioxolyl or tetraline. The term heteroaryl includes optionally suitably substituted 5- and 6-membered single-ring aromatic groups as well as substituted or unsubstituted multicyclic aryl groups, for example tricyclic or bicyclic aryl groups, comprising one or more, preferably from 1 to 4 such as 1, 2, 3 or 4, heteroatoms, wherein in case the aryl residue comprises more than 1 heteroatom, the heteroatoms may be the same or different. Such heteroaryl groups including from 1 to 4 heteroatoms are, for example, benzodioxolyl, pyrrolyl, furanyl, thiophenyl, thiazolyl, isothiaozolyl, imidazolyl, triazolyl, tetrazolyl, pyrazolyl, oxazolyl, isoxazolyl, pyridinyl, pyrazinyl, pyridazinyl, benzoxazolyl, benzodioxazolyl, benzothiazolyl, benzoimidazolyl, benzothiophenyl, methylenedioxyphenylyl, naphthridinyl, quinolinyl, isoquinolinyl, indolyl, benzofuranyl, purinyl, benzofuranyl, deazapurinyl, or indolizinyl.

The tetin "substituted aryl" and the term "substituted heteroaryl" as used in the context of the present invention describes moieties having substituents replacing a hydrogen on one or more atoms, e.g. C or N, of an aryl or heteroaryl moiety. There are in general no limitations as to the substituent. The substituents may be, for example, selected from the group consisting of alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, amino, acylamino, including alkylcarbonylamino, arylcarbonylamino, carbamoyl and ureido, amidino, nitro, imino, sulfhdryl, alkylthio, arylthio, thiocarboxylate, sulfates, alkylsulfinyl, sulfonate, sulfamoyl, sulfonamido, trifluoromethyl, cyano, azido, heterocyclyl, alkylaryl, morpholino, piperizinyl, cyclopentanyl, cyclohexanyl, and piperidinyl.

Preferably, Ar comprises a phenyl group.

Besides, the aryl group and/or heteroaryl group, Ar further optionally comprises further spacer groups. Preferably the aryl group and/or heteroaryl group is linked via a spacer moiety to the further compound D ("spacer 1" or "spacer moiety 1") and/or via a spacer moiety ("spacer 2" or "spacer moiety 2") to linker L.

As regards, the spacer moiety 1, said group preferably comprises at least one functional group W, linking the aryl group and/or heteroaryl group to the further compound D.

The functional group W may be, for example, a group derived from a group selected from the group consisting of C—C-double bond, thio group, hydroxy group, hydrazide, azides; amino group —$NH_2$, derivatives of amino groups comprising the structure unit —NH—, a hydroxylamino group —O—$NH_2$, a carboxy group, a carbonyl group, a thio reactive group such as a maleimide group, a halogen group, an alkynyl group or the like. Preferably W is a —NH— group.

Optionally, spacer moiety 1, additionally comprises at least one structural unit having the formula —$(C(R^7R^8))_q$— wherein $R^7$ and $R^8$ are, independently from each other, a hydrogen or a residue selected from the group consisting of, optionally substituted, alkyl, alkenyl, alkynyl, aryl, arylalkyl, and alkylaryl. More preferably $R^7$ and $R^8$ are, independently from each other, H or an alkyl group, most preferably both $R^7$ and $R^8$ are H.

As far as integer q is concerned, n is preferably from 1 to 20, preferably from 1 to 15, more preferably from 1 to 10, more preferably from 1 to 5, such as 1, 2, 3, 4 or 5, more preferably 1

If integer q is greater than 1, the groups —$C(R^7R^8)$— may be the same or different from each other. Furthermore, these groups may be linked directly to each other or at least two such structure units may be separated by a heteroatom such as O or S.

According to a preferred embodiment of the present invention, groups —$C(R^7R^8)$— directly linked to each other have the same constitution. Most preferably Ar thus comprises the group —$(CH_2)_q$— with q being from 1 to 10, preferably from 1 to 5, in particular 1.

Therefore, according to a particularly preferred embodiment of the present invention, spacer Ar comprises the group —$CH_2$—. Accordingly, in particularly preferred embodiments, W comprises the group —$CH_2$—NH—, particularly W is the group —$CH_2$—NH—. Especially, spacer 1 comprises the group —$CH_2$—NH—. According to other preferred embodiments, spacer 1 comprises the group —NH—C(=O)—$CH_2$—$CH_2$—NH—. Other preferred embodiments for spacer 1 and compound Ar are disclosed in the particular Examples herein.

According to an alternative embodiment, the spacer 1 comprises at least one structure unit —$[(CR^7R^8)_q$—O—$(CR^7R8_6)_r]_s$—, preferably —$[(CH_2)_q$—O—$(CH_2)_r]_s$— wherein q is equal to or different from r and wherein q and r are, independently of each other from 0 to 10, 0 to 10, with the proviso that when one of r and q is 0, the other one is not 0, preferably wherein r+q=2, and wherein s is from 1 to 10, preferably from 1 to 5, more preferably from I to 2.

Besides the functional group W and optionally the structural unit —$(C(R^7R^8))_q$—, spacer 1 may also comprise a further bifunctional linking compound linking the functional group W to a functional group of the compound D. As regards said bifunctional linking compounds, any linking compound known to those skilled in the art suitable for coupling the functional group W to functional group of the further compound can be used.

Thus, the present invention also relates to a compound as described above, wherein Ar further comprises a spacer moiety 1 linking the optionally substituted aryl or heteroaryl moiety to the further compound D, said spacer moiety optionally comprising a bifunctional linker.

According to preferred embodiments, the spacer 1 preferably has the structure —NH—, —$CH_2$—NH—, —$CH_2$—$CH_2$—NH— or —$CH_2$—$CH_2$—$CH_2$—NH—, wherein said spacer 1 is either directly attached to compound D or via a suitable bifunctional linking compound.

Both functional groups in the bifunctional linking compound can preferably form a linking group selected from the group consisting of =N—, —N=, —Z—, —C(=Z)—NH—, —NH—C(=Z)—, —NH—C(=Z)—Z'—, —Z'—C(=Z)—NH—, —Z'—C(=Z)—, —C(=Z)—Z'—, —C(=Z)—, —S—S—, —S—$CH_2$—C(=O)—O, —O—C(=O)—$CH_2$—S—, —S-maleimide-, -maleimide-S—, —C=NH—O—, —O—NH=C— and 1,2,3-triazole, with Z and Z' being independently of each other selected from the group consisting of NH, O and S, preferably wherein the bifunctional linker comprises a —NH—C(=O)—group).

According to preferred embodiments, the bifunctional linking compound is derived from a linking agent selected from the group consisting of amino acids, diamines, dicarboxylic acids, aminoalcohols, hydroxocarboxylic acids, mercaptocarboxylicacids, mercaptoamines, dithiols, aminoalkynes, dialkynes, alkinocarboxylic acids, diazides, azidoamines, azidocarboxylic acids. More preferably, the bifunctional linking compound is an amino acid.

Preferred bifunctional linkers comprise a functional group capable of being coupled to the group W, preferably to a group —NH—, such as carbonyl or carboxyl groups. Most preferably the bifunctional group comprises a carboxyl group to be coupled to the functional group W and an amino group to be coupled to the compound D.

The following bifunctional linkers are preferred: —C(=O)—$(CH_2)$—NH— with the integer u being from 1 to 8, preferably from 1 to 5, most preferably 2.

According to a preferred embodiment, the aromatic group is a phenyl group. Preferably said phenyl group is linked to the Linker L as well as to the further compound D, wherein the Linker L and compound D are attached to the phenyl ring, optionally via additional suitable spacer moieties, and are positioned in ortho, meta or para positions to each other, preferably in para position.

Thus, according to a preferred embodiment, Ar is a moiety comprising a para substituted phenyl group; Thus, the following structure is preferred, wherein spacer 2, spacer 1, and bifunctional linking compound are, independently of each other either present or absent, and if presented selected from the groups as described above.

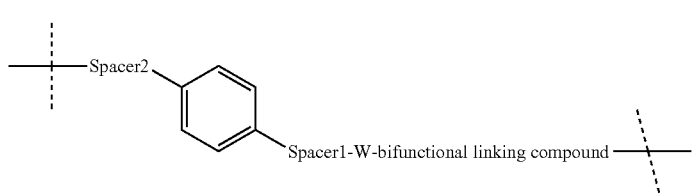

(16)

As regards the spacer moiety 2, said spacer preferably comprises a functional group Y to be linked to the functional group X. Optionally, the spacer 2 comprises, independently from spacer 1, at least one structural unit having the formula —$(C(R^7R^8))_q$—. Reference is made to the description of group —$(C(R^7R^8))_q$— above.

As regards the functional group Y, all conceivable groups capable of being coupled to the functional group X may be used. Reference is made to the description of group Y above.

Most preferably, spacer 2 consists of the functional group Y. In particular, functional group Y comprises a group —C(=O)—. According to one preferred example, Y is derived from —C(=O)—OH. Other preferred examples for groups Ar can be taken from the particular Examples herein.

In particularly preferred embodiments of the invention the following groups are preferred for Ar:

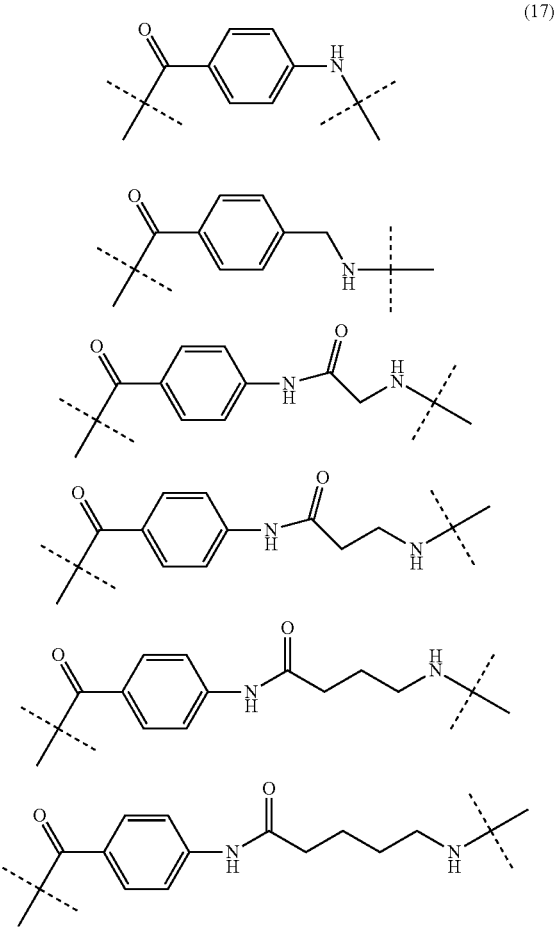

(17)

-continued

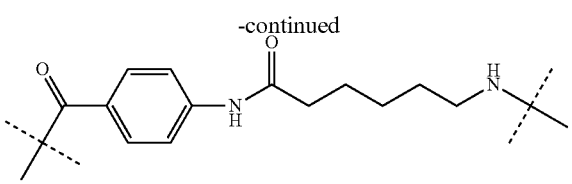

with the following group being especially preferred:

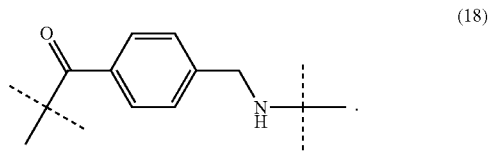

(18)

Thus, the present invention also relates to a compound as described above, wherein Ar is a group having the formula:

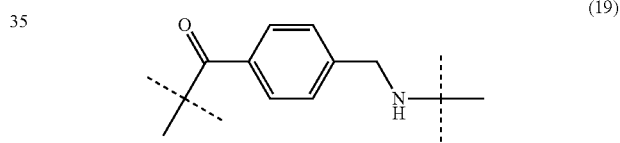

(19)

Thus, the present invention also relates to a compound having the following structure:

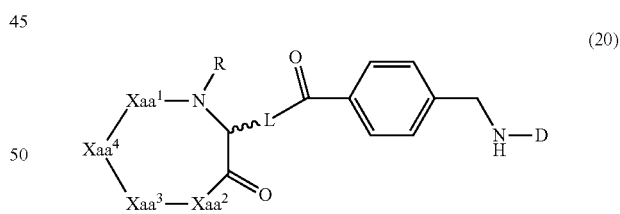

(20)

The compound D:

The compound D may also be referred to herein as "D" or "further compound D".

In one aspect of the invention, D comprises, preferably is a combination of an organic complexation agent and a radioactive label. In certain preferred embodiments, the radionuclide is a Lu radionuclide, an Y-radionuclide, an In radionuclide, an Ga radionuclide, a Bi radionuclide, a Cu radionuclide, an Zr radionuclide, a Tc radionuclide, a Tb radionuclide, a Ho radionuclide or an Al $^{18}F^{2+}$ ion.

Combinations are preferably selected from Ga with DOTA, Ga with NODASA, Ga with NODAGA, Ga with NOTA, Ga with NOPO, Ga with TRAP and in particular selected from Ga with DOTA, NOPO, TRAP, DOTAGA and NOPO.

Furthermore, combinations are preferably selected from Lu with DOTA, DOTPI, DOT-AGA, DTPA and CHX-DTPA.

Furthermore, combinations are preferably selected from Y with DOTA, DOTPI, DOT-AGA, DTPA and CHX-DTPA.

Furthermore, combinations are preferably selected from In with DOTA, DOTPI, DOT-AGA, DTPA and CHX-DTPA.

Furthermore, combinations are preferably selected from Bi with DOTA, DOTPI, DOTP, DOTAGA, DTPA and CHX-DTPA.

Furthermore, combinations are preferably selected from Cu with NOTA, TRAP, NOPO, DOTPI and NODAGA.

Furthermore, combinations are preferably selected from Zr with DFO.

Furthermore, combinations are preferably selected from Tc with DTPA, HYNIC and $MAG_3$.

Furthermore, combinations are preferably selected from Tb with DOTA, DOTPI, DOT-AGA, DTPA and CHX-DTPA.

Furthermore, combinations are preferably selected from Ho with DOTA, DOTPI, DOT-AGA, DTPA and CHX-DTPA.

Furthermore, combinations are preferably selected from $Al^{18}F$ with functionalized NODA, such as NH2-MPAA-NODA or NCS-MP-NODA, or NODAGA, DOTA or CHX-DTPA.

Preferably, the complexation agent being covalently bound to Ar.

In another aspect of the invention, D comprises, preferably is a radioactive and detectable label, organic complexation agent or active substance. Accordingly, D may be selected from the group consisting of radioactive and detectable labels, organic complexation agents and active substances. In certain preferred embodiments, D comprises, preferably is a radioactive label. In certain preferred embodiments, D comprises, preferably is an organic complexation agent. In certain preferred embodiments, D comprises, preferably is an active substance. In certain embodiments of this aspect, —Ar-D, particularly-L-Ar-D, especially the compound of formula (I), comprise a $Al^{18}F^{2+}$ ion as radioactive label.

In an additional aspect of the invention, D comprises, preferably is a combination of an organic complexation agent and a metal ion or the $AlF^{2+}$ ion, wherein said metal ions and $AlF^{2+}$ ions are not radioactive, such as e.g Ga, Lu, Y etc or any non-radioactive isotope. In an additional aspect of the invention, D comprises, preferably is a combination of an organic complexation agent and a radioisotope suitable for molecular imaging purposes, $^{68}$Ga, $^{111}$In. $^{99m}$Tc, $^{64}$Cu etc. or $Al^{18}F^{2+}$. This is especially the case for those aspects of the invention, where Xaal is labeled or comprises of a radioactive label.

In preferred embodiments of the invention, the organic complexation agent is selected from the group consisting of NODASA, NODAGA, TETA, TRITA, TRAP, DPTA, CHX-DTPA EDTA, CDTA, CPTA, DOTP, DOTPI, EGTA, HBED, TTHA, DTPA, DOTA, DOTAGA, NOTA, HP-DOA3, CBTE2a, TE2A, TMT, DPDP, HYNIC, DFO, HEDTA, NOPO. MAG3, NCS-MP-NODA, NH2-MPAA-NODA, and particularly from DOTA, DOTAGA, NOTA, DTPA, CHX-DTPA, NODA and functionalized NODA, TRAP, DOT-PI, DOTP, NOPO and TETA.

In preferred embodiments of the invention the detectable label is a radionuclide selected from the group consisting of $^{11}$C, $^{18}$F, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$CU, $^{66}$Ga, $^{68}$Ga, $^{67}$Ga, $^{72}$As, $^{77}$As, $^{75}$Br, $^{76}$Br, $^{77}$Br, $^{82}$Br, $^{89}$Zr, $^{90}$Y, $^{94m}$Tc, $^{99}$Tc, $^{97}$Ru, $^{105}$Rh, $^{109}$Pd, $^{111}$Ag, $^{110m}$In, $^{111}$In, $^{113m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $_{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $_{-188}$Re, $^{191}$Pt, $^{197}$Hg, $^{198}$Au, $^{199}$Au, $^{201}$Tl, $^{203}$Pb, $^{211}$At, $_{212}$Bi and $^{213}$Bi, and $^{225}$Ac; particularly from the group consisting of $^{18}$F, $^{68}$Ga, $^{64}$Cu, $^{89}$Zr, $^{90}$Y, $^{99m}$Tc, $^{111}$In, $^{123}$I, $^{124}$I, $^{131}$I, $^{177}$Lu; especially from the group consisting of $^{18}$F, $^{68}$Ga $^{99m}$Tc, $^{111}$In, $^{123}$I, $^{90}$Y, $^{177}$Lu, $^{212}$Bi and $^{225}$Ac "Active substances" are well-known to the skilled person. The term "active substance" as used in the context of the present invention preferably refers to substances selected from the group consisting of cytotoxic agents, lipids, sugars, sugar conjugates, sugar derivatives, proteins and combinations thereof. In certain preferred embodiment, the active substance is a cytotoxic agent. In certain embodiments, the active substance is a radionuclide, particularly a radionuclide disclosed herein. In other preferred embodiments, the active substance is selected from sugars, sugar conjugates, sugar derivatives, proteins and combinations thereof, or is a lipid.

"Cytotoxic agents", which may also be referred to herein as "cytotoxic moieties" or "cytotoxic compounds", are well known to the skilled person. They include the cytotoxic compounds disclosed hereinbelow, particularly the radionuclides disclosed hereinbelow. Also lipids, sugars, sugar conjugates, sugar derivatives, and proteins, all of which are well-known known to the skilled person, are not particularly limited. Preferably, the protein is an enzyme or an antibody.

In preferred embodiments, particularly for endoradiotherapeutic purposes, compounds of the invention comprise a compound D which comprises a radioactive label, preferably is a radioisotope selected from the group consisting of $^{114m}$In, $^{186}$Re, $^{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{195m}$Pt, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{103m}$Rh, $^{111}$Ag, $^{124}$I, $^{131}$I, and $^{211}$At, $^{212}$Bi, $^{225}$Ac; more preferably from the group consisting of $^{90}$Y, $^{131}$I, $^{177}$Lu and $^{212}$Bi, $^{225}$Ac; and most preferably from the group consisting of $^{90}$Y, $^{177}$Lu, $^{212}$Bi and $^{225}$Ac.

Thus, the present invention also refers to a compound of formula (I) as described above, wherein D, comprises, preferably is, a radionuclide selected from the group consisting of $^{114m}$In, $^{186}$Re, $_{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{195m}$Pt, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh,$^{103m}$Rh, $^{111}$Ag, $^{124}$I, $^{131}$I, and $^{211}$At, $^{212}$Bi, $^{225}$Ac: more preferably from the group consisting of $^{90}$Y, $^{131}$I, $^{177}$Lu, and $^{212}$Bi, $^{225}$Ac; and most preferably from the group consisting of $^{90}$Y, $^{177}$Lu, $^{212}$Bi and $^{225}$Ac.

The Term Detectable Label:

The term "detectable label" as used herein refers to any label which provides directly or indirectly a detectable signal.

For example, the label may be detectable without the addition of further reagents, such as by means of an output of detectable electromagnetic radiation or other nuclear radiation from the label itself, or as a result of its magnetic or paramagnetic properties. The label may also be detectable upon addition of one or more further reagent(s). A person skilled in the art will readily select said further reagent(s) in dependence of the label.

The detectable label is preferably a moiety being suitable for imaging and/or assaying, for example, for identifying, diagnosing, evaluating, detecting and/or quantitating, in vivo or in vitro, in particular for in vivo or in vitro detection via radioscintigraphy, magnetic resonance imaging (MRI), chemiluminescence, near infrared luminescence, gamma imaging, magnetic resonance spectroscopy, fluorescence spectroscopy, SPECT, computed tomography (CT scan), positron emission tomography (PET) or methods for optical tomography.

Suitable detectable labels include, for example, radiolabels, such as radioisotopes, radionuclides, isotopes, enzymes, enzyme substrates or co-factors, enzyme inhibitors, magnetic or paramagnetic moieties or particles, fluorescent groups, biotin (in conjunction with streptavidin complexation), radiolabels in conjugation with organic complexation agents, photoaffinity groups, or enzymes and substrates for bioluminescent imaging, such as firefly luciferase and L-luciferin as the substrate, or combinations thereof.

"Fluorescent labels" or "fluorescent groups" include, but are not limited to NBD (7-nitro-1,2,3-benzoxadiazole), Texas red, phycoerythrin (PE), Cy5, Cy 5.5, cytochrome c, and fluoresceine isothiocyanate (FITC).

"Magnetic or paramagnetic moieties or particles" include, but are not limited to MR contrast agents, e.g. chelates of paramagnetic, ferromagnetic, or diamagnetic metal ions, or magnetic particles. One specific example for a paramagnetic label is gadolinium (Gd) and chelates thereof.

According to preferred embodiments of the present invention, in case the compound of formula (I) comprises a detectable label, said detectable label is preferably a radiolabel or an organic complexation agent or a combination of a radiolabel and an organic complexation agent thereof.

In case the compound D, particularly the detectable label, comprises, preferably is a radiolabel, label, said radiolabel is preferably a radionuclide selected from the group consisting of $^{11}$C, $^{18}$F, $_{47}$Sc, $^{51}$Cr, $^{52m}$Mn, $^{58}$Co, $^{52}$Fe, $^{56}$Ni, $^{57}$Ni, $^{62}$Cu, $^{64}$Cu, $_{67}$Cu, $^{66}$Ga, $^{68}$Ga, $^{67}$Ga, $_{72}$As, $^{77}$As, $^{75}$Br, $^{76}$Br, $^{77}$Br, $_{82}$Br, $^{89}$Zr, $^{89}$Y, $^{90}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $_{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$An, $^{199}$Au, $^{201}$Tl, $_{203}$Pb, $^{211}$At, $^{212}$Bi and $^{225}$Ac; and more preferably from the group consisting of $^{18}$F, $^{68}$Ga, $^{67}$Ga, $^{89}$Zr, $^{89}$Y, $^{90}$Y, $^{99m}$Tc, $^{111}$In, $^{123}$I, $^{124}$I, $^{131}$I, $^{177}$Lu; and most preferably from the group consisting of $^{18}$F, $^{67}$Ga, $^{68}$Ga, $^{99m}$Tc, $^{111}$In, $^{123}$I, and $^{177}$Lu.

"Radionuclide" and "radioisotope" are used interchangeably herein. A "radionuclide" as used herein may e.g. be a radiolabel or a cytotoxic moiety.

In case the compound of formula (I) comprises a radionuclide, said radionuclide is preferably complexed by an organic complexation agent, said complexation agent being attached to the moiety Ar as described above.

The Organic Complexation Agent

The term "organic complexation agent" refers to a chelating agent, preferably capable of complexing at least one radionuclide.

As regards complexation agents suitable for the present invention, reference is made to WO 2009/109332, pages 9 to 14, and the respective metal chelators disclosed therein as well as to WO 97/31657.

According to a preferred embodiment of the present invention, the organic complexation agent is a chelating agent like CBTE2, CDTA, CHX-DTPA, CPTA, DFO, DO2A, DOTA, DOTPI, DOTP, DPDP, EDTA, EGTA, HBED, HEDTA, HP-DOA3, HYNIC, MAG3, NCS-MP-NODA, NH2-MPAA-NODA, NODASA, NODAGA, NODA, NOPO, NOTA, TE2A, TETA, TMT, TRAP, TRITA or TTHA. Those chelating agents are well known to those skilled in the art for radiopharmaceuticals and radiodiagnosticals.

CBTE2a stands for bis(carboxymethyl)-1,4,8,11-tetraazabicyclo[6.6.2]hexadecane,

CDTA stands for cyclohexyl 1,2-diamine tetraacetic acid,

CHX-DTPA stands for cyclohexyl-diethylenetriaminepentaacetic acid

CPTA stand for [4-(1,4,8,11-tetraazacyclotetradec-1-yl)-methyl benzoic acid] hydrochloride, DFO stands for N'-[5-[acetyl(hydroxy)amino]pentyl]-N-[5-[[4-[5-aminopentyl(hydroxy) amino]-4-oxobutanoyl] amino]pentyl]-N-hydroxybutanediamide, DO2A stands for 4,11-bis(carboxymethyl)-1,4,8,11-tetraazabicyclo[6.6.2]hexadecane.

DOTA stands for 1,4,7,10-tetracyclododecane-N,N',N'', N''', tetraacetic acid,

DOTPI stands for 1,4,7,10-tetraazacyclododecane-1,4,7, 10-tetrakis[methylene(2-carboxyethyl)phosphinic acid]

DOTP stands for 1,4,7,10-tetraazacyclododecane-1,4,7, 10-tetrakis[methylene(2-carboxyethyl)phosphonic acid]

DPDP stands for (N,N-dipyridoxylethylenediamine-N,N-diacetate-5,5'-bis(phosphate), DTPA stands for dietehylenetriaminepentaacetic acid, EDTA stands for ethylenediamine-N,N'-tetraacetic acid, EGTA stands ethyleneglycol-O,O-bis (2-aminoethyl), N, N, N', N' tetraacetic acid, HBED stands for N, N-bis (hydroxybenzyl)-ethylenediamine-N,N'-diacetic acid, HEDTA stands for hydroxyethylediamine triacetic acid, HP-DOA3 stands for 1-(p-nitrobenzyl)-1,4,710-tetraazacyclodecane-4,7,10-triacetate, HYNIC stands for 6-hydrazinyl-N-methylpyridine-3-carboxamide, MAG3 stand for mercaptoacetyltriglycine NCS-MP-NODA stands for 2,2'47-(4-isothiocyanatobenzyl)-1,4,7-triazonane-1,4-diyl)diacetic acid NH2-MPAA-NODA stands for 2,2'-(7-(4-(24(2-aminoethypamino)-2-oxoethyl)benzyl)-1,4,7-tri-azonane-1,4-diyl) diacetic acid NODASA stands for 1,4,7-Triazacyclononane-1-succinic acid-4,7-diacetic acid, NODAGA stands for 1-(1-Carboxy-3-carboxypropyl)-4, 7-(carbooxy)-1,4,7-triazacyclo-nonane, NODA (1,4,7-triazonane-1,4-diyl)diacetic acid NOPO stands for 1,4,7-triazacyclononane-1,4-bis[methylene(hydroxymethyl)phosphinic acid]-7- [methylene(2-carboxyethyl)phosphinic acid], NOTA stands for 1,4,7-triazacyclononanetriacetic acid, TE2A stands for 4,11-bis(carboxymethyl)-1,4,8,11-tetraazabicyclo[6.6.2]hexadecane, TETA stands for 1,4,8,11-tetraazacyclododecane-1,4,8, 11-tetraacetic acid, TMT stands for terpyridine-bis(methylenaminetetraacetic acid, TRAP stands for 1,4,7-triazacyclononane-1,4,7-tris(methylenephosphinic acid)

TRITA stands for 1,4,7,10-tetraazacyclotridecane-N,N', N'',N'''-tetraacetic acid, TTHA stands for triethylene tetraamine hexaacetic acid.

According to a further embodiment of the present invention, the organic complexation agent is a macrocyclic chelating agent, for example, a porphyrin-like molecule, a pentaazamacrocycle as described by Zhang et al., 1998, a phthalocyanine, a crown ether, e.g. a nitrogen crown ether such as the sepulchrates, or crypates.

According to an alternative embodiment, the organic complexation agent is a $N_tS_{(4-t)}$ chelating agents, such as the chelating agents described on page 8 to page 9 in WO 97/31657.

Examples of suitable chelators are further described in the international patent application WO 89/07456, such as unsubstituted or substituted 2-imino-thiolanes and 2-iminothiacyclohexanes, in particular 2-imino-4-mercaptomethylthiolane.

According to a preferred embodiment of the present invention, the organic complexation agent is selected from the group consisting of DOTA, DOTP, DOTPI, NOTA, NODA, functionalized NODA, NOPO, CHX-DTPA, DTPA, TRITA, TETA, TRAP, DTPA, HYN—IC, MAG3 and CBTE2a, more preferably DOTA, DOTP DOTPI, NOTA, functionalized NODA, CHX-DTPA, DTPA, MAG3 and TETA.

Thus, the present invention also relates to a compound, as described above, wherein the organic complexation agent is selected from the group consisting of DOTA, DOTP, DOTPI, NOTA, NODA, functionalized NODA, NODASA, NODAGA, NOPO, CHX-DTPA, DTPA, TRITA, TETA, TRAP, DTPA, HYNIC, MAG3 and CBTE2a, more preferably DOTA, DOTP, DOTPI, NOTA, functionalied NODA, CHX-DTPA, DTPA, MAG3 and TETA.

More preferably, the organic complexation agent is DOTA, DOTAGA, DOTP, CHX-DTPA, MAG3, NODA and functionalized NODA, TRAP, DOTPI and NOPO.

wherein the chelators are preferably coupled via one of its carboxy functions to the moiety Ar.

Thus, the present invention also relates to a compound, as described above, wherein D comprises an organic complexation agent, and wherein the organic complexation agent is selected from the group consisting of like NODASA, NODAGA, TETA, TRITA, DTPA, EDTA, CDTA, CPTA, EGTA, HBED, TTHA, DTPA, DOTA, NOTA, HP-DOA3, CBTE2a, TE2A, DPDP, HYNIC, DFO and HEDTA, in particular wherein the organic complexation agent is selected from the group consisting of DOTA, NOTA, TRITA, TETA, DTPA, HYNIC and CBTE2a, more preferably DOTA, NOTA, DTPA, and TETA, more preferably DOTA, NOTA and DTPA, most preferably DOTA.

In particularly preferred embodiments, D comprises, especially consists of a combination of an organic complexation agent and a radionuclide. Suitable such combinations are well-known to the skilled person. In particularly preferred embodiments, D comprises, in particular is, a combination of a radionuclide and a complexation agent, with the complexation agent being covalently bound to Ar and the radionuclide being complexed by the complexation agent.

In the following tables I to IV, preferred structures of the invention are mentioned by way of example, wherein the following abbreviations are used:

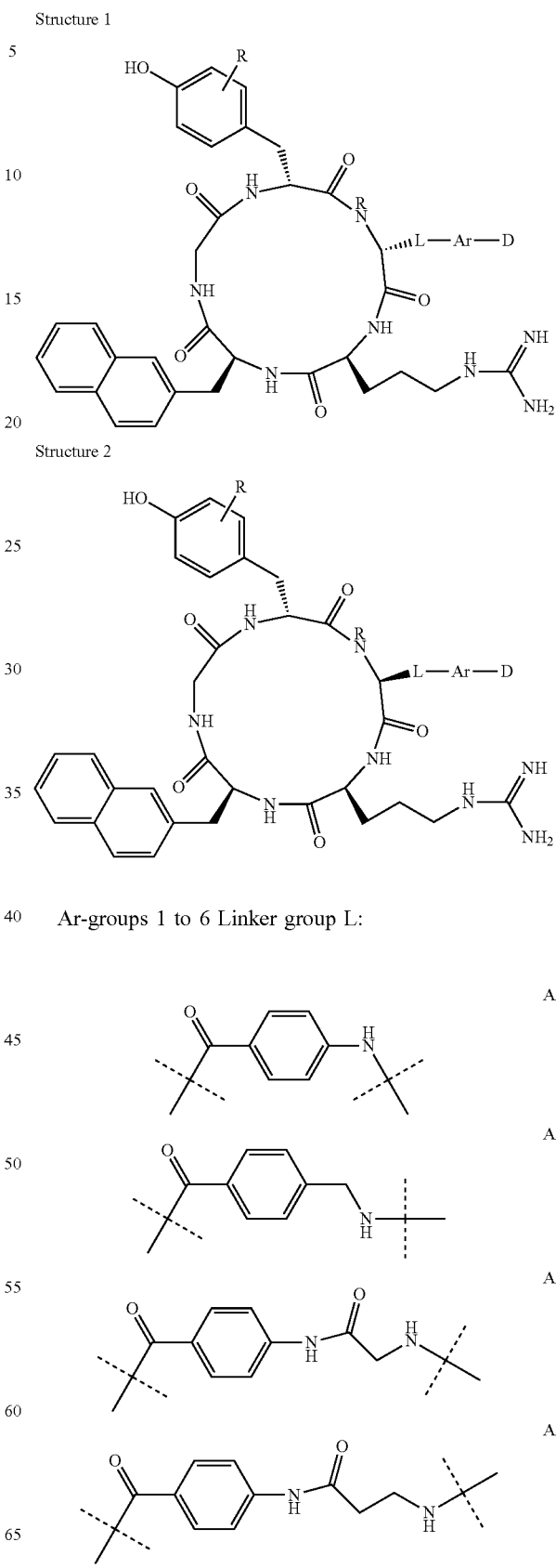

(21)

Structure 1

Structure 2

Ar-groups 1 to 6 Linker group L:

Ar1

Ar2

Ar3

Ar4

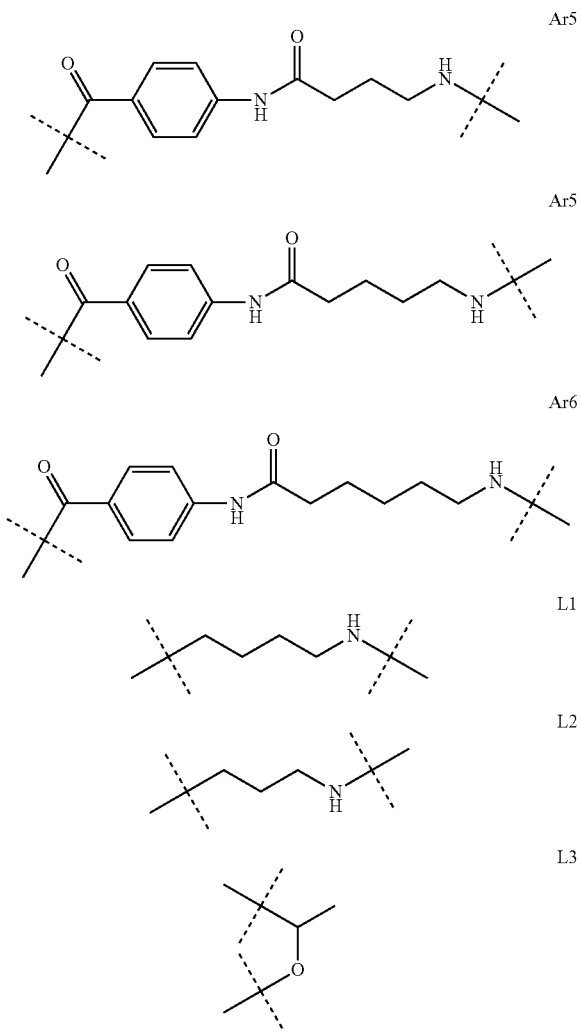

Particularly preferred compounds of the present invention are selected from the group of compounds consisting of:

TABLE 1

| No. | Abbreviation |
|---|---|
| | 3-iodo-y-compounds |
| 1 | (3-iodo-y)-orn'(DOTA)RNalG |
| 2 | (3-iodo-y)-orn'(ABS, DOTA)RNalG |
| 3 | (3-iodo-y)-orn'(ABS, G, DOTA)RNalG |
| 4 | (3-iodo-y)-orn'(ABS, betaAla, DOTA)RNalG |
| 5 | (3-iodo-y)-orn'(ABS, Ahx, DOTA)RNalG |
| 6 | (3-iodo-y)-orn'(ABS, AVS, DOTA)RNalG |
| 7 | (3-iodo-y)-orn'(AMBS, DOTA)RNalG |
| 8 | (3-iodo-y)-orn'(AVS, AVS, DOTA)RNalG |
| 9 | (3-iodo-y)-orn'(G, Trigas, DOTA)RNalG |
| | Compounds with Gallium as (radio)metal |
| 10 | (3-iodo-y)-orn'(DOTA, Ga)RNalG |
| 11 | (3-iodo-y)-orn'(ABS, DOTA, Ga)RNalG |
| 12 | (3-iodo-y)-orn'(ABS, G, DOTA, Ga)RNalG |
| 13 | (3-iodo-y)-orn'(ABS, betaAla, DOTA, Ga)RNalG |
| 14 | (3-iodo-y)-orn'(ABS, Ahx, DOTA, Ga)RNalG |
| 15 | (3-iodo-y)-orn'(ABS, AVS, DOTA, Ga)RNalG |
| 16 | (3-iodo-y)-orn'(AMBS, DOTA, Ga)RNalG |
| 17 | (3-iodo-y)-orn'(AVS, AVS, DOTA, Ga)RNalG |
| 18 | (3-iodo-y)-orn'(G, Trigas, DOTA, Ga)RNalG |

TABLE 1-continued

| No. | Abbreviation |
|---|---|
| | Compounds with Lutetium (radio)metal |
| 19 | (3-iodo-y)-orn'(DOTA, Lu)RNalG |
| 20 | (3-iodo-y)-orn'(ABS, DOTA, Lu)RNalG |
| 21 | (3-iodo-y)-orn'(ABS, G, DOTA, Lu)RNalG |
| 22 | (3-iodo-y)-orn'(ABS, betaAla, DOTA, Lu)RNalG |
| 23 | (3-iodo-y)-orn'(ABS, Ahx, DOTA, Lu)RNalG |
| 24 | (3-iodo-y)-orn'(ABS, AVS, DOTA, Lu)RNalG |
| 25 | (3-iodo-y)-orn'(AMBS, DOTA, Lu)RNalG |
| 26 | (3-iodo-y)-orn'(AVS, AVS, DOTA, Lu)RNalG |
| 27 | (3-iodo-y)-orn'(G, Trigas, DOTA, Lu)RNalG |
| | Compounds with Yttrium as (radio)metal |
| 28 | (3-iodo-y)-orn'(DOTA, Y)RNalG |
| 29 | (3-iodo-y)-orn'(ABS, DOTA, Y)RNalG |
| 30 | (3-iodo-y)-orn'(ABS, G, DOTA, Y)RNalG |
| 31 | (3-iodo-y)-orn'(ABS, betaAla, DOTA, Y)RNalG |
| 32 | (3-iodo-y)-orn'(ABS, Ahx, DOTA, Y)RNalG |
| 33 | (3-iodo-y)-orn'(ABS, AVS, DOTA, Y)RNalG |
| 34 | (3-iodo-y)-orn'(AMBS, DOTA, Y)RNalG |
| 35 | (3-iodo-y)-orn'(AVS, AVS, DOTA, Y)RNalG |
| 36 | (3-iodo-y)-orn'(G, Trigas, DOTA, Y)RNalG |
| | Compounds with Indium as (radio)metal |
| 37 | (3-iodo-y)-orn'(DOTA, In)RNalG |
| 38 | (3-iodo-y)-orn'(ABS, DOTA, In)RNalG |
| 39 | (3-iodo-y)-orn'(ABS, G, DOTA, In)RNalG |
| 40 | (3-iodo-y)-orn'(ABS, betaAla, DOTA, In)RNalG |
| 41 | (3-iodo-y)-orn'(ABS, Ahx, DOTA, In)RNalG |
| 42 | (3-iodo-y)-orn'(ABS, AVS, DOTA, In)RNalG |
| 43 | (3-iodo-y)-orn'(AMBS, DOTA, In)RNalG |
| 44 | (3-iodo-y)-orn'(AVS, AVS, DOTA, In)RNalG |
| 45 | (3-iodo-y)-orn'(G, Trigas, DOTA, In)RNalG |
| | Compounds with Bismuth as (radio)metal |
| 46 | (3-iodo-y)-orn'(DOTA, Bi)RNalG |
| 47 | (3-iodo-y)-orn'(ABS, DOTA, Bi)RNalG |
| 48 | (3-iodo-y)-orn'(ABS, G, DOTA, Bi)RNalG |
| 49 | (3-iodo-y)-orn'(ABS, betaAla, DOTA, Bi)RNalG |
| 50 | (3-iodo-y)-orn'(ABS, Ahx, DOTA, Bi)RNalG |
| 51 | (3-iodo-y)-orn'(ABS, AVS, DOTA, Bi)RNalG |
| 52 | (3-iodo-y)-orn'(AMBS, DOTA, Bi)RNalG |
| 53 | (3-iodo-y)-orn'(AVS, AVS, DOTA, Bi)RNalG |
| 54 | (3-iodo-y)-orn'(G, Trigas, DOTA, Bi)RNalG |
| | Compounds with AlF as "ion" for complexation |
| 55 | (3-iodo-y)-orn'(DOTA, AlF)RNalG |
| 56 | (3-iodo-y)-orn'(ABS, DOTA, AlF)RNalG |
| 57 | (3-iodo-y)-orn'(ABS, G, DOTA, AlF)RNalG |
| 58 | (3-iodo-y)-orn'(ABS, betaAla, DOTA, AlF)RNalG |
| 59 | (3-iodo-y)-orn'(ABS, Ahx, DOTA, AlF)RNalG |
| 60 | (3-iodo-y)-orn'(ABS, AVS, DOTA, AlF)RNalG |
| 61 | (3-iodo-y)-orn'(AMBS, DOTA, AlF)RNalG |
| 62 | (3-iodo-y)-orn'(AVS, AVS, DOTA, AlF)RNalG |
| 63 | (3-iodo-y)-orn'(G, Trigas, DOTA, AlF)RNalG |
| | Compounds with Actinium as (radio)metal |
| 64 | (3-iodo-y)-orn'(DOTA, Ac)RNalG |
| 65 | (3-iodo-y)-orn'(ABS, DOTA, Ac)RNalG |
| 66 | (3-iodo-y)-orn'(ABS, G, DOTA, Ac)RNalG |
| 67 | (3-iodo-y)-orn'(ABS, betaAla, DOTA, Ac)RNalG |
| 68 | (3-iodo-y)-orn'(ABS, Ahx, DOTA, Ac)RNalG |
| 69 | (3-iodo-y)-orn'(ABS, AVS, DOTA, Ac)RNalG |
| 70 | (3-iodo-y)-orn'(AMBS, DOTA, Ac)RNalG |
| 71 | (3-iodo-y)-orn'(AVS, AVS, DOTA, Ac)RNalG |
| 72 | (3-iodo-y)-orn'(G, Trigas, DOTA, Ac)RNalG |
| | 3-methyl-y-compounds |
| 73 | (3-methyl-y)-orn'(DOTA)RNalG |
| 74 | (3-methyl-y)-orn'(ABS, DOTA)RNalG |
| 75 | (3-methyl-y)-orn'(ABS, G, DOTA)RNalG |
| 76 | (3-methyl-y)-orn'(ABS, betaAla, DOTA)RNalG |
| 77 | (3-methyl-y)-orn'(ABS, Ahx, DOTA)RNalG |
| 78 | (3-methyl-y)-orn'(ABS, AVS, DOTA)RNalG |
| 79 | (3-methyl-y)-orn'(AMBS, DOTA)RNalG |
| 80 | (3-methyl-y)-orn'(AVS, AVS, DOTA)RNalG |
| 81 | (3-methyl-y)-orn'(G, Trigas, DOTA)RNalG |

TABLE 1-continued

| No. | Abbreviation |
|---|---|
| | Compounds with Gallium as (radio)metal |
| 82 | (3-methyl-y)-orn'(DOTA, Ga)RNalG |
| 83 | (3-methyl-y)-orn'(ABS, DOTA, Ga)RNalG |
| 84 | (3-methyl-y)-orn'(ABS, G, DOTA, Ga)RNalG |
| 85 | (3-methyl-y)-orn'(ABS, betaAla, DOTA, Ga)RNalG |
| 86 | (3-methyl-y)-orn'(ABS, Ahx, DOTA, Ga)RNalG |
| 87 | (3-methyl-y)-orn'(ABS, AVS, DOTA, Ga)RNalG |
| 88 | (3-methyl-y)-orn'(AMBS, DOTA, Ga)RNalG |
| 89 | (3-methyl-y)-orn'(AVS, AVS, DOTA, Ga)RNalG |
| 90 | (3-methyl-y)-orn'(G, Trigas, DOTA, Ga)RNalG |
| | Compounds with Lutetium as (radio)metal |
| 91 | (3-methyl-y)-orn'(DOTA, Lu)RNalG |
| 92 | (3-methyl-y)-orn'(ABS, DOTA, Lu)RNalG |
| 93 | (3-methyl-y)-orn'(ABS, G, DOTA, Lu)RNalG |
| 94 | (3-methyl-y)-orn'(ABS, betaAla, DOTA, Lu)RNalG |
| 95 | (3-methyl-y)-orn'(ABS, Ahx, DOTA, Lu)RNalG |
| 96 | (3-methyl-y)-orn'(ABS, AVS, DOTA, Lu)RNalG |
| 97 | (3-methyl-y)-orn'(AMBS, DOTA, Lu)RNalG |
| 98 | (3-methyl-y)-orn'(AVS, AVS, DOTA, Lu)RNalG |
| 99 | (3-methyl-y)-orn'(G, Trigas, DOTA, Lu)RNalG |
| | Compounds with Yttrium as (radio)metal |
| 100 | (3-methyl-y)-orn'(DOTA, Y)RNalG |
| 101 | (3-methyl-y)-orn'(ABS, DOTA, Y)RNalG |
| 102 | (3-methyl-y)-orn'(ABS, G, DOTA, Y)RNalG |
| 103 | (3-methyl-y)-orn'(ABS, betaAla, DOTA, Y)RNalG |
| 104 | (3-methyl-y)-orn'(ABS, Ahx, DOTA, Y)RNalG |
| 105 | (3-methyl-y)-orn'(ABS, AVS, DOTA, Y)RNalG |
| 106 | (3-methyl-y)-orn'(AMBS, DOTA, Y)RNalG |
| 107 | (3-methyl-y)-orn'(AVS, AVS, DOTA, Y)RNalG |
| 108 | (3-methyl-y)-orn'(G, Trigas, DOTA, Y)RNalG |
| | Compounds with Indium as (radio)metal |
| 109 | (3-methyl-y)-orn'(DOTA, In)RNalG |
| 110 | (3-methyl-y)-orn'(ABS, DOTA, In)RNalG |
| 111 | (3-methyl-y)-orn'(ABS, G, DOTA, In)RNalG |
| 112 | (3-methyl-y)-orn'(ABS, betaAla, DOTA, In)RNalG |
| 113 | (3-methyl-y)-orn'(ABS, Ahx, DOTA, In)RNalG |
| 114 | (3-methyl-y)-orn'(ABS, AVS, DOTA, In)RNalG |
| 115 | (3-methyl-y)-orn'(AMBS, DOTA, In)RNalG |
| 116 | (3-methyl-y)-orn'(AVS, AVS, DOTA, In)RNalG |
| 117 | (3-methyl-y)-orn'(G, Trigas, DOTA, In)RNalG |
| | Compounds with Bismuth as (radio)metal |
| 118 | (3-methyl-y)-orn'(DOTA, Bi)RNalG |
| 119 | (3-methyl-y)-orn'(ABS, DOTA, Bi)RNalG |
| 120 | (3-methyl-y)-orn'(ABS, G, DOTA, Bi)RNalG |
| 121 | (3-methyl-y)-orn'(ABS, betaAla, DOTA, Bi)RNalG |
| 122 | (3-methyl-y)-orn'(ABS, Ahx, DOTA, Bi)RNalG |
| 123 | (3-methyl-y)-orn'(ABS, AVS, DOTA, Bi)RNalG |
| 124 | (3-methyl-y)-orn'(AMBS, DOTA, Bi)RNalG |
| 125 | (3-methyl-y)-orn'(AVS, AVS, DOTA, Bi)RNalG |
| 126 | (3-methyl-y)-orn'(G, Trigas, DOTA, Bi)RNalG |
| | Compounds with AlF as "ion" for complexation |
| 127 | (3-methyl-y)-orn'(DOTA, AlF)RNalG |
| 128 | (3-methyl-y)-orn'(ABS, DOTA, AlF)RNalG |
| 129 | (3-methyl-y)-orn'(ABS, G, DOTA, AlF)RNalG |
| 130 | (3-methyl-y)-orn'(ABS, betaAla, DOTA, AlF)RNalG |
| 131 | (3-methyl-y)-orn'(ABS, Ahx, DOTA, AlF)RNalG |
| 132 | (3-methyl-y)-orn'(ABS, AVS, DOTA, AlF)RNalG |
| 133 | (3-methyl-y)-orn'(AMBS, DOTA, AlF)RNalG |
| 134 | (3-methyl-y)-orn'(AVS, AVS, DOTA, AlF)RNalG |
| 135 | (3-methyl-y)-orn'(G, Trigas, DOTA, AlF)RNalG |
| | Compounds with Actinium as (radio)metal |
| 136 | (3-methyl-y)-orn'(DOTA, Ac)RNalG |
| 137 | (3-methyl-y)-orn'(ABS,DOTA, Ac)RNalG |
| 138 | (3-methyl-y)-orn'(ABS, G, DOTA, Ac)RNalG |
| 139 | (3-methyl-y)-orn'(ABS, betaAla, DOTA, Ac)RNalG |
| 140 | (3-methyl-y)-orn'(ABS, Ahx, DOTA, Ac)RNalG |
| 141 | (3-methyl-y)-orn'(ABS, AVS, DOTA, Ac)RNalG |
| 142 | (3-methyl-y)-orn'(AMBS, DOTA, Ac)RNalG |
| 143 | (3-methyl-y)-orn'(AVS, AVS, DOTA, Ac)RNalG |
| 144 | (3-methyl-y)-orn'(G, Trigas, DOTA, Ac)RNalG |

Pharmaceutically Acceptable Salt

As described above, the compound of the present invention can be formulated as pharmaceutically acceptable salt. Typical pharmaceutically acceptable salts include those salts prepared by reaction of the compounds of the present invention with a pharmaceutically acceptable mineral or organic acid or an organic or inorganic base. Such salts are known as acid addition and base addition salts. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, trfluoroacetic acid and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid. Salts of amine groups may also comprise quarternary ammonium salts in which the amino nitrogen carries a suitable organic group such as an alkyl, alkenyl, alkynyl, or aralkyl moiety. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt folins are particularly preferred. It should be recognized that the particular counterion forming a part of any salt of this invention is usually not of a critical nature, so long as the salt as a whole is pharmacologically acceptable and as long as the counterion does not contribute undesired qualities to the salt as a whole. The term acceptable salt encompasses also pharmaceutically acceptable solvates of the compounds of the invention, wherein the compound combines with a solvent such as water, methanol, ethanol or acetonitrile to form a pharmaceutically acceptable solvate such as the corresponding hydrate, methanolate, ethanolate or acetonitrilate.

In an even further aspect, the present invention relates to a compound, or a pharmaceutically acceptable salt thereof, having a structure according to folinula (22)

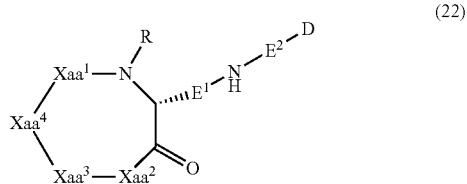

(22)

wherein $Xaa^1$ to $Xaa^4$ are independently of each other, an optionally N-alkylated natural or unnatural amino acid, R is H or methyl, $E^1$ is —$(CH_2)_e$— with e being selected from 1, 2 and 3, particularly 3, $E^2$ is a spacing moiety composed of 0 to 20 units of bifunctional linkers, and D comprises, preferably is i) a combination of an organic complexation agent and a radioactive or detectable label; or ii) a radioactive or detectable label, an organic complexation agent or an active substance, said active substance particularly being selected from cytotoxic agents, lipids, sugars, sugar conjugates, sugar derivatives, proteins and combinations thereof, with the proviso that- $E^1$-NH-$E^2$-D does not comprise a $^{18}$F-benzoyl residue.

Said 0 to 20 bifunctional linkers may be arranged in any conceivable order, as long as they together form a spacing moiety that is capable of linking —NH— to D.

According to this aspect, each of $Xaa^1$ to $Xaa^4$, R, D, and preferably also the bifunctional linker, as well as their respective preferred embodiments, are as defined herein above and below. Moreover, according to this aspect, D is preferably selected from DOTA, DOT-AGA, CHX-DTPA, NOGAGA, NODA and functionalized NODA, DOTP or DOTPI and a combination of these chalators and a radionuclide or the $AlF^{2+}$-ion.

Preferably, $E^2$ is selected from —(C=O)—$CH_2$—NH—, —(C=O)—$(CH_2)_2$—NH—, —(C=O)—$(CH_2)_3$—NH—, —(C=O)—$(CH_2)_4$—NH—C(=O)—$(CH_2)_4$—NH—, —C(=O)—$CH_2$—O—$(CH_2)_2$—O—$(CH_2)_2$—NH— and —(C=O)—$CH_2$—NH—C(=O)—$CH_2$—O—$(CH_2)_2$—O—$(CH_2)_2$—NH—, particularly selected from —(C=O)—$(CH_2)_4$—NH—C(=O)—$(CH_2)_4$—NH— and —(C=O)—$CH_2$—NH—C(=O)—$CH_2$—O—$(CH_2)_2$—O—$(CH_2)_2$—NH.

More preferably, $E^1$ is —$(CH_2)_3$— and $E^2$ is selected from —(C=O)—$(CH_2)_4$—NH—C(=O)—$(CH_2)_4$—NH— and —(C=O)—$CH_2$—NH—C(=O)—$CH_2$—O—$(CH_2)_2$—O—$(CH_2)_2$—NH—. Preferred groups-$E^1$-NH—$E^2$-are also disclosed in the particular Examples herein.

In particular embodiments, -$E^1$-NH-$E^2$- differs from a respective linking moiety disclosed in WO 07096662 A2.

In a further aspect, the present invention relates to a phanuaceutical composition comprising a compound of the invention and at least one pharmaceutically acceptable excipient.

"Pharmaceutically acceptable excipients" are well known in the art as substances other than the active ingredients that may be part of pharmaceutical compositions. Examples for excipients include, but are not limited to one or more carriers, coatings, disintegrants, binders, fillers, diluents, lubricants, stabilizers, surfactants, preservatives, flavouring agents, colouring agents, sorbents, sweeteners, and any combinations thereof.

The pharmaceutical composition may also comprise one or more additional active ingredients known to the skilled person to provide a combination therapy, such as of a disease or disorder described herein.

An exemplary dosage of the compound of the invention may be in the range from about 0.0001 to about 1000 mg, such as from about 0.0002 to about 500 mg, such as from about 0.0005 to about 100 mg, such as from about 0.001 to about 10 mg per kg body weight per day. As used herein, "about" refers to a range around a given value plus/minus 10% thereof. Accordingly, about 10 mg per kg body weight per day refers to 9 to 11 mg per kg body weight per day.

It will be understood that a person skilled in the art can readily determine suitable dosages and administration schemes on the basis of his knowledge, wherein preferred dosages and administration schemes will depend on the condition to be treated.

The pharmaceutical compositions of the invention may be administered by routine methods, for example via oral/peroral, parenteral (preferably intravenous, e.g. by injection), intraperitoneal, intradermal, transdermal, inhalational, topical or cutaneous via a creams, gel or solutions, nasal, buccal, rectal, or vaginal administration routes or via an implanted reservoir or infusion. Suitable dosage folins include, but are not limited to capsules, tablets, pellets, aqueous suspensions, aqueous solutions, aerosols, suppositories, creams, gels, ointments and transdermal or buccal patches. According to a preferred embodiment, the pharmaceutical composition is administered intravenously. Preferred embodiments involve injection. Other preferred embodiments involve infusion and topical applications. Other preferred embodiments involve topical applications and subcutaneous depots.

The compounds of the invention, which are believed to bind the CXCR4 receptor with high affinity, may be suitable for blocking, disrupting or otherwise interfering with the interaction between the CXCR4 receptor and its natural ligand. Likewise, they may be suitable for targeting cytotoxic moieties, such as therapeutic radioisotopes or the like to CXCR4 receptors.

Therefore, the compounds and compositions of the invention may be used in methods of treating CXCR4 receptor-related conditions, disorders and diseases.

Accordingly, in a further aspect, the present invention relates to a compound as defined above for use as a medicament.

In a further aspect, the present invention relates to a compound as defined above or composition as defined above for use in a method for the prevention or treatment of a CXCR4 receptor-related disease or disorder or the treatment of diseases or disorders that can benefit from a CXCR4 targeted treatment, such as the mobilization and collection of stem cells or would healing.

In addition, the invention relates to the use of a compound as defined above or composition as defined above for the manufacture of a medicament for preventing a CXCR4 receptor-related disease or disorder, as well as to the use of a compound or composition as defined above for the manufacture of a medicament for treating a CXCR4 receptor-related disease or disorder or the treatment of diseases or disorders that can benefit from a CXCR4 targeted treatment, such as the mobilization and collection of stem cells or would healing.

In addition, the invention relates to a method of preventing a CXCR4 receptor-related disease or disorder, the method comprising a step of administering a compound as defined above or composition as defined above to a subject in need thereof, as well as to a method of treating a CXCR4 receptor-related disease or disorder, the method comprising a step of administering a compound as defined above or composition as defined above to a subject in need thereof.

"CXCR4" or "CXCR4 receptor" as used herein, refers to a particular receptor, the CXC chemokine receptor 4, which well-known to the skilled person, and which is also called "fusin". It is e.g. expressed on many stem cells, but also in numerous cancers, on various immune cells and in tissue under remodeling conditions.

Term "CXCR4" or "CXCR4 receptor" as used herein also includes variants thereof. Variants particularly include isoforms encoded by alternative transcriptional splice variants, as well as mutated or truncated forms of said receptor. Preferably the gene or protein sequences of a variant CXCR4 has at least 10%, 20%, 30%, 40%, 50%, 60%, 70%, particularly at least 80% or 90%, more particularly at least 95% or 97%, especially at least 99% sequence identity to a native sequence of CXCR4. As used herein, a gene or protein is said to have "X % sequence identity" to a given sequence if upon an alignment with the best matching sequence of said given sequence the number of matching nucleotides or amino acids, respectively, divided by the number of nucleotides or amino acids of the shorter sequence multiplied by 100 is X. Methods and tools of aligning sequences are well known to the skilled person.

Mutations of a CXCR4 encoding sequence leading to truncated forms of the CXCR4 receptor may e.g. influence the extent of an inflammatory reaction or the metastatic potential of a cancer. Besides, mutations in the CXCR4 gene have been shown to be associated with e.g. WHIM (warts, hypogammaglobulinemia, infections, and myelokathexis) syndrome.

A "CXCR4 receptor-related disease or disorder" as used herein includes any pathological condition, a disease or a disorder, which is directly or indirectly related to the CXCR4 receptor per se or to its function, such as to the interaction of the CXCR4 receptor with its natural ligand CXCL12 (SDF-1). CXCR4 receptor-related disease or disorder particularly includes any disease or disorder that is related directly, indirectly, immediately and/or not immediately to the CXCR4 receptor, the CXCR4 receptor status or CXCR4 receptor signaling. Numerous CXCR4 receptor-related diseases or disorders are known in the art (cf. e.g. Taniuchi et al., 2005; Kim et al., 2005; Phillips et al., 2003).

As to the prevention or treatment of a CXCR4 receptor-related disease or disorder, said CXCR4 receptor-related disease or disorder e.g. also includes any disease or disorder involving cells expressing the CXCR4 receptor, such as cancer cells. It may also be a disease or disorder caused or promoted by a cellular pathway such as a signaling pathway involving the CXCR4 receptor. It may also be a disease or disorder caused or promoted by an altered expression such as an overexpression of the CXCR4 receptor and/or by a modification of the CXCR4 receptor.

Particularly as to aspects of the invention that involve imaging or monitoring of CXCR4 receptors, a CXCR4 receptor-related disease or disorder may be any disease or disorder involving any alteration in the status of the CXCR4 receptor, e.g. an altered expression such as an overexpression or decreased expression of the CXCR4 receptor. Likewise, also any CXCR4 receptor-related disease or disorder is envisaged, the therapy or treatment of which is directly or indirectly related to an alteration in the status of the CXCR4 receptor, e.g. an altered expression such as an overexpression or decreased expression of the CXCR4 receptor.

As one non-limiting example in this respect, reference is made to Her2/neu expression in mammacarcinoma, where Her2/neu stabilizes the CXCR4 receptor status, and where an antibody therapy towards Her2/neu leads to a destabilization the CXCR4 receptor status and finally a decreased CXCR4 expression.

As referred to herein, the CXCR4 receptor-related disease or disorder may be a neoplastic condition, an immune disease, an autoimmune disease, a vascular disease, a heart disease, an inflammatory condition, a wound and/or a neurological disease.

A "neoplastic condition" as used herein refers to a condition characterized by an increase in mass of a tissue resulting in a neoplasm. Said neoplasm results from a neoplasia, i.e. the proliferation of cells. Preferably, according to the invention, such neoplastic condition relates to an abnormal mass of a tissue, such as a tumor, particularly a malignant tumor. Accordingly, in a preferred embodiment the neoplastic condition is a cancer and corresponding metastatic processes.

"Immune diseases" are diseases involving a dysfunction of the immune system, such as by an overactive or insufficiently active immune system, which diseases may be congenital or acquired and may affect various components of the immune system.

"Autoimmune diseases" are particular immune diseases, which are known within the art as diseases arising from an overly active immune response of the body against substances and tissues that are normally present in the body. They include, but are not limited to multiple sclerosis (MS), lupus erythematosus, Sjogren's syndrome, ulcerative colitis and rheumatoid arthritis.

"Cardio-Vascular diseases" are known to the skilled person as diseases primarily affecting the blood vessels. They include e.g. atherosclerosis, hypertonic diseases and thrombosis, but also ischemic heart disease, myocardial infarction. Vascular diseases may involve an inadequate ratio of oxygen need to oxygen supply. "Inflammatory conditions" as used herein comprise diseases or disorders associated with inflammation which include, but are not limited to atherosclerosis, rheumatoid arthritis, vasculitis and asthma. Preferably, the inflammatory condition is a vascular inflammatory condition such as atherosclerosis or a disease related to atherosclerosis such as coronary heart disease (CHD). "Neurological diseases" include diseases and disorders that can affect the central nervous system, the peripheral nervous system, or the autonomic nervous system. They include but are not limited to multiple sclerosis (MS), Alzheimer's disease or stroke.

In a preferred embodiment of the invention, the CXCR4 receptor-related disease or disorder is any one selected from HIV infection, cancer, rheumatoid arthritis, multiple sclerosis, atherosclerosis and asthma. In one particular embodiment, the CXCR4 receptor-related disease or disorder is atherosclerosis.

In another particular embodiment, the CXCR4 receptor-related disease or disorder is a leukaemia, kaemia, particularly chronic lymphocytic B-cell leukaemia (B-CLL). In another particular embodiment, the CXCR4 receptor-related disease or disorder are lymphoproliferative diseases and disorders, i.e. lymphomas and myelomas.

In another particular embodiment, the CXCR4 receptor-related disease or disorder is pain or involves pain.

In another embodiment of the invention, the CXCR4 receptor-related disease or disorder is selected from any of the diseases and disorders referred to on pages 49 to 58 of WO2008/08854A, which is specifically incorporated herein by reference.

According to a particular preferred embodiment, the CXCR4 receptor-related disease or disorder is a cancer. The term "cancer" as used herein particularly includes carcinomas, sarcomas, melanomas, blastomas and lymphomas. The term "cancer" may refer to a cancer not including metastases, a cancer including metastases, or to cancer metastases. Hence, it may refer to primary tumors with or without at least one metastasis, or solely refer to cancer metastasis/metastases. Preferably, the cancer and/or cancer metastases expresses the CXCR4 receptor. Accordingly, "cancer metastasis" or "cancer metastases" per se is/are another preferred example for a CXCR4 receptor-related disease or disorder.

In one embodiment of the invention, the cancer is selected from the group consisting of astrocytoma, B-cell lymphoma, breast adenocarcinoma, breast carcinoma, cervical adenocarcinoma, colon adenocarcinoma, colorectal adenocarcinoma, colorectal carcinoma, glioblastoma, hepatocellular carcinoma, hepatoma and pancreatic carcinoma, leukaemia, large cell lung cancer, lung adenocarcinoma, lung carcinoma, lung mesothelioma, lung squamous cell carcinoma, melanoma, neuroblastoma, non small cell and small cell lung cancer (NSCLC and SCLC), ovarian cancer, pancreatic adenocarcinoma, pancreatic carcinoma, prostate adenocarcinoma, prostate carcinoma, rectal adenocarcinoma, renal cell adenocarcinoma cinoma and adrenal carcinoma, In another embodiment, the cancer is selected from the group consisting of breast adenocarcinomas, carcinomas, Burkitt's B-cell lymphoma, cervical adenocarcinomas, colon and rectal adenocarcinomas, oesophageal cancer, gliomas, glioblastomas, hepatocellular carcinomas (malignant hepatomas), hepatomas, ovarian cancer, leukemia, mammacarcinomas, melanoma, neuroblastoma, nasopharyngeal adenocarcinoma, non-small cell lung cancer (NSCLC), pancreatic adenocarcinomas, prostate cancer, small cell lung cancer (SCLC), T-cell lymphoma, and thyroid cancer.

In a preferred embodiment, the cancer is selected from the group consisting of breast adenocarcinoma, colorectal adenocarcinoma, leukemia, lymphoma, myeloma, lung cancer, melanoma, ovarian cancer, prostate cancer, prostate adenocarcinoma.

The CXCR4 receptor-related diseases and disorders described herein may be treated by a compound of the invention by administering it to a subject in need thereof. The compound may be administered in form of a pharmaceutical composition as described hereinabove. It may be administered by any known administration route including the ones described here-inabove. In a preferred embodiment, the compound is formulated as pharmaceutically acceptable salt as described hereinabove.

A "subject" as used herein may be an animal or human subject. In preferred embodiments, the subject is a mammalian subject, more preferably, but not exclusively, a human subject. In one embodiment, the subject is a human subject having a neoplasia such as a cancer or suspected of having a neoplasia such as a cancer, wherein the cancer may or may not involve metastases.

In another embodiment, the subject is an animal, such as e.g. a dog, a cat or even a horse, having a neoplasia such as a cancer or suspected of having a neoplasia such as a cancer, wherein the cancer may or may not involve metastases.

In another embodiment, the subject is a human or an animal, having one of the aforemented CXCR4 related or CXCR4 mediated diseases or disorders or diseases or disorders that can be imaged with a CXCR4 targeted imaging agent of can be treated with a CXCR4 targeted therapeutic agent.

Without the intention of being bound by theory, the present inventors consider that cancer metastasis may be caused by circulating cancer cells expressing CXCR4 that are targeted to sites that attract CXCR4-expressing cells such as stem cells, e.g. to the lungs, liver and bone marrow, but also other tissues and organs. CXCR4 overexpression has been shown on numerous tumors. CXCR4 expression on cancer cells may particularly be increased under hypoxic conditions. Accordingly, in a particular embodiment, the invention relates to a compound of the invention for use in reducing, preferably treating cancer metastases. In another embodiment, the invention relates to a method of reducing the tumor load and corresponding metastases, the method comprising administering a compound of the present invention to a subject in need thereof, particularly a subject having cancer or suspecting of having cancer.

When used in preventing or treating a CXCR4 receptor-related disease or disorder such as a cancer, the compounds of the invention may or may not include one or more cytotoxic moieties. In one embodiment, the compounds include one or more cytotoxic moieties for targeted chemotherapy of CXCR4-positive tumors, such as CXCR4-expressing cancer.

Examples for "cytotoxic moieties" are well-known within the art and include radionuclides as described herein and chemotherapeutical agents. Chemotherapeutical agents include, but are not limited to bleomycin, carboplatin, cisplatin, cyclophosphamide, chlorambucil, docetaxel, doxorubicin, etoposide, methotrexate, mitoxantrone, paclitaxel, prednisone, teniposide, valrubicin, vinblastine, vincristine, vindesine, vinorelbine. Preferred cytotoxic moieties may be selected from any of those cytotoxic compounds generally used for chemotherapy of the tumor concerned.

In addition, the compounds of the invention, which are thought to bind the CXCR4 receptor with high affinity, may be particularly suitable for use in any type of imaging applications and/or any applications involving the labelling of CXCR4 receptor(s).

Accordingly, in a further aspect, the invention relates to the use of a compound as defined above, wherein the compound comprises a detectable label, for the imaging of CXCR4 receptors, in particular for medical imaging, especially for diagnostic imaging.

The imaging may be any one of in vivo-imaging, ex vivo-imaging, and in vitro-imaging.

Likewise, in another aspect, the invention relates to a method of imaging CXCR4 receptors, in particular of medical imaging, especially of diagnostic imaging, the method comprising administering a compound as defined above or composition as defined above to a sample or a subject, wherein the compound comprises a detectable label.

Said method may be any one of an in vivo- method, an ex vivo- method, and an in vitro-method. Preferably, said method is neither a method for treatment of the human or animal body by surgery or therapy. Generally, in certain embodiments, a method of the invention does comprise a diagnostic method practiced on the human or animal body by means of typically used imaging instrumentation suitable for localization and visualization of the distribution of the compounds invented comprising of a detectable label, preferably but not exclusively a radionuclide. "Imaging" is well known to the skilled person. Non-limiting suitable imaging techniques and methods are e.g. described in Weissleder R et al, 2008, Shah K et al, 2005, Weissleder R et al, 2003 and Kuehl Het al, 2007.

As used herein, imaging preferably relates to "biological imaging" and/or "molecular imaging", particularly to "medical imaging", and especially to "diagnostic imaging" and "therapy monitoring".

"Biological imaging" as used herein generally refers to any imaging used in biology or medicine, particularly to imaging for examining biological material such as a biological sample or a biological subject or part thereof.

"Molecular imaging" is well known in the art (cf. e.g. Shah K et al, 2005) and includes imaging any type of molecular and/or cellular processes, e.g. with the aim of monitoring metabolic processes related and corresponding with a disorder or a disease, progression or regression of a disease such as cancer.

"Medical imaging", which is generally well-known within the art, concerns imaging for medical purposes. It preferably includes creating images of a sample derived from a subject, or of a subject or part of a subject. Medical imaging may be performed to reveal, diagnose or examine a disease or disorder, preferably a CXCR4 receptor-related disease or disorder such as any of the ones described hereinabove.

"Diagnostic imaging" as used herein refers to imaging for diagnostic purposes, such as for diagnosing a disease or disorder, preferably a CXCR4 receptor-related disease or disorder such as any of the ones described hereinabove. A method of diagnostic imaging may or may not be a diagnostic method practiced on the human or animal body. "Therapy monitoring" as used herein generally refers to any imaging methodology used to monitor or to control the effects of a treatment of a disease or disorder, preferably but not exclusively a CXCR4 receptor-related disease or disorder such as any of the ones described hereinabove. Thus. therapy monitoring allow particularly for early response evaluation and early detection of recurrent diseases.

A "sample" may be any sample. Non-limiting examples for a sample are cells, tissue section(s), tissue(s), and organ(s).

Preferably, the sample is derived from a subject, particularly from a human subject.

According to the invention, imaging may be carried out on any sample or subject or part of a subject comprising CXCR4 receptors.

According to the invention, imaging may involve any kind of imaging techniques known to the skilled person, wherein said techniques include, but are not limited to positron emission tomography (PET), single photon emission computed tomography (SPECT), magnetic resonance imaging (MRI), tomography such as computed tomography (CT), imaging via gamma cameras, imaging via optical imaging system, fluorescence imaging, fluorescence tomography, autoradiography, imaging via phosphor imagers, and any combination(s) thereof.

Preferably, imaging occurs via any of positron emission tomography (PET), single photon emission computed tomography (SPECT), and magnetic resonance imaging (MRI). As will be understood by the skilled person, particularly preferred embodiments for such techniques depend on the respective detectable label used. Generally, when the label is a radionuclide, nuclide, the detection step may preferably be performed using positron emission tomography (PET) or single photon emission computed tomography (SPECT). Magnetic resonance imaging (MRI) is preferred when magnetic or paramagnetic labels, such as a gadolinium label, are employed. Detectable labels for use with the compounds of the present invention are described hereinabove. In one embodiment, the detectable label is a fluorescent label. In one embodiment, the detectable label allows its use in conjunction to hybrid systems, such as dual PET/CT, SPECT/CT or PET/MRI. In this case, CT or MRI are preferably employed to analyze the morphology of the sample, subject, or part thereof, which is subjected to imaging.

Imaging may be carried out to determine the distribution or the accumulation of the detectable label, preferably via commonly used methods, such as autoradiography or phosphor imagers. Imaging may e.g. be carried out to obtain relative or quantitative distribution or accumulation data.

In an exemplary embodiment, (a method of) in vitro- or ex vivo-imaging involves the following steps: A compound of the invention comprising a detectable label is contacted with a sample such as cells, tissue section(s), tissue(s) or organ(s). The compound is preferably dissolved in a suitable buffer and said sample is incubated with this buffer. Incubation may occur for any suitable period of time such as in the range of seconds, minutes or hours. Subsequently, the detectable label is detected. This is effected by a suitable device, the nature of which depends on the imaging method used. Preferably or alternatively, in a further step, one or more images are obtained. This may e.g. be by direct imaging or imaging of slices of the incubated tissues.

In an exemplary embodiment, (a method of) in vivo-imaging involves the following steps: A compound of the invention comprising a detectable label is introduced into the living organism e.g. by injection or infusion, and, subsequently, the detectable label is detected. This is effected by a suitable device, the nature of which depends on the imaging method used. Preferably or alternatively, in a further step, one or more images are obtained. The acquisition of the imaging data such as the emission data is carried out over a suitable period of time such as for minutes to hours. Using commonly employed equipment and suitable software packages, these data may e.g. result in planar or 3D distribution pattern of the activity distribution in the organism. Depending on the method, the obtained data can be qualitative or quantitative.

In an exemplary embodiment, (a method of) in vivo-imaging involves the following steps: a) positioning a subject in an imaging device, b) delivering a compound of the invention to the subject, c) acquiring at least one image; or a) delivering a compound of the invention to the subject, b) positioning a subject in an imaging device, c) acquiring at least one image.

In preferred embodiments, a method of imaging does not involve a step of treatment of the human or animal body by surgery or therapy. Yet, certain aspects of the invention explicitly concern a compound or composition of the invention for use in a method of imaging CXCR4 receptors, in particular of medical imaging, especially of diagnostic imaging, wherein said method involves at least one step of treatment of the human or animal body by surgery or therapy.

Preferably, any of the (methods of) imaging referred to herein is employed for the imaging of CXCR4 receptors on stem cells, tumor stem cells, hematopoietic stem cells and other progenitor cells and tissues under remodeling and repair by stem and progenitor cell adhesion.

"Tissues under remodeling and repair by stem and progenitor cell adhesion" as used herein relates to, without being limited thereto, cells or tissues such as cells or tissues engaged in a neoangiogenic process, cells or tissues affected by vascular injury and cells or tissues affected by myocardial infarction.

Preferably, in vivo-imaging of CXCR4 expression using compounds of the present invention that are radiolabeled with appropriate radionuclides is effected via PET or SPECT. In in vivo-imaging, images of the subject may be taken after a short time after administration, by which stage any tissues having a relatively high expression of CXCR4 will show a relative concentration of the compound of the invention.

In case of in vivo-methods for imaging, the compound preferably comprises a radiolabel and the imaging is preferably performed using PET or SPECT. Preferred embodiments concern in vivo-methods for the diagnostic imaging of a neoplastic condition.

In case of in vitro-methods for imaging, the compound preferably comprises a radiolabel or fluorescent label and the imaging is preferably performed using autoradiography or fluorescence. Preferred embodiments concern in vitro-methods for the diagnostic imaging of a neoplastic condition.

In preferred embodiments, the invention relates to the imaging of tumors such as cancer. As described above, cancer may refer to a cancer not including metastases, to a cancer including metastases, or to cancer metastases.

In one embodiment, the cancer is selected from the group consisting of astrocytoma, B-cell lymphoma, breast adenocarcinoma, breast carcinoma, cervical adenocarcinoma, colon adenocarcinoma, colorectal adenocarcinoma, colorectal carcinoma, glioblastoma, hepatocellular carcinoma, hepatoma and pancreatic carcinoma, leukaemia, large cell lung cancer, lung adenocarcinoma, lung carcinoma, lung mesothelioma, lung squamous cell carcinoma, melanoma, neuroblastoma, non small cell and small cell lung cancer (NSCLC and SCLC), ovarian adenocarcinoma, pancreatic adenocarcinoma, pancreatic carcinoma, prostate adenocarcinoma, prostate carcinoma, rectal adenocarcinoma, and renal cell adenocarcinoma.

In another embodiment, the cancer is selected from the group consisting of breast adenocarcinomas, Burkitt's B-cell lymphoma, cervical adenocarcinomas, colon and rectal adenocarcinomas, oesophageal cancer, gliomas, glioblastomas, hepatocellular carcinomas (malignant hepatomas), hepatomas, leukaemia, mamma-carcinomas, melanoma, neuroblastoma, nasopharyngeal adenocarcinoma, non small cell lung cancer (NSCLC), pancreatic adenocarcinomas, prostate cancer, small cell lung cancer (SCLC), T-cell lymphoma, and thyroid cancer.

In a preferred embodiment, the cancer is selected from the group consisting of breast adenocarcinoma, colorectal adenocarcinoma, lymphoma, melanoma carcinoma, prostate carcinoma, prostate adenocarcinoma, small cell lung cancer.

Preferably, the imaging allows a clear delineation of CXCR4 positive tumors (including or not including any metastases), e.g. in vivo. Imaging according to the invention may provide tools for the diagnosis of cancer, the detection of tumors and/or tumor metastases, the investigation of tumors and/or tumor metastases, the removal of tumors and/or tumor metastases via surgery, and the like.

In one embodiment of the invention, the imaging is employed for diagnosing or investigating any CXCR4 receptor-related disease or disorder, such as the ones referred to herein.

In one particular embodiment, said disease or disorder is selected from any of the diseases and disorders referred to on pages 49 to 58 of WO2008/08854A, which is specifically incorporated herein by reference.

In one preferred embodiment, imaging is employed for diagnosing or investigating an immune disease, an autoimmune disease, an inflammatory condition and/or a neurological disease, preferred examples thereof being as described above.

In other preferred embodiments, (a method of) imaging is employed for monitoring any CXCR4 receptor-related disease or disorder, such as the ones referred to herein. In particular embodiments, (a method of) imaging is employed for monitoring for investigating inflammatory processes or angiogenic processes.

Accordingly, in a further aspect, the invention relates to a method for monitoring a CXCR4 receptor-related disease or disorder. The invention also relates to a compound or composition of the invention for use in monitoring a CXCR4 receptor-related disease or disorder. The invention also relates to a compound or composition of the invention for use in a method of monitoring a CXCR4 receptor-related disease or disorder.

Using a compound of the invention in imaging as described herein, or employing a method of imaging as described herein, is preferably done to determine the localization, the extent and/or the kinetics of a disease or disorder. In the case of analyzing kinetics, the extent of the disease is preferably analyzed early during therapy in order to be able to quickly detect a response to therapy.

The compounds of the invention are expected to allow early response monitoring as well as the selection of patients that may especially benefit from a planned therapy. A selection of patients means that patients are selected before commencing any therapy, for which disease it is know that the density of CXCR4 receptors correlates with the reaction to therapy or with the expected response. The therapy must not necessarily be a therapy directed to CXCR4, such as by employing a compound of the invention as an antagonist, but can be directed to any target structure which correlates with CXCR4 receptor density.

One exemplary embodiment relates to the qualitative or quantitative imaging of the CXCR4 receptor status in vivo using compounds of the invention comprising a detectable label, e.g. by means of PET using the aforementioned compounds, for planning of individualized therapies that directly address (are mediated by) the CXCR4 receptor status or indirectly affect or modulate the CXCR4 receptor status.

Non-limiting examples in this respect relate to the therapy of mammacarcinomas by means of anti-Her2/neu antibodies (e.g. with trastuzumab, trade name Herceptin®) and the antiangiogenetic antibody therapy of colon carconmas using anti-VEGF-A antibody bevacizumab (trade name Avastin®).

In another embodiment, a compound of the invention is employed to follow or monitor the efficiency of such therapies by therapy response evaluation, preferably early therapy response evaluation. For this purpose the compounds of interest may be injected prior to or early after beginning of such therapies to evaluate response to therapy via comparison of the signal, such as the CXCR4-PET signal, prior to (baseline scan) as well as early after or during therapy.

Other preferred embodiments relate to the use of a compound of the invention for imaging inflammatory processes, preferably in vivo, particularly via PET imaging, and to a corresponding method.

Other preferred embodiments relates to the use of a compound of the invention for imaging angiogenetic processes/angiogenesis processes as well as to a corresponding method.

A further aspect of the invention relates to the use of a CXCR4 receptor ligand, preferably a compound as defined hereinabove, to monitor the extent of stem cell depletion, such as during an endoradiotherapeutic approach. Preferably, the use alternatively or further includes monitoring an increasing pool of stem cells in the bone marrow, such as after stem cell transplantation.

One embodiment concerns a method of monitoring the extent of stem cell depletion during an endoradiotherapeutic approach, the method comprising administering a CXCR4 receptor ligand, preferably a compound as defined hereinabove, to a sample or a subject. Preferably, the method includes a subsequent step of monitoring the increasing pool of stem cells in the bone marrow after stem cell transplantation.

Said CXCR4 receptor ligand may be any known molecule that specifically binds to the CXCR4 receptor. Examples include but are not limited to FC131 referred to above and its derivatives, particularly i) the ligands disclosed in WO 2007/096662 A2, ii) the ligands disclosed in WO 2009/027706 A2. Preferably, the CXCR4 receptor ligand is any of the compounds described hereinabove. Preferably, said ligand comprises a detectable label, particularly the ones described herein.

In one embodiment, the invention relates to the use of a compound of the invention for the diagnostic imaging of changes of the status of CXCR4 expressing cells, particularly stem cells, in the bone marrow.

In a further aspect, the present invention relates to a compound as defined above or composition as defined above for use in a diagnostic method practiced on the human or animal body for the diagnosis of a CXCR4 receptor-related disease or disorder.

Such diagnostic method includes technical steps that are constitutive for making the diagnosis, wherein specific interactions with the human or animal body occur when carrying out these steps, as well as the diagnosis for curative purposes. Said diagnosis stricto sensu represents the deductive medical decision phase as a purely intellectual exercise.

In one embodiment, such diagnostic method comprises the steps of administering a compound of the invention to a subject, collecting imaging data from the subject, comparing the imaging data with standard values, finding a symptom of a CXCR4 receptor-related disease or disorder during the comparison, attributing the symptom to a particular clinical picture to establish the diagnosis.

Moreover, the invention relates to a method of diagnosing a CXCR4 receptor-related disease or disorder, wherein the method comprises a step of administering a compound as defined above or composition as defined above to a sample derived from a subject or to a subject, and a subsequent step of imaging CXCR4 receptors.

Preferably, the compound comprises a detectable label, and the method comprises a step of administering a compound as defined above to a sample derived from a subject or to a subject, and particularly comprises a subsequent step of detecting the detectable label and/or a subsequent step of obtaining one or more images.

Due to their features, the compounds of the invention may be suitably used for various other applications directly or indirectly related to the CXCR4 receptor. Accordingly, in even further aspects, the present invention relates to any of the following embodiments:

Use of a compound of the invention, particularly wherein the compound comprises a detectable label, in the visualization of CXCR4 receptor and CXCR4 receptor containing tissue.

Use of a compound of the invention for affinity purification of CXCR4 receptors or cells containing one or more CXCR4 receptors.

Use of a compound of the invention for the diagnostic imaging of changes of CXCR4 receptor expression of cells, preferably stem cells, particularly cells in the bone marrow.

A method of affinity purification of CXCR4 receptors or cells containing one or more CXCR4 receptors, comprising a step of contacting a compound of the invention with a sample containing a CXCR4 receptor or cells containing one or more CXCR4 receptors, particularly wherein the method further comprises one or more steps of removing other constituents from the sample to increase purity of the CXCR4 receptor or cells containing one or more CXCR4 receptors.

The CXCR4 ligands of the present invention may be modified with additional (functional) moieties and/or moieties that immobilize the CXCR4 ligands.

A method of determining the metastatic potential of cells of a neoplasia, the method comprising exposing said cells to a compound of the invention, so as to allow the compound to bind to CXCR4 receptors on the surface of the cells, and determining the presence and/or amount of compound bound to the cells. In this method, an increased number of CXCR4 receptors correlates to an increased metastatic potential of the primary tumor. Accordingly, conclusions as to the metastatic potential of cells of a neoplasia may be drawn from the presence and/or amount of a compound described above bound to the cells via CXCR4 receptors. According to the current knowledge of the inventors, the compounds of the invention may allow for imaging of the metastatic potential of primary tumors of e.g. a cancer selected from the group consisting breast adenocarcinomas, Burkitt's B-cell lymphoma, cervical adenocarcinomas, colon and rectal adenocarcinomas, oesophageal cancer, gliomas, glioblastomas, hepatocellular carcinomas (malignant hepatomas), hepatomas, leukaemia, mamma-carcinomas, melanoma, neuroblastoma, nasopharyngeal adenocarcinoma, non small cell lung cancer (NSCLC), pancreatic adenocarcinomas, prostate cancer, small cell lung cancer (SCLC), T-cell lymphoma, and thyroid cancer. Said method of determining the metastatic potential of cells may be carried out in vivo or in vitro (i.e. using a sample of cells or tissue removed from a patient). When the compound of the invention comprises a radionuclide, the imaging, or the determination of the presence and/or amount of bound compound, may in particular be performed using PET or SPECT. When magnetic or paramagnetic labels are employed, magnetic resonance imaging is preferred.

The compounds described hereinabove may also be suitably employed in the field of stem cell mobilization and/or transplantation. As it is known in the art (cf. Levesque et al., 2008), hematopoietic stem cells (HSCs), which normally reside in the bone marrow, can be forced into the blood by mobilization, which is used clinically to harvest large numbers of HSCs for transplantation. One example for a suitable compound is plerixafor described above. The mobilization of hematopoietic stem cells from the bone marrow to the bloodstream makes use of the interaction between the chemokine SDF-1/CXCL12 and its receptor CXCR4, which serves to retain HSCs within the bone marrow. For mobilization, this interaction may be disturbed by molecules acting as CXCR4 ligands, which is why the compounds of the present invention, e.g. as direct antagonists of the interaction between SDF-1 and CXCR4, may be suitable for inducing mobilization of stem cells. Therefore, it is envisaged that the compounds of the present invention may function as such mobilizing agents and may be used for improving the stem-cell harvest from bone-marrow donors and shorten the collection time as compared to originally employed methods.

Accordingly, in a further aspect, the invention relates to the use of a compound described hereinabove for mobilizing and/or harvesting stem cells. The invention further relates to a compound as defined hereinabove for use in a method of mobilizing and/or harvesting stem cells.

The invention also relates to a method of mobilizing stem cells in a subject, the method comprising a step of administering a compound of the present invention to a sample containing stem cells or to a subject. Also envisaged is a method of harvesting stem cells, the method comprising a step of administering a compound of the present invention to a sample containing stem cells or to a subject and a subsequent step of collecting stem cells from said sample or subject. Preferably, the latter methods are no methods for the treatment of the human or animal body by surgery or therapy.

One exemplary application for stem cell mobilization is its use during cancer therapy, such as by radioimmunotherapeutic treatment, e.g. of lymphomas by means of anti-CD20 radio-labeled antibodies. To overcome the side effects of such therapies, i.e. complete stem cell (bone marrow) depletion, stem cell transplantations are carried out. Prior to the radiotherapeutic approach, stem cells are mobilized from their niches in the bone marrow, are collected from the blood, stored and re-injected after the therapy. Since CXCR4 ligands have been described to mobilize stem cell from the bone marrow niches, the compounds of the invention may be valuable compounds for this therapeutic approach.

Thus, in a further aspect, the invention relates to a compound as defined above or composition as defined above for use in a method of stem cell transplantation comprising the following steps
i) administering a compound of the present invention to a subject,
ii) collecting stem cells from said subject,
iii) optionally storing the collected stem cells, and
iv) re-introducing the collected stem cells into the subject.

Further uses and methods in which the compounds of the invention may be employed will be readily apparent to a person skilled in the art based on the disclosures herein.

In addition, the compounds of the invention, when labeled with a therapeutic radioisotope, may be particularly suitable for use in any type of therapeutic applications.

"Therapeutic Radioisotope" as used herein generally refers to any radioisotope that emits beta" particles or alpha particles suitable to cause a radiotoxic effect in cells, i.e. by damaging the DNA of cells. Typical examples of therapeutic radioisotopes are: 177Lu, 90Y, 131I; 161Tb, 166Ho, 186Re, 188Re, 211At, 212Bi and 225Ac.

Accordingly, in a further aspect, the invention relates to the use of a compound as defined above, wherein the compound comprises a therapeutic label, for the treatment of CXCR4 receptor related or mediated diseases or disorders.

Said method may be any one of an in vivo- method. Preferably, said method is a method for treatment of the human or animal body by intravenous application or infusion of a compound of invention labeled with a therapeutic radioisotope.

In an exemplary embodiment, (a method of) treatment with a compound of invention labeled with a therapeutic radioisotope involves the following steps: A compound of the invention comprising a therapeutic radioisotope is introduced into the living organism e.g. by injection or infusion. In the case that the used radionuclide co-emits a detectable radiation (as in the case of e.g. Lu-177 and I-131), the distribution of the injected formulation in the living body can be visualized by means of SPECT imaging or scintigraphic methods after several hours up to days after application. Typically, several GBq of the therapeutic active compound are administered, depending on the energy of the emitted particle.

In preferred embodiments, the invention relates to the treatment of tumors such as cancer with a compound of the invention comprising a therapeutic radioisotope. As described above, cancer may refer to a cancer not including metastases, to a cancer including metastases, tases, or to cancer metastases. Relevant cancer are those mentioned before and relevant for the treatment with pharmaceutical active compounds and those listed relevant for imaging.

EXAMPLE

Abbreviations:
DCM: Dichloromethane, RP-HPLC: Reversed Phase High Pressure Liquid Chromatography, TFA: Trifluoroacetic acid, NMR: Nuclear Magnetic Resonance, THF: Tetrahydrofuran, EtOAc: Ethylacetate, RT: room temperature, Boc: tert-butyloxycarbonyl, DIPEA:
Diisopropylethylamine, MeOH: methanol, NMP: N-methyl-pyrollidone, DPPA: Diphenylphosphoryl azide, DMF: N,N-dimethylformamide, Ac: acetate, Fmoc: Fluorenylmethyloxycarbonyl, thyloxycarbonyl, Xaa: undefined amino acid, SPPS: Solid Phase Peptide Synthesis, Orn: ornithine, Nal: L-3-(2-naphthyl)alanine, R(Pbf): arginine with Pbf protected side chain, Tyr(tBu): tyrosine with tBu protected side chain, Fmoc-Tyr(tBu): tyrosine with tBu protected side chain and Fmoc protected $N^\alpha$, ABS: 4-aminobenzoic acid, Fmoc-ABS: N-Fmoc protected 4-aminobenzoic acid, AMBS: 4-aminomethylbenzoic acid, Fmoc-AMBS: N-Fmoc protected 4-aminomethylbenzoic acid, betaAla: beta-alanine; 3-aminopropanoic acid, Fmoc-betaAla: N-Fmoc protected beta-alanine, AVS: 5-aminovaleric acid, Fmoc-AVS: N-Fmoc protected 5-aminovaleric acid, Ahx: 6-aminohexanoic acid, Fmoc-Ahx: N-Fmoc protected 6-aminohexanoic acid, Trigas: triethylenglycol-8-amino-1-acid, Fmoc-Trigas: N-fluorenylmethoxycarbonyl-triethylenglycol-8-amino-1-acid, RNalG/R Nal G:arginine, L-3-(2-naphthyl)alanine, glycine. Besides, the abbreviation "yorn" specifies that in the respective cyclopeptide, $Xaa^1$ is D-Tyr, the residue between $Xaa^1$ and $Xaa^2$ is derived from D-Orn, and R is H; whereas the abbreviation "yorn" specifies that in the respective cyclopeptide, $Xaa^1$ is D-Tyr, the residue between $Xaa^1$ and $Xaa^2$ is derived from D-Orn, and R is Me.

Materials and Methods

All commercially available chemical reagents were used without further purification. Trityl resins were purchased from Pep Chem and amino acid derivatives from Iris Biotech GmbH, NovaBiochem, Merck, Bachem, Neosystem, Aldrich, while all other chemicals were bought from Aldrich, VWR, Fluka and Merck if not stated otherwise.

NMP was obtained from VWR and used without further distillation. Dry solvents were purchased from Aldrich, Fluka and Merck.

Analytical RP-HPLC was performed on a Nucleosil 100 C18 (5 μm, 125×4.0 mm) column (C S GmbH, Langerwehe, Germany) using a Sykam gradient HPLC System (Sykam GmbH, Eresing, Germany). The peptides were eluted applying different gradients of 0.1% (v/v) TFA (trifluoroacetic acid) in water (solvent A) and 0.1% TFA (v/v) in acetonitrile (solvent B) at a constant flow of 1 mL/min (specific gradients are cited in the text). UV-detection was performed at 220 nm using a 206 PHD UV-Vis detector (Linear™ Instruments Corporation, Reno, USA). Preparative RP-HPLC was performed on the same HPLC system using a Multospher 100 RP 18-5 (250×20 mm) column (C S GmbH, Langerwehe, Germany) at a constant flow of 9 mL/min.

ESI mass spectra were recorded on a Finnigan LCQ in combination with a Agilent/HP 1100 RP-HPLC system using a Omnicrom YMC ODS-A C18 column (120 Å, 3 μm, 125 mm=2 mm) with a flow rate of 0.2 mL/min. The eluent was a linear gradient from water to acetonitrile with 0.1% formic acid over 20 mM with detection at 220 nm.

NMR spectra were recorded on a Bruker Avance 250 or Bruker DMX 500 at 298K. The chemical shifts are reported in ppm on the ▫ scale relative to the solvent signal. $^{13}C$— NMR— spectra were recorded using $^{1}H$-broad band decoupling. Pulse programs were taken from the Bruker library or written by members of our group. Samples were prepared in tubes with a diameter of 5 mm using 0.5 ml of deuterated solvent with a final concentration of approximately 20-50 mM. The resulting spectra were processed on a PC workstation using Bruker TOPSPIN 1.3 and MestRe Nova software.
Synthesis of Cyclic Peptide Scaffolds (GP1)

Standard Fmoc strategy with the acid labile side chain protecting group 2,2,4,6,7- pentame-thyldihydrobenzofurane-5-sulfonyl (Pbf) for Arg and 4,4-dimethyl-2,6-dioxocyclohex-1-ylidene)ethyl (Dde) for D-Orn was employed to construct peptides on tritylchloridpolystyrene (TCP) Resin. O-(benzotriazol-1-yl)-N,N,N',N'-tetramethyluronium tetrafluoroborate (TBTU) and N-hydroxybenzotriazole (HOBt) were used as coupling reagents. N-alkylated amines were acylated using 2-(7-aza-1H-benzotriazole-1-yl)-1,1,3,3-tetramethyluronium hexafluorophosphate (HATU) with 1-hydroxy-7-azabenzotriazole (HOAt) as racemization suppressant. Gly was chosen as C-terminal residue to avoid racemization in the cyclization step and at the same time raise its yields by turn preformation of the N-terminal D-amino acid.

N-methylation was achieved via the Fukuyama-Mitsunobu reaction by treating Ns-protected amines with methanol under typical Mitsunobu conditions (diisopropylazodicarboxylate (DIAD) and triphenylphosphine) (Demmer et al., 2008). Ns was cleaved by treatment with 1,8-diazabicyclo[5.4.0]undec-7-ene (DBU) and 2-mercaptoethanol to yield the secondary amine.

D-Orn-N$^\alpha$-methylated peptides were prepared on the solid phase by Fmoc-deprotection of resin-bound Fmoc-D-Orn(Dde)-Arg(Pbf)-Nal-Gly, subsequent Ns-protection, N-methylation, Ns deprotection, attachment of Fmoc- D-(3-iodo)Tyr-OH or Fmoc-D-Tyr(tBU) Tyr(tBu)—OH with HATU/HOAt followed by Fmoc deprotection. Dde was chosen as orthogonal protecting group for the D-Orn-side-chain as it is—in contrast to Fmoc—stable under Mitsunobu as well as under alkaline Ns deprotection conditions.

D-Orn(Dde) protected peptides were cleaved from the resin with a mixture of acetic acid/2,2,2-trifluoroethanol/ DCM (3/1/6, v/v/v) and cyclized with DPPA and $NaHCO_3$ in DMF. Dde-protection was carried out usig 2% hydrazine in DMF. Coupling with the respective linker units was performed using the respective N-Fmoc-protected linker moiety and standard coupling conditions (HOBt, TBTU). Upon Fmoc-deprotection using 20% piperidine in DMF, peptides were reacted with unprotected DOTA in aqueous solution using N-hydroxysuccinimide and 1-Ethyl-3-(3-dimethylaminopropyl)carbodiimide as coupling reagents and DIPEA as the base. Final deprotection of acid labile groups was done in 95% trifluoroacetic acid (TFA) containing 2.5% $H_2O$ and 2.5% triisopropylsilane (TIPS) before RP-HPLC purification. ESI-MS was used to identify the peptides and the purity determined by analytical RP-HPLC was better than 95%. $^{nat}In$, $^{nat}Lu$, $^{nat}Ga$ and $^{nat}Bi$ complexation was carried out in 0.03 M HCl.

1. Loading of Tritylchloridpolystyrene (TCP) Resin. Peptide synthesis was carried out using TCP-resin (0.9 mmol/g) following standard Fmoc-strategy. Fmoc-Xaa-OH (1.2 eq.) were attached to the TCP resin with DIEA (2.5 eq.) in anhydrous DCM (0.8 mL/g resin) at room temperature for 1 h. The remaining trityl chloride groups were capped by addition of 1 mL/g(resin) of a solution of MeOH, DIEA (5:1; v:v) for 15 min. The resin was filtered and washed 5 times with DCM and 3 times with MeOH. The loading capacity was determined by weight after drying the resin under vacuum and ranged from 0.4-0.9 mmol/g.

2. On-Resin Fmoc Deprotection. The resin-bound Fmoc peptide was treated with 20% piperidine in NMP (v:v) for 10 minutes and a second time for 5 minutes. The resin was washed 5 times with NMP.

3. TBTU/HOBt Coupling. A solution of Fmoc-Xaa-OH (2 eq.), TBTU (2 eq.), HOBt (2 eq.), DIEA (5.2 eq.) in NMP (1 mL/g resin) was added to the resin-bound free amine peptide and shaken for 60 min at room temperature and washed 5 times with NMP.

4. N-Methylation under Mitsunobu Conditions. A solution of triphenylphosphine (5 eq.), DIAD (5eq.) and MeOH (10 eq.) in dry THF (1 mL/g resin) was added to the resin-bound Ns protected peptides and shaken at room temperature for 10 minutes. The resin was filtered off, and washed 3 times with dry THF and 3 times with NMP.

6. HATU/HOAt Coupling. A solution of Fmoc-Xaa-OH or tris(t-Bu)DOTA (2 eq.), HA-TU (2 eq.), HOAt (2 eq.), DIEA (4 eq.) in NMP (1 mL/g resin) was added to the resin-bound peptides and shaken for 3 hours at room temperature and washed 5 times with NMP.

7. On-Resin Ns Deprotection. For Ns deprotection, the resin-bound Ns-peptides were stirred in a solution of mercaptoethanol (10 eq.) and DBU (5 eq.) in NMP (1 mL/g resin) for 5 minutes. The deprotection procedure was repeated one more time and the resin was washed 5 times with NMP.

8. Peptide Cleavage. For complete cleavage from the resin the peptides were treated three times with a mixture of acetic acid/2,2,2-trifluoroethanol/DCM (3/1/6, v/v/v) at room temperature for half an hour and the solvents were evaporated under reduced pressure.

9. Cyclization. To a solution of peptide in DMF (1 mM peptide concentration) and Na—HCO3 (5 eq.) DPPA (3 eq.) was added at RT and stirred over night or until no linear peptide could be observed by ESI-MS. The solvent was evaporated to a small volume under reduced pressure and the peptides precipitated in saturated NaCl solution and washed two times in HPLC grade water.

10. Removal Dde Protecting Groups. Dde-protection was carried out usig 2% hydrazine in DMF at room temperature. After 30 mM, deprotected peptides were precipitated using water (Pbf/tBu-protected peptides) or diethyl ether (deprotected peptides) and dried in a desiccator before further functionalization.

11. Coupling of linker units. A solution of Fmoc-Linker (2 eq.), TBTU (2 eq.), HOBt (2 eq.), DIEA (5.2 eq.) in DMF was added to a solution of D-Orn-Dde-deprotected peptide in DMF (1 eq) and stirred for 30-60 mM at RT. The product was then precipitated in saturated NaCl solution and washed two times in HPLC grade water.

12. DOTA coupling. DOTA (1 eq) was preactivated with NHS (N-hydroxysuccinimide, 1.25 eq), EDCI (1-ethyl-3-(3-dimethylaminopropyl)carbodiimide, 1.25 eq) and DIPEA (2 eq) in water (1 mL/0.3 mmol) for a minimum of 30 mM. Then, the respective peptide dissolved in DMF (1 mL per 0.15 mmol of peptide) was slowly added under vigorous stirring and the mixture was stirred for 2-4 h at RT, and then the solvents were evaporated to dryness [M. Schottelius, M. Schwaiger, H. J. Wester, Tetrahedron Letters 44 (2003) 2393-2396].

13. Removal of Acid Labile Side Chain Protecting Groups. Cyclized peptides were stirred in a solution of TFA, water and TIPS (95:2.5:2.5; v:v:v) at room temperature for one hour or until no more protected peptide could be observed by ESI-MS and precipitated in diethyl ether and washed two more times.

14. Formation of $^{nat}$In, $^{nat}$Lu, $^{nat}$Ga and $^{nat}$Bi complexes. Peptides were dissolved in water to yield a 2 mM solution. For metal complexation, an equal volume of a 5-20 mM solution of the respective metal salt in 0.06 M HCl was added, and the mixture was heated for 30 min to 95° C. Quantitative metal incorporation was confirmed using ESI-MS.

Synthetic Description for Individual Compounds:

N-Fmoc-5-aminopentanoic acid (Fmoc-AVS). 5-aminopentanoic acid (0.35 g, 3 mmol) was reacted with o-Fmoc-OSu (1.01 g, 3 mmol) in DMF for 60 min. Fmoc-AVS was obtained as a slightly yellow, sticky oil in sufficient) purity (0.92 g, 90%). $^1$H NMR (500 MHz, DMSO-d$_6$): ☐ 12.02 (br s, 1H), 7.86 (d, 2 H), 7.67 (d, 2H), 7.39 (t, 2H), 7.31 (t, 2H), 7.26 (t, 1H), 4.28 (d, 2H), 4.19 (t, 1H), 2.97 (dd, 2H), 2.19 (t, 2H), 1.43 (br m, 4H). $^{13}$C NMR (125 MHz, DMSO-d$_6$): 174.9, 156.7, 144.4, 141.2, 128.0, 127.5, 125.6, 120.5, 65.6, 64, 47.2, 33.8, 29.3, 22.2. R$_t$ (10-100%): 20.73 min. m/z calculated for C$_{20}$H$_{21}$NO$_4$: 339.15; found 701.3 [2M+Na$^+$].

yorn'(DOTA)RNalG and (3-iodo)yorn'(DOTA)RNalG

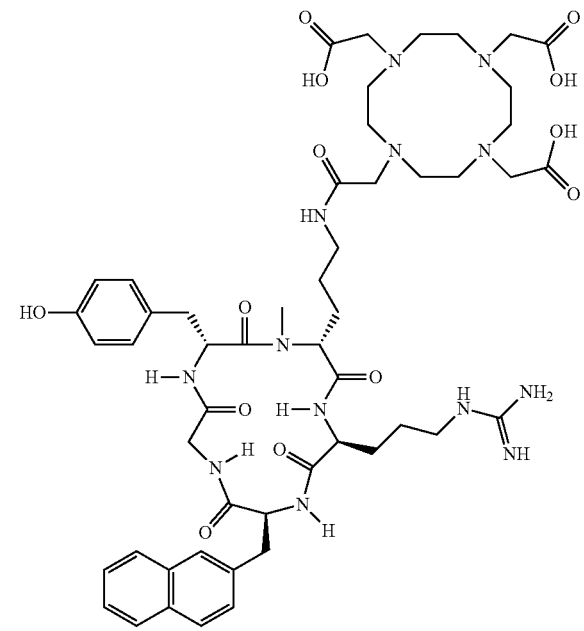

Chemical Formula: C$_{52}$H$_{73}$N$_{13}$O$_{13}$
Exact Mass: 1087,55

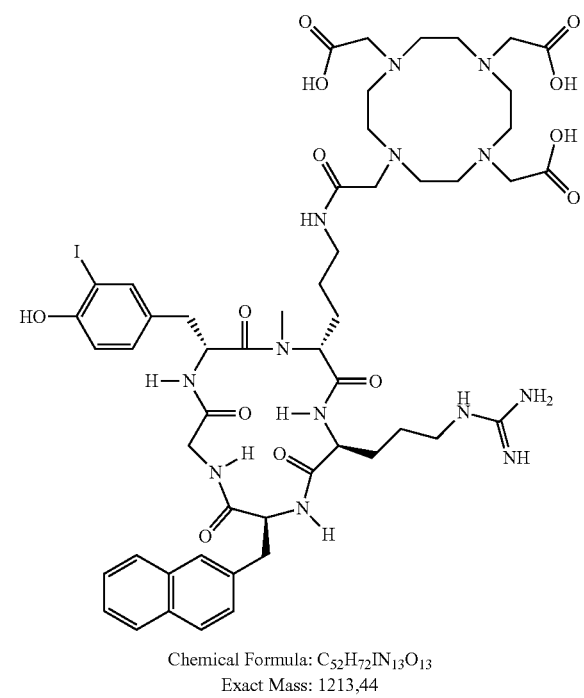

Chemical Formula: C$_{52}$H$_{72}$IN$_{13}$O$_{13}$
Exact Mass: 1213,44

Synthesis of the respective Dde-deprotected, cyclic peptides y(tBu)om'R(Pbf)NalG and (3-iodo)yorn'R (Pbf)NalG was carried out according to the general procedures outlined above (GP1). Upon DOTA-coupling (12), the acid labile protecting groups were removed (13) and the peptides were purified using preparative RP-HPLC.

yorn'CABS, DOTA)RNalG and (3-iodo)yorn'(ABS, DOTA)RNalG

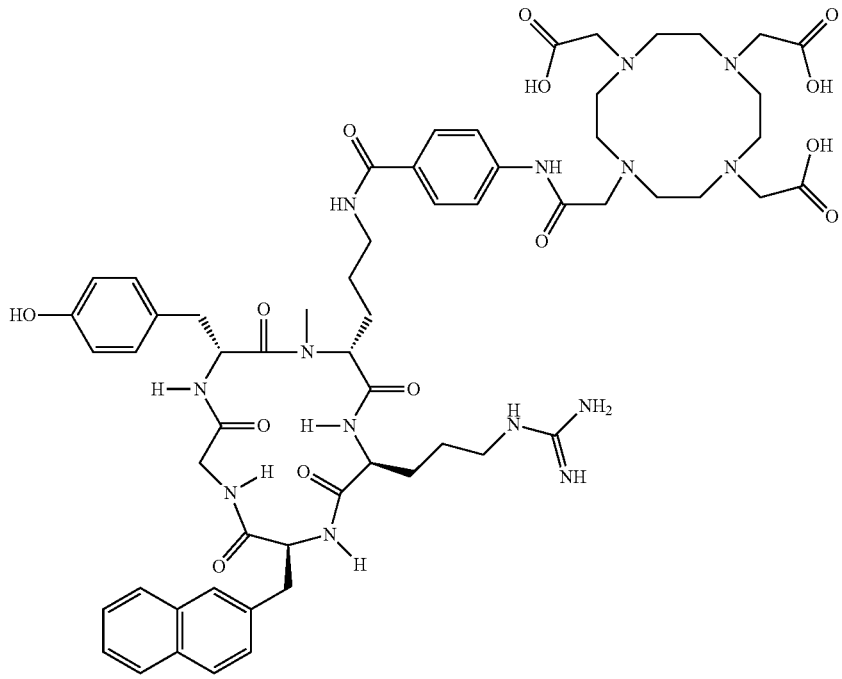

Chemical Formula: $C_{59}H_{78}N_{14}O_{14}$
Exact Mass: 1206,58

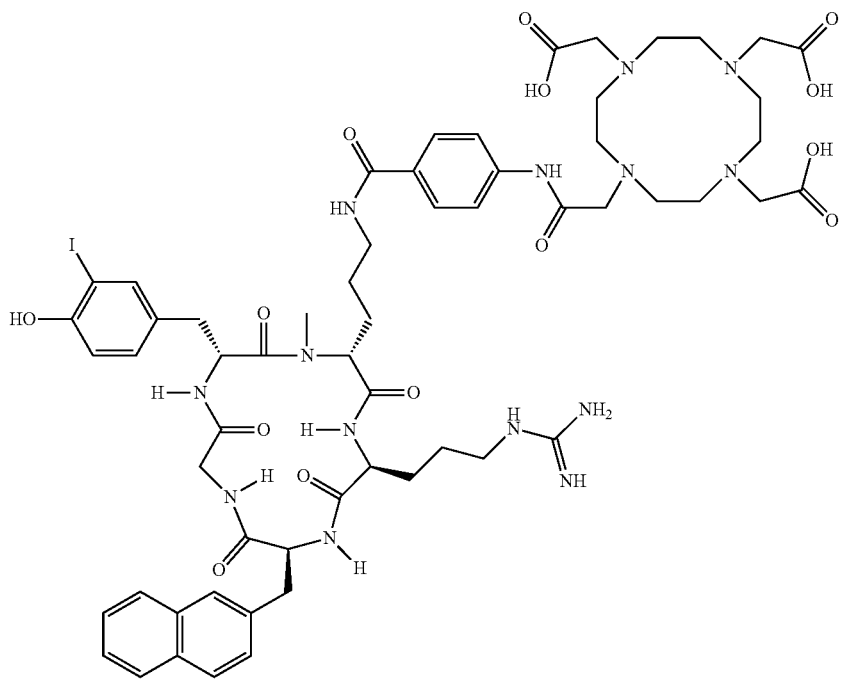

Chemical Formula: $C_{59}H_{77}IN_{14}O_{14}$
Exact Mass: 1332,48

Synthesis of the respective Dde-deprotected, cyclic peptides y(tBu)orn'R(Pbf)NalG and (3-iodo)yorn'R(Pbf)NalG was carried out according to the general procedures outlined above (GP1). Fmoc-ABS was coupled according to procedure 11. Upon Fmoc-deprotection using 20% piperidine in DMF, the crude peptides were precipitated using water and dried. After DOTA-coupling (12), the acid labile protecting groups were removed (13) and the peptides were purified using preparative RP-HPLC.

yorn'(AMBS, DOTA)RNalG and (3-iodo)yorn'(AMBS, DOTA)RNalG was carried out according to the general procedures outlined above (GP1). Fmoc-AMBS was coupled according to pro-

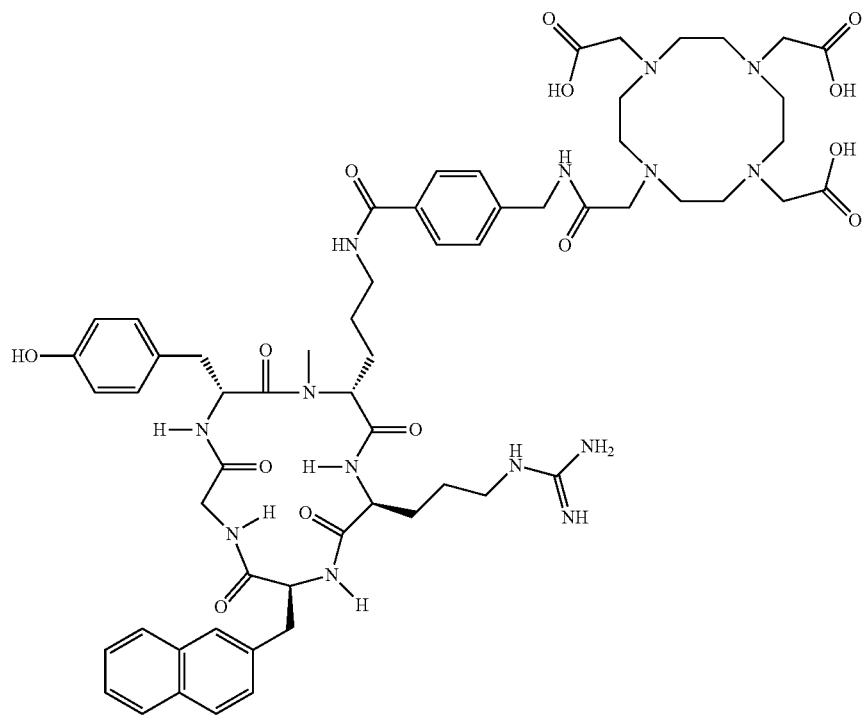

Chemical Formula: $C_{60}H_{80}N_{14}O_{14}$
Exact Mass: 1220,60

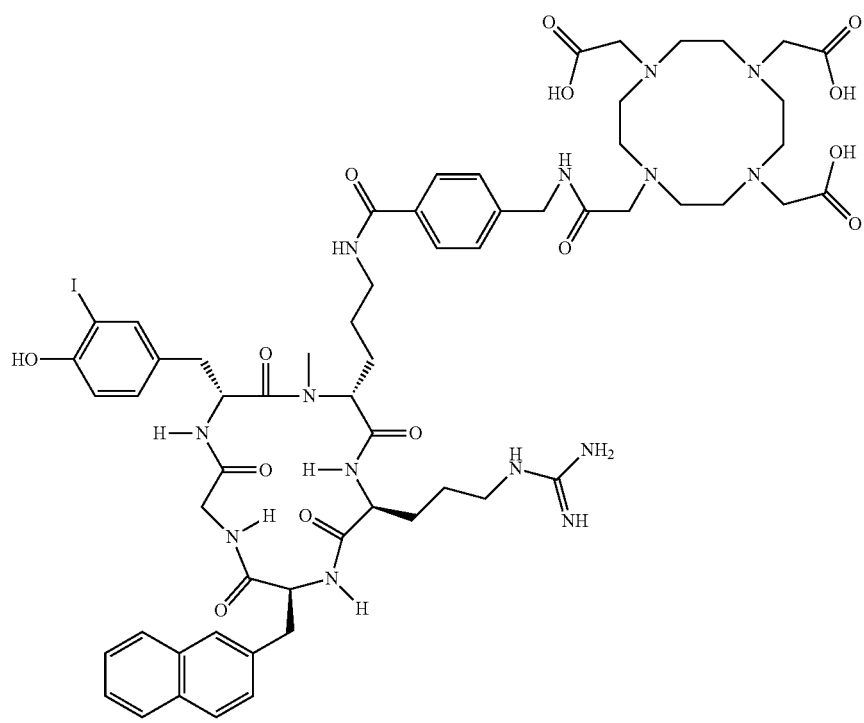

Chemical Formula: $C_{60}H_{79}IN_{14}O_{14}$
Exact Mass: 1346,49

Synthesis of the respective Dde-deprotected, cyclic peptides y(tBu)orn'R(Pbf)NalG and (3-iodo)yorn'R(Pbf)NalG cedure 11. Upon Fmoc-deprotection using 20% piperidine in DMF, the crude peptides were precipitated using water and dried. After DOTA-coupling (12), the acid labile protecting groups were removed (13) and the peptides were purified using preparative RP-HPLC.

yorn'(ABS, G, DOTA)RNalG and (3-iodo)yorn'(ABS, G, DOTA)RNalG

Synthesis of the respective Dde-deprotected, cyclic peptides y(tBu)orn'R(Pbf)NalG and (3-iodo)yorn'R(Pbf)NalG was carried out according to the general procedures outlined above (GP1). Upon coupling of Fmoc-ABS (11), Fmoc-deprotection using 20% piperidine in DMF, coupling of

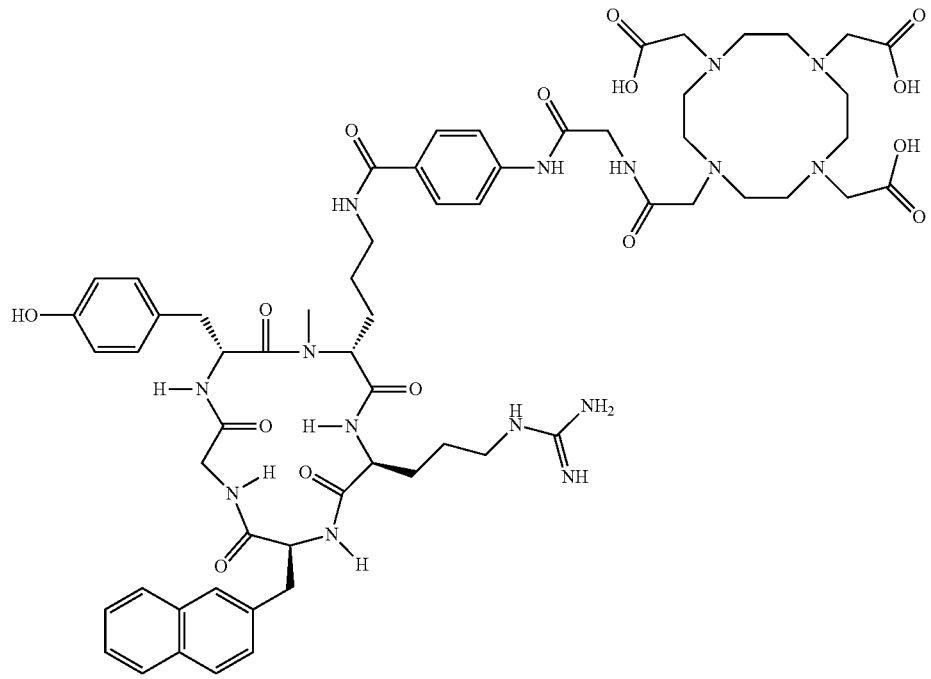

Chemical Formula: $C_{61}H_{81}N_{15}O_{15}$
Exact Mass: 1263,60

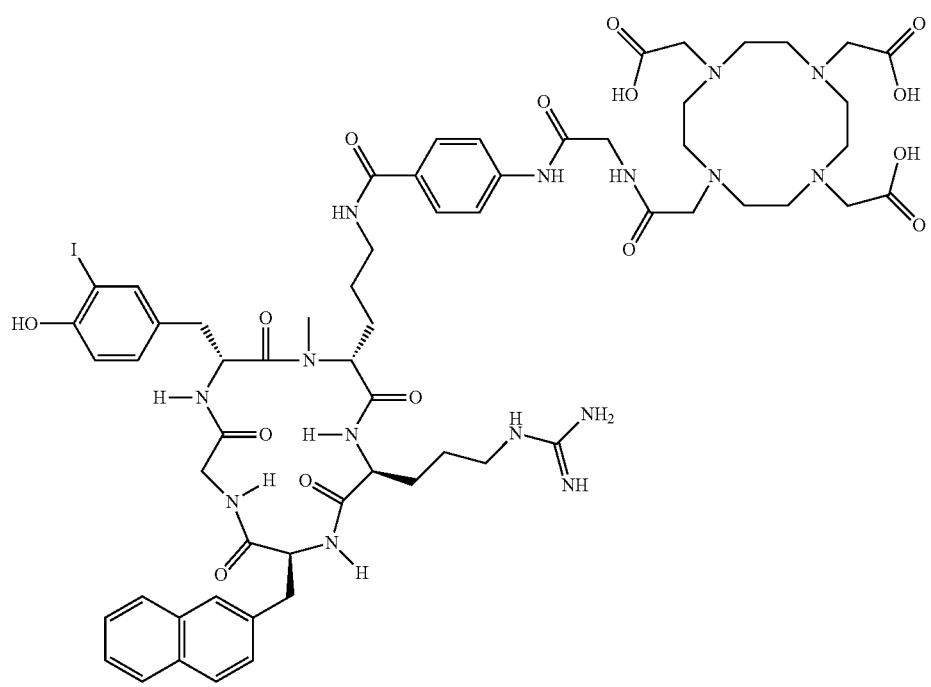

Chemical Formula: $C_{61}H_{80}IN_{15}O_{15}$
Exact Mass: 1389,50

Fmoc-Gly (11) and subsequent Fmoc-deprotection, the crude peptides were precipitated using water and dried. After DOTA-functionalization (12), the acid labile protecting groups were removed (13) and the peptides were purified using preparative RP-HPLC.

yorn'(ABS, beta-Ala, DOTA)RNalG and (3-iodo)yorn' (ABS, beta-Ala, DOTA)RNalG

Synthesis of the respective Dde-deprotected, cyclic peptides y(tBu)orn'R(PbONalG and (3-iodo)yorn'R(Pbf)NalG was carried out according to the general procedures outlined above (GP1). Upon coupling of Fmoc-ABS (11), Fmoc-deprotection using 20% piperidine in DMF, coupling of Fmoc-beta-Ala (11) and subsequent Fmoc-deprotection, the crude peptides were precipitated using water and dried. After

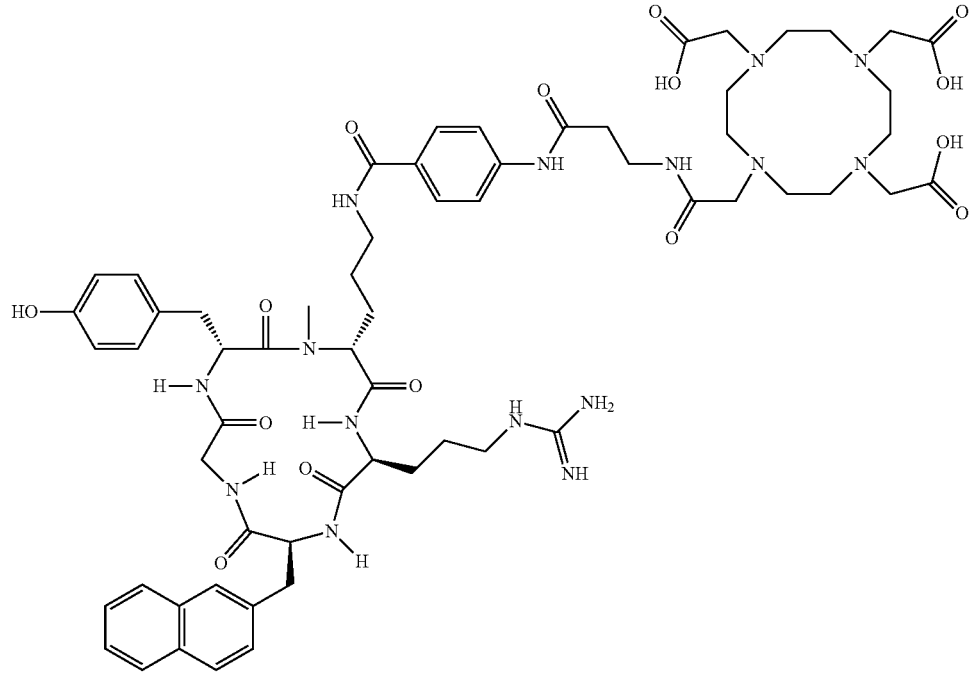

Chemical Formula: $C_{62}H_{83}N_{15}O_{15}$
Exact Mass: 1277,62

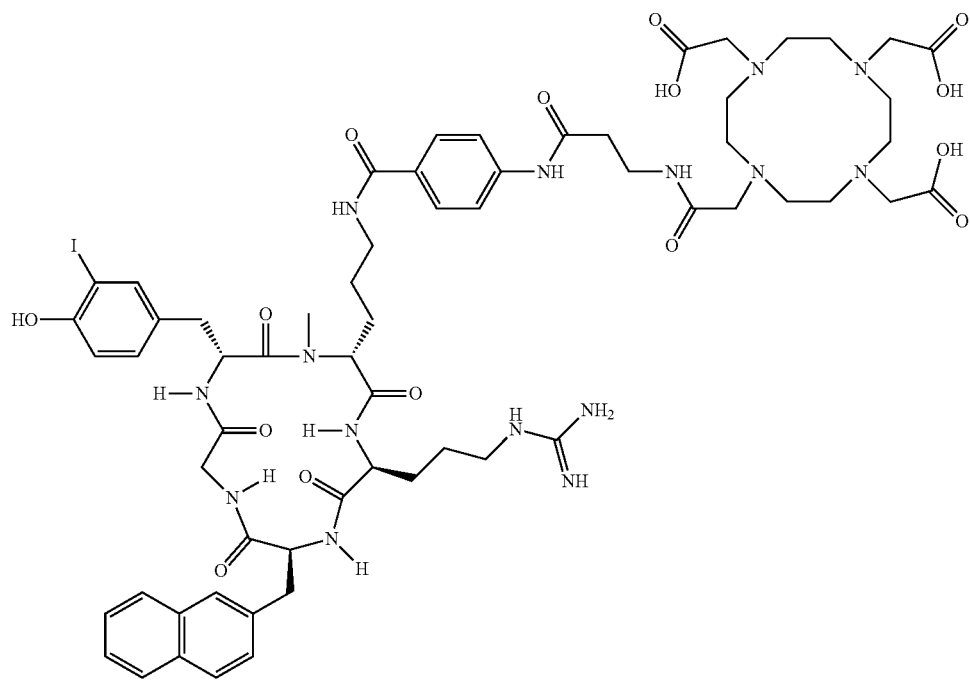

Chemical Formula: $C_{62}H_{82}IN_{15}O_{15}$
Exact Mass: 1403,52

DOTA-functionalization (12), the acid labile protecting groups were removed (13) and the peptides were purified using preparative RP-HPLC.

yorn'(ABS, Avs, DOTA)RNalG and (3-iodo)yorn'(ABS, Avs, DOTA)RNalG

Synthesis of the respective Dde-deprotected, cyclic peptides y(tBu)orn'R(Pbf)NalG and (3-iodo)yorn'R(Pbf)Nalg was carried out according to the general procedures outlined above (GP1). Upon coupling of Fmoc-ABS (11), Fmoc-deprotection using 20% piperidine in DMF, coupling of

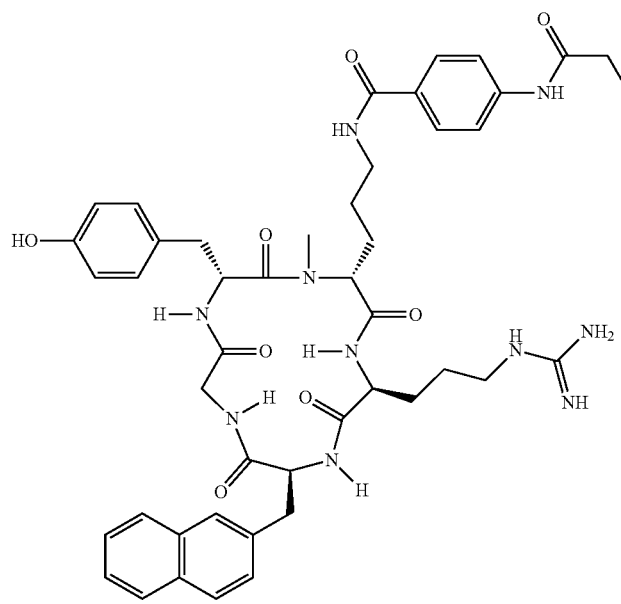

Chemical Formula: $C_{64}H_{87}N_{15}O_{15}$
Exact Mass: 1305,65

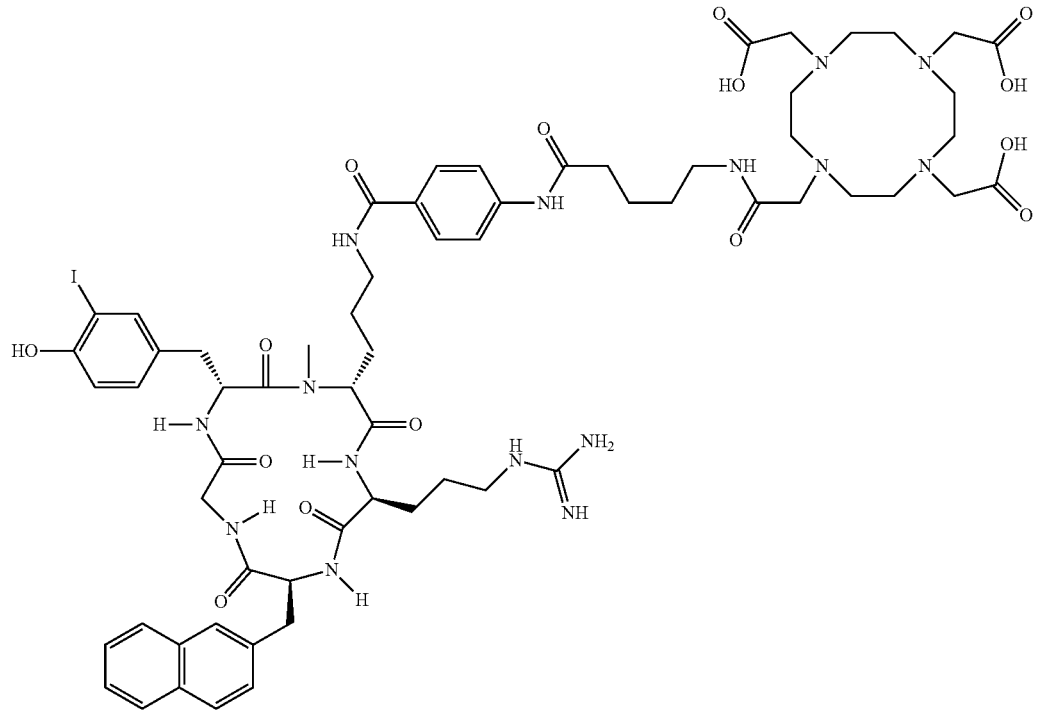

Chemical Formula: $C_{64}H_{86}IN_{15}O_{15}$
Exact Mass: 1431,55

Fmoc-Avs-OH (11) and subsequent Fmoc-deprotection, the crude peptides were precipitated using water and dried. After DOTA-functionalization (12), the acid labile protecting groups were removed (13) and the peptides were purified using preparative RP-HPLC.

yorn'(ABS, Ahx, DOTA)RNalG and (3-iodo)yorn'(ABS, Ahx, DOTA)RNalG

Synthesis of the respective Dde-deprotected, cyclic peptides y(tBu)orn'R(Pbf)NalG and (3-iodo)yorn 'R(Pbf)NalG was carried out according to the general procedures outlined above (GP1). Upon coupling of Fmoc-ABS (11), Fmoc-deprotection using 20% piperidine in DMF, coupling of Fmoc-Ahx-OH (11) and subsequent Fmoc-deprotection, the crude peptides were precipitated

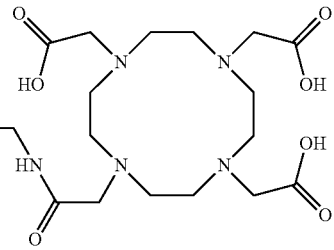

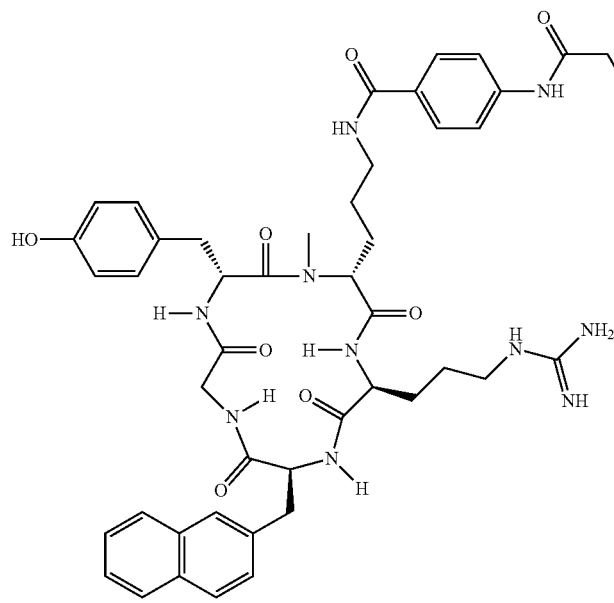

Chemical Formula: $C_{65}H_{89}N_{15}O_{15}$
Exact Mass: 1319,67

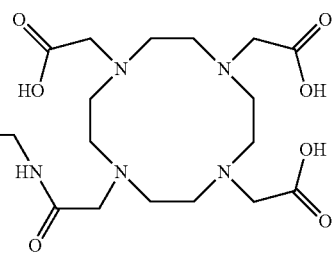

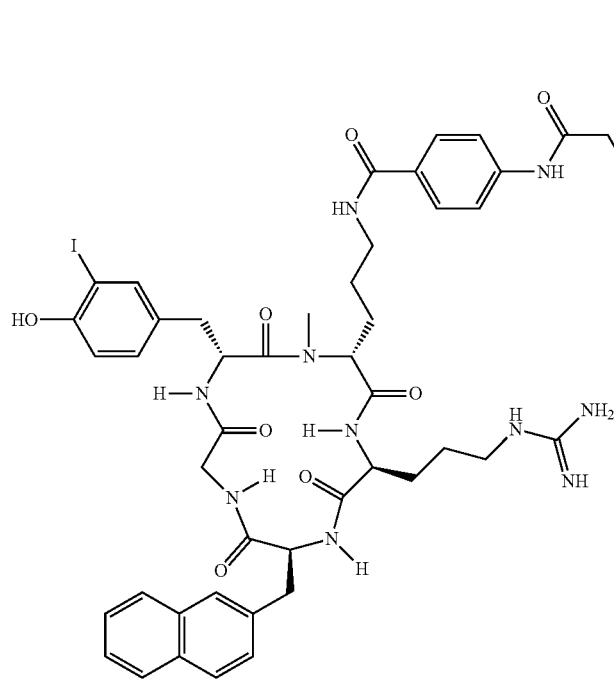

Chemical Formula: $C_{65}H_{88}IN_{15}O_{15}$
Exact Mass: 1445,56 using water and dried. After DOTA-functionalization (12), the acid labile protecting groups were removed (13) and the peptides were purified using preparative RP-HPLC.

yorn'(Avs, Avs, DOTA)RNalG and (3-iodo)yorn'(Avs, Avs, DOTA)RNalG

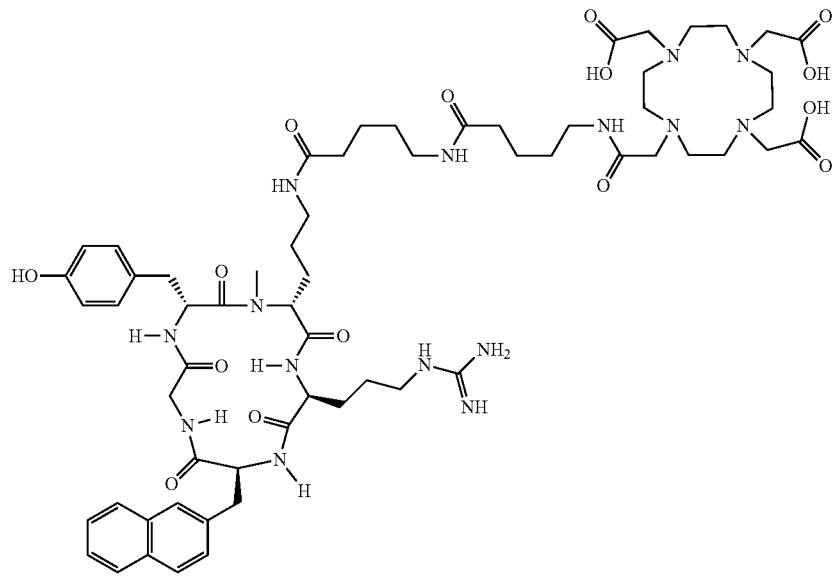

Chemical Formula: C$_{62}$H$_{91}$N$_{15}$O$_{15}$
Exact Mass: 1285,68

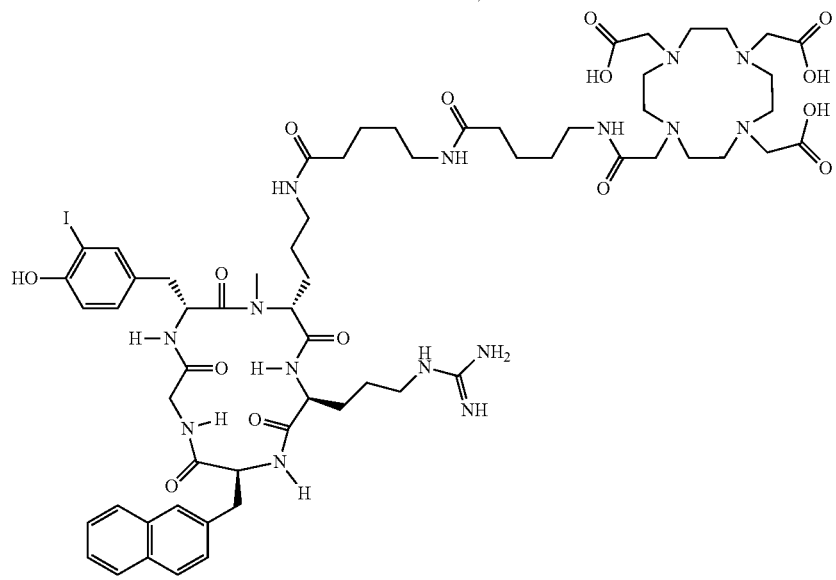

Chemical Formula: C$_{62}$H$_{90}$IN$_{15}$O$_{15}$
Exact Mass: 1411,58

Synthesis of the respective Dde-deprotected, cyclic peptides y(tBu)orn'R(Pbf)NalG and (3-iodo)yorn'R(Pbf)NalG was carried out according to the general procedures outlined above (GP1). Upon coupling of Fmoc-Avs-OH (11), Fmoc-deprotection using 20% piperidine in DMF, coupling of Fmoc-Avs-OH (11) and subsequent Fmoc-deprotection, the crude peptides were precipitated using water and dried. After DOTA-functionalization (12), the acid labile protecting groups were removed (13) and the peptides were purified using preparative RP-HPLC.

yorn'(G, Trigas, DOTA)RNalG and (3-iodo)yorn'(G, Trigas, DOTA)RNalG

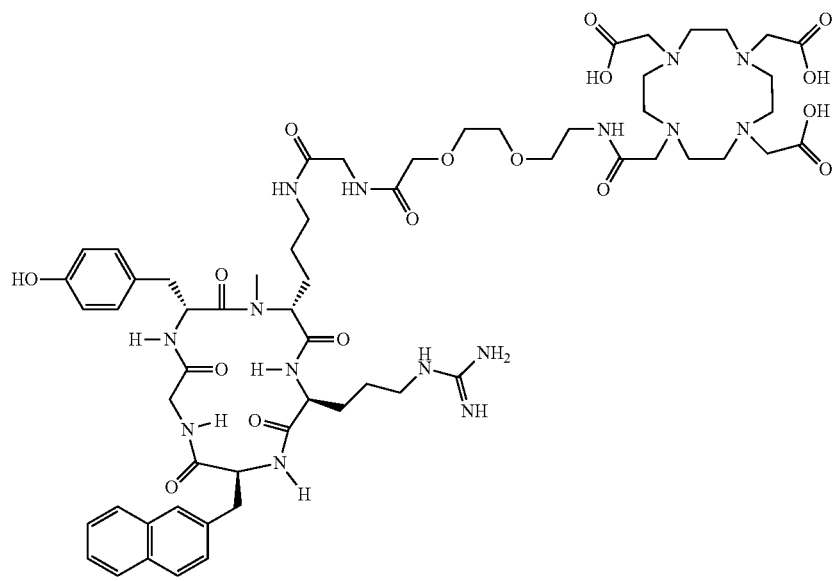

Chemical Formula: $C_{60}H_{87}N_{15}O_{17}$
Exact Mass: 1289,64

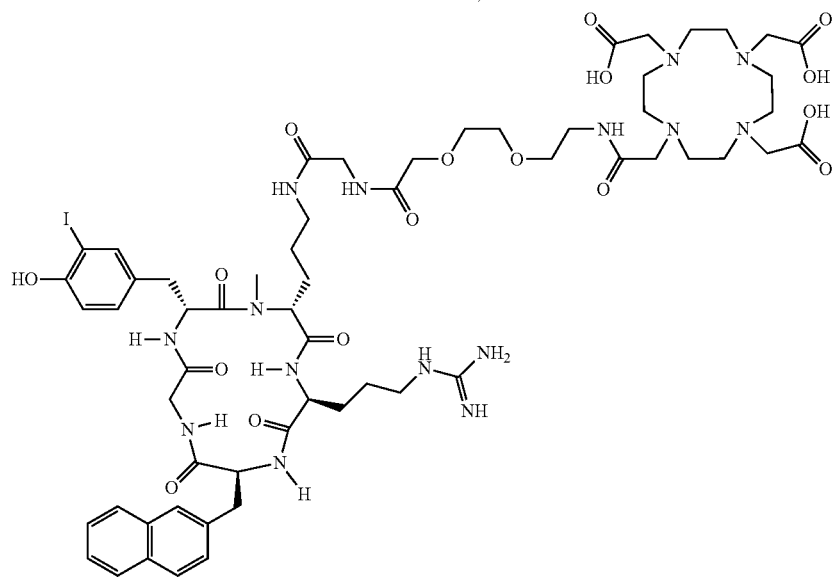

Chemical Formula: $C_{60}H_{86}IN_{15}O_{17}$
Exact Mass: 1415,54

Synthesis of the respective Dde-deprotected, cyclic peptides y(tBu)orn'R(Pbf)NalG and (3-iodo)yorn'R(Pbf)NalG was carried out according to the general procedures outlined above (GP1). Upon coupling of Fmoc-Gly-OH (11), Fmoc-deprotection using 20% piperidine in DMF, coupling of Fmoc-Trigas-OH (11) and subsequent Fmoc-deprotection, the crude peptides were precipitated using water and dried. After DOTA-functionalization (12), the acid labile protecting groups were removed (13) and the peptides were purified using preparative RP-HPLC.

Radiolabelling

Radioiodination

The different cold metal complexes of the Tyr$^1$-peptides were radioiodinated using the IodoGen® method. Briefly, 100-200 µg of peptide were dissolved in 0.5 mL TRIS iodination buffer (25 mM Tris·HCl, 0.4 M NaCl, pH 7.5) and transferred to an Eppendorf reaction tube coated with 150 µg of IodoGen®. Upon addition of [$^{125}$I]NaI (18-20 MBq, Hartmann Analytik, Braunschweig, Germany), the reaction vessel was briefly vortexed and the labeling reaction was allowed to proceed for 15 min at RT. The peptide solution was then removed from the insoluble oxidizing agent. Separation of the respective radioiodinated product from unlabeled precursor was achieved using gradient RP-HPLC (column:

Nucleosil 100 C18 (5 µm, 125×4.0 mm; C S GmbH, Langerwehe, Germany), gradient: 22-42% ethanol (0.5% acetic acid) in water (0.5% acetic acid) within 20 min, flow: 1 mL/min).

For in vitro binding and uptake studies, the HPLC product fraction was used as such and diluted to the required concentration using the respective assay medium. For biodistribution experiments, excess ethanol was removed by bubbling an argon stream through the product fraction at 90° C. for 20 min. [$^{125}$I]pentixather was then reconstituted to an activity concentration of app. 1 MBq/100 μL using PBS and was then used for the in vivo study.

$^{68}$Ga-Labelling yorn'(AMBS, DOTA, $^{68}$Ga)RNalG was prepared in a GallElut+ (SCINTOMICS GmbH, Germany) module according to a previously published procedure [Notni J, Simecek J, Hermann P, Wester H J. Chem-Eur J. 2011; 17:14718-14722]. Briefly, a $_{68}$Ge/$^{68}$Ga generator with SnO$_2$ matrix (iTHEMBA LABS, South Africa) was eluted with 1 M HCl. The fraction with the highest activity concentration (1.25 mL) was mixed with precursor peptide (3.5 nmol) and aq. HEPES (0.8 mL, 2.7 M) in a conical 5 mL glass vial (AllTech). The solution (pH 3) was heated at 100° C. for 5 min and was passed through a SPE cartridge (Waters SepPak C18 classic). The cartridge was washed with water (10 mL) to remove unbound $^{68}$Ga$^{3+}$, inorganic ions and HEPES, and finally purged with air. The product was eluted with ethanol (1 mL) into a 10 mL flask; water (2 mL) and PBS (1 mL) were added. Aliquots of this formulation were directly used for in vitro binding assays; for in vivo studies, the product solution was concentrated in vacuo to a final volume of app. 1 mL. Radio-chemical purity of yorn'(AMBS, DOTA, $^{68}$Ga)RNalG was determined by radio-TLC and radio-HPLC.

$^{177}$Lu/$^{111}$In-Labelling

Labelling of DOTA-peptides with $^{177}$Lu and $^{111}$In is an established procedure and was carried out according to the literature [Breeman W A, De Jong M, Visser T J, Erion J L, Krenning E P. Eur J Nucl Med Mol Imaging. 2003 June; 30(6):917-20.]

Determination of Lipophilicity

To a solution of app. 2 kBq of radiolabeled peptide in 500 tiL of PBS (pH 7.4), 500 μL of octanol were added (n=6). Vials were vortexed vigorously for 3 min. To achieve quantitative phase separation, the vials were centrifuged at 14,000×g for 6 min in a Biofuge 15 (Heraeus Sepatech, Osterode, Germany). The activity concentrations in 100 μL-samples of both the aqueous and the organic phase were measured in a γ-counter. Both the partition coefficient $P_{ow}$, which is defined as the molar concentration ratio of a single species A between octanol and an aqueous phase at equilibrium, and log $P_{ow}$, which is an important parameter used to characterize lipophilicity of a compound, were calculated.

Biological Assays

Cell Culture

Jurkat human T lymphocyte cells and SH—SY5Y human neuroblastoma cells were maintained in RPMI 1640 medium supplemented with 10% fetal calf serum (FCS). Daudi cells (human Burkitt's B-cell lymphoma) were grown in RPMI-1640 medium supplemented with 10% FCS, 2 mM L-glutamine, 1% non-essential amino acids, 0.1% □ Mercaptoethanol. SU-DHL-8 (human large cell lymphoma) cells were maintained in RPMI-1640 medium supplemented with 20% FCS, 2 mM L-glutamine, 1% non-essential amino acids, 0.1% □ Mercaptoethanol. The colon carcinoma cell line HT-29, the breast cancer cell line MCF-7 and DU-145 prostate carcinoma cells were cultured in DMEM supplemented with 10% FCS. CHO—K1 cells (Chinese hamster ovary cells, DSMZ) were cultivated in RPMI-1640 medium supplemented with 10% FBS, 2 mM L-glutamine, and 100 units/mL of penicillin/streptomycin. All cell lines were cultured at 37° C. in a humidified 5% CO$_2$ atmosphere. Media and supplements were obtained from Biochrom (Berlin, Germany) or Gibco (life technologies, Darmstadt, Germany).

In the assay medium used for internalization studies, FCS was replaced by 5% bovine serum albumin (BSA; Sigma, St. Louis, USA). For cell counting, a Countesse automated cell counter (Invitrogen, Carlsbad, USA) was used.

Determination of ICso

For IC$_{50}$ determination, samples containing 2×10$^5$ Jurkat cells in HBSS/0.2% Bovine Serum rum Albumin (BSA) were incubated with 100.000 cpm [$^{125}$I]FC131 (cyclo(-D-Tyr$^1$[$^{125}$I]-Arg$^2$-Arg$^3$-Nal$^4$-Gly$^5$, approx. 0.1 nM) in the presence of increasing concentrations ($10^{-11}$ to $10^{-5}$ M) of the non-radioactive compound of interest (n=3 per concentration). The total sample volume was 250 μL. After incubation at room temperature (RT) for 120 min with gentle agitation (200 mot/min), the tubes were centrifuged (5 min, 447 g, Megafuge 1.0, Heraeus Thermo Scientific) and the supernatant was carefully removed. After washing twice with 400 piL of cold PBS, the amount of bound radioligand was quantified using a γ-counter. Nonspecific binding was determined in the presence of 1 μM FC131. IC$_{50}$ values were calculated using the PRISM 4 program (Graph Pad Software, San Diego, Calif.).

Determination of "inverse IC$_{50}$" for $^{125}$I-labelled M$^{3+}$- and AlF$^{2+}$-complexes Experiments were performed in analogy the determination of IC$_{50}$. However, instead of using a standard radioligand and varying concentrations of the compound of interest as the competitor, the different radioiodinated peptides of interest were assayed against a standard competitor, i.e. unlabeled FC-131.

Determination of Binding Selectivity and Binding Specificity (Dual Tracer Experiment)

Transient transfection with hHACXCR4, mCXCR4, mHACXCR4, hCXCR7, mCXCR7 and mHACXCR7 was accomplished using jetPRIME reagent (PEQLAB Biotechnology, Erlangen, Get many; #13-114) according to manufacturer's instructions. CHO—K1 cells were seeded at a density of 50000 cells/well in poly-L-lysine-coated 24-well plates, transfected with 0.5 μg/well of receptor-encoding constructs (kindly supplied by Prof. Dr. S. Schulz and Prof. Dr. R. Stumm, Institute of Pharmacology and Toxicology, Jena University Hospital, Germany) 16 h after plating, and used for assay 24 h after transfection. Receptor expression levels were quantified using flow cytometry. The human CXCR4-receptor was only available with an N-terminal haemagglutinin (HA)-tag. To demonstrate the independence of ligand binding of the presence or absence of a HA-tag on the receptor protein, a comparative evaluation of the murine receptors with and without the HA-tag was performed.

On the day of the experiment the transfection medium was removed, and the cells were left to equilibrate in 200 μL of assay medium (RPMI+5% BSA) at 37° C. for a minimum of 15 min before the experiment. Untransfected CHO cells (negative control), were treated identically. Then, 25 μL/well of either assay medium (Control) or of a 1 mM solution of AMD3100 in HBSS (Hank's buffered salt solution, Biochrom; determination of non-specific binding) were added (n=3, respectively, for each receptor construct), followed by the addition of 25 μL of assay medium containing yorn'(AMBS, DOTA, $^{68}$Ga)RNalG and [$^{125}$I]yorn'(AMBS, DOTA, Ga)RNalG. Final concentrations of the radioligands were 1 and 0.1 nM, respectively.

Upon incubation at 37° C. for 30 min, the incubation medium was removed, and cells were rinsed twice with 200 μL of HBSS and lysed using 200 μL of 1 N NaOH. The lysate was transferred to vials and combined with 200 μL of HBSS used for rinsing the wells. Quantification of the amount of free and bound activity was performed in an Automatic Gamma Counter (WALLAC; 1480 WIZARD™ 3").

Dual Tracer Internalization Study (Suspension Cells)

In the case of the suspension cell lines (Jurkat, Daudi, SUDHL-8), samples containing $2 \cdot 10^5$ cells in assay medium were coincubated with yorn'(AMBS, DOTA, $^{68}$Ga)RNalG (1 nM) and [$^{125}$I]yorn'(AMBS, DOTA, Ga)RNalG (0.1 nM) at 37° C. for different time points up to 60 min in the absence (total binding) or presence (non-specific binding) of 100 μM AMD3100 (n=3, respectively, per time point). The total sample volume was 250 μL. After incubation, the tubes were centrifuged (3 min, 1300 rcf, Megafuge 1.0, Heraeus Thermo Scientific), the supernatant was carefully removed and combined with 200 μL of ice cold HBSS used for washing the cells (free radioligand). To remove surface bound (acid releasable) radioactivity, cells were then washed twice with ice cold acid wash buffer (0.02 M NaOAc in saline buffered with AcOH to pH=5). Finally, the amount of internalized activity in the cell pellet as well as the fraction of free and acid releasable $^{68}$Ga-activity were determined using a γ-counter. Quantification of the respective $^{125}$I-activities was performed 24 h later.

Dual Tracer Internalization Study (Adherent Cells)

On the day prior to the experiment, cells (HT-29, MCF-7, SH—SY5Y, DU-145) were seeded in 24-well-plates at a density of app. $2 \cdot 10^5$ cells per well. On the day of the experiment, the culture medium was removed and the cells were washed once with 250 μL of unsupplemented medium before being left to equilibrate in 200 μL of assay medium at 37° C. for a minimum of 15 min before the experiment. Cells were then coincubated with yorn'(AMBS, DOTA, $^{68}$Ga)RNalG (1 nM) and [$^{125}$I]yorn'(AMBS, DOTA, Ga)R-NalG (0.1 nM) in the absence (total binding) or presence (non-specific binding) of 100 μM AMD3100 for different time points up to 60 min at 37° C. (n=3 wells, respectively, per time point). Incubation was terminated by placing the plate on an ice pack for app. 1 min and by subsequent removal of the incubation medium. Cells were thoroughly rinsed with 250 μL of HBSS. After washing twice with 250 μL of ice cold acid wash buffer (0.02 M NaOAc buffered with AcOH to pH=5), cells were lysed with 250 μL of 1 N NaOH. The lysate was transferred to vials and combined with 250 μL of HBSS used for rinsing the wells. Quantification of the amount of free, acid-releasable and internalized activity was performed as described.

Dual Tracer Externalization Study (Suspension Cells)

As in the previous experiment, cells were incubated with yorn'(AMBS, DOTA, $^{68}$Ga)RNalG (1 nM) and [$^{125}$I]yorn' (AMBS, DOTA, Ga)RNalG (0.1 nM) at 37° C. for 30 min and washed with HBSS. To ensure receptor integrity, no acid wash was performed after this initial internalization incubation. Then, to determine the extent of ligand recycling, two different experiments were performed. In the experiment allowing ligand recycling, 250 μL of assay medium were added to each well. In the experiment inhibiting ligand recycling, 250 μL of assay medium containing 100 μM AMD3100 were added to each well. Experiments were carried out in triplicate for both experimental conditions. Subsequently, the cells were incubated for 5, 15, 30 and 60 minutes at 37° C. Then, the tubes were centrifuged, the supernatant was removed and combined with 250 μL of HBSS used for washing the cells. This fraction represents the amount of externalized ligand. The following steps, i.e. acid wash and quantification of the remaining cellular activity, were performed as described for the internalization experiment.

Dual Tracer Externalization Study (Adherent Cells)

To determine ligand washout and recycling kinetics, cells were first coincubated with yorn'(AMBS, DOTA, $^{68}$Ga) RNalG (1 nM) and [$^{125}$I]yorn'(AMBS, DOTA, Ga)RNalG (0.1 nM) at 37° C. for 30 min and washed with HBSS. In the experiment allowing ligand recycling 250 μL of assay medium were added to the wells (n=3). In the experiment inhibiting ligand recycling, 225 μL of assay medium and 25 μL of a 1 mM solution of AMD3100 in HBSS were added to the wells (n=3). Subsequently, cells were incubated at 37° C. for 5, 15, 30 and 60 min, respectively. The supernatant was removed and combined with 250 μL of HBSS used for rinsing the cells. This fraction represents the amount of externalized ligand at the respective time point. The following lysis of the cells was performed as desribed for the internalization experiment.

In Vivo Animal Studies

Tumor Models

For the induction of tumor growth, female CB-17 SCID mice (6-8 weeks, Charles River, Sulzfeld, Germany) were injected subcutaneously with app. $5 \times 10^6$ Daudi (right shoulder) or SU-DHL-8 (left shoulder) cells suspended in 100 μL of a 1:1 (v/v) mixture of serum free culture medium and Matrigel (BD Biosciences, Heidelberg, Germany). Within 10-21 days, solid palpable tumors had grown (100-800 mg), and the animals were used for the experiments.

Dual Tracer Biodistribution Study

For the biodistribution study, approximately 5 MBq (135 μCD of yorn'(AMBS, DOTA, $^{68}$Ga)RNalG (1 nM) and 550 kBq (15 μCi) of [$^{125}$I]yorn'AMBS, DOTA, Ga)RNalG in a total volume of 100 μL of PBS (pH 7.4) were connected intravenously (i.v.) into the tail vein of Daudi- and SU-DHL-8-tumor bearing CB-17 SCID mice under isoflurane anaesthesia. The animals were sacrificed 90 min post injection (p.i.), and the organs of interest were dissected. The radioactivity was measured in weighted tissue samples using a γ-counter. Data are expressed in % ID/g tissue (mean±SD).

Results

Lipophilicities of selected compounds are summarized in table 2.

TABLE 2

Lipophilicities (log $P_{O/PBS}$) of [$^{125}$I]FC-131, [$^{68}$Ga]pentixafor and various radioiodinated analogs thereof with different metal complexes and linker-units

| Peptide | Log $P_{O/PBS}$ |
|---|---|
| [$^{125}$I]FC-131 | −0.35 |
| yorn'(AMBS, DOTA, $^{68}$Ga)RNalG | −2.90 |
| [$^{125}$I]yorn'(AMBS, DOTA, Ga)RNalG | −1.56 |
| [$^{125}$I]yorn'(AMBS, DOTA, Lu)RNalG | −1.38 |
| [$^{125}$I]yorn'(AMBS, DOTA, Bi)RNalG | — |
| [$^{125}$I]yorn'(AMBS, DOTA, In)RNalG | −1.39 |
| [$^{125}$I]yorn'(ABS, DOTA, In)RNalG | −1.37 |
| [$^{125}$I]yorn'(ABS, G, DOTA, In)RNalG | — |
| [$^{125}$I]yorn'(ABS, Ahx, DOTA, In)RNalG | — |
| [$^{125}$I]yorn'(ABS, DOTA, Lu)RNalG | — |
| [$^{125}$I]yorn'(ABS, G, DOTA, Lu)RNalG | −1.28 |
| [$^{125}$I]yorn'(ABS, Avs, DOTA, Lu)RNalG | −1.23 |
| [$^{125}$I]yorn'(ABS, Ahx, DOTA, Lu)RNalG | — |

(Radio)iodination of D-Tyr$^1$ leads to an increase in lipophilicity for [$^{125}$I]yorn'(AMBS, DOTA, Ga)RNalG compared to yorn'(AMBS, DOTA, $^{68}$Ga)RNalG. This effect is further enhanced by substitution of Ga by Lu or In, whose complex geometries, in contrast to Ga, require the involvement of all free carboxylate pendant arms of DOTA. This leads to the additional loss of a charged group in the molecule, resulting in enhanced lipophilicity, and will most certainly have certain influence on in vivo pharmacokinetics of the various (radio)iodinated compounds of invention.

TABLE 3

CXCR4 affinities (IC$_{50}$ in nM) of various metallated yorn'RNalG analogs to hCXCR4-expressing Jurkat T-cell leukemia cells. [$^{125}$I]FC-131 was used as radioligand. Each experiment was performed in triplicate, and results are means ± SD from three separate experiments.

| Peptide | IC$_{50}$ [nM] |
|---|---|
| yorn'(DOTA)RNalG | 807 ± 477 |
| yorn'(DOTA, Ga)RNalG | 288.9 |
| yorn'(DOTA, In)RNalG | >1000 |
| yorn'(ABS, DOTA)RNalG | 334.7 |
| yorn'(ABS, DOTA, In)RNalG | 105.2 |
| yorn'(ABS, DOTA, Ga)RNalG | 11.5 ± 4.4 |
| yorn'(ABS, Ahx, DOTA)RNalG | >1000 |
| yorn'(ABS, Ahx, DOTA, In)RNalG | 26.5 ± 22.6 |
| yorn'(ABS, Ahx, DOTA, Ga)RNalG | 30.3 ± 6.52 |
| yorn'(ABS, betaAla, DOTA)RNalG | 37.6 ± 14.7 |
| yorn'(ABS, betaAla, DOTA, Ga)RNalG | 33.3 ± 3.68 |
| yorn'(ABS, betaAla, DOTA, In)RNalG | 30.4 ± 3.68 |
| yorn'(ABS, AVS, DOTA)RNalG | 121 ± 17 |
| yorn'(ABS, AVS, DOTA, Ga)RNalG | 14.2 ± 3.01 |
| yorn'(ABS, AVS, DOTA, In)RNalG | 40.9 ± 21.6 |
| yorn'(ABS, G, DOTA)RNalG | 88.8 ± 18.4 |
| yorn'(ABS, G, DOTA, Ga)RNalG | 16.7 ± 3.28 |
| yorn'(ABS, G, DOTA, In)RNalG | 20.9 ± 3.46 |
| yorn'(AMBS, DOTA, Ga)RNalG | 5.0 ± 0.8 |
| yorn'(AMBS, DOTA, In)RNalG | 44.9 ± 10.4 |
| yorn'(AMBS, DOTA, Lu)RNalG | 50.4 ± 17.8 |
| yorn'(AMBS, DOTA, Bi)RNalG | 22.0 ± 7.0 |
| yorn'(AVS, AVS, DOTA)RNalG | >1000 |
| yorn'(AVS, AVS, DOTA, Ga)RNalG | 89.7 ± 18.3 |
| yorn'(AVS, AVS, DOTA, In)RNalG | 123.0 ± 25.02 |
| yorn'(G, Trigas, DOTA)RNalG | 903 ± 439 |
| yorn'(G, Trigas, DOTA, In)RNalG | 456.8 (n = 1) |

Obviously, the highly optimized structure of yorn' (AMBS, DOTA, Ga)RNalG precludes the use of its e.g. $^{177}$Lu- analog for CXCR4-targeted endoradiotherapy, since the exchange of the radiometal in the DOTA-chelator leads to different complex geometries and thus, since the complex itselfs seems to be involved in ligand binding, to a dramatic loss in binding affinity.

The IC$_{50}$ of 3-iodo-D-Tyr$^1$-FC-131 had been shown to be by a factor of four higher than that of yorn'(AMBS, DOTA, Ga)RNalG (1.3 vs 5 nM). When the CXCR4-affinities of [$^{125}$I]FC-131 and yorn'(AMBS, DOTA, $^{68}$Ga)RNalG were compared in an inverse IC$_{50}$ study (different radioligands assayed against a standard competitor; in this assay a higher IC$_{50,inv}$ reflects a higher receptor affinity), yorn'(AMBS, DOTA, $^{68}$Ga)RNalG showed an increase in receptor affinity compared to the reference by a factor of app.5. Thus, combining the results of these separate assays, (radio)iodination of yorn'(AMBS, DOTA, Ga)RNalG led to an increase in CXCR4 affinity by a factor of almost 20. [Schottelius M et al. oral presentation #495, Annual Meeting of the Am. Soc Nucl Med. 2014, St Louis, USA)].

To investigate, to what extent D-tyrosine$^1$ iodination might also improve CXCR4 affinity of these compounds (Table 4), various radioiodinated In- and Lu-yorn'RNalG analogs containing different spacers were assayed with respect to their CXCR4 affinity in an inverse IC$_{50}$ study using Jurkat cells and unlabeled FC131 as competitor. The inverse IC$_{50}$ data obtained for all these compounds are summarized in table 5.

TABLE 5

Inversely determined binding affinities (IC$_{50, inv}$ in nM) of the different radioiodinated CXCR4-ligands to hCXCR4-expressing Jurkat T-cell leukemia cells. FC-131 was used as the standard competitor. Each experiment was performed in triplicate, and results are means ± SD from three separate experiments. In this experiment, higher IC$_{50, inv}$ values indicate an increased hCXCR4-affinity.

| Peptide | IC$_{50, inv}$ [nM] |
|---|---|
| [$^{125}$I]FC-131 | 4.0 ± 1.2 |
| [$^{125}$I]yorn'(AMBS, DOTA, Ga)RNalG | 18.3 ± 6.6 |
| [$^{125}$I]yorn'(AMBS, DOTA, Lu)RNalG | 12.1 ± 2.6 |
| [$^{125}$I]yorn'(AMBS, DOTA, Bi)RNalG | 13.7 ± 2.4 |
| [$^{125}$I]yorn'(AMBS, DOTA, In)RNalG | 14.5 ± 0.6 |
| [$^{125}$I]yorn'(ABS, DOTA, In)RNalG | 21.2 ± 2.0 |
| [$^{125}$I]yorn'(ABS, G, DOTA, In)RNalG | 7.7 ± 0.6 |
| [$^{125}$I]yorn'(ABS, Ahx, DOTA, In)RNalG | 7.4 ± 1.1 |
| [$^{125}$I]yorn'(ABS, DOTA, Lu)RNalG | 25.0 ± 1.5 |
| [$^{125}$I]yorn'(ABS, G, DOTA, Lu)RNalG | 22.2 ± 1.6 |
| [$^{125}$I]yorn'(ABS, Avs, DOTA, Lu)RNalG | 13.1 ± 0.6 |
| [$^{125}$I]yorn'(ABS, Ahx, DOTA, Lu)RNalG | 14.4 ± 0.5 |

Surprisingly, all radioiodinated metalated CPCR4.2 analogs displayed high CXCR4 affinities in the inverse IC$_{50}$ studies, with comparably little effect of the spacer-chelate-moiety on affinity. While iodination of 131FC only lead to a fourfold improvement of CXCR4 affinity, radioiodination of metallated DOTA-analogs of CPCR4.2 resulted in a disproportionately strong increase in CXCR4 affinity, which is graphically shown in FIG. 1.

Obviously, introduction of an iodide atom at the D-tyrosine$^1$ residue of the peptide leads to increased ligand lipophilicity, which in turn seems to lead to substantially improved lig-and-receptor interaction via lipophilic interactions such as e.g. 7-7r-stacking with a Pheresidue of the receptor protein. However, the most interesting result of these studies is the substantial over-compensation of the influence of the spacer-chelate-part of the molecule on receptor affinity by this minimal structural modification. These findings open up entirely new perspectives for the development of therapeutic yorn'RNalG-based radiopharmaceuticals, since now the entire palette of diagnostic and therapeutic radiometals as well as labeling with the Al$^{18}$F$^{2+}$-ion is at hand.

Besides receptor affinity internalization plays an important role for efficient tracer accumulation and retention, which is particularly relevant for endoradiotherapy. Thus yorn'(AMBS, DOTA, $^{68}$Ga)RNalG and [$^{125}$I]yorn'(AMBS, DOTA, Ga)RNalG were comparatively evaluated as an exemplary pair of non-iodinated/iodinated (radio)metallated yorn'RNalG analogs with respect to internalization efficiency and intracellular retention.

Figure 2:
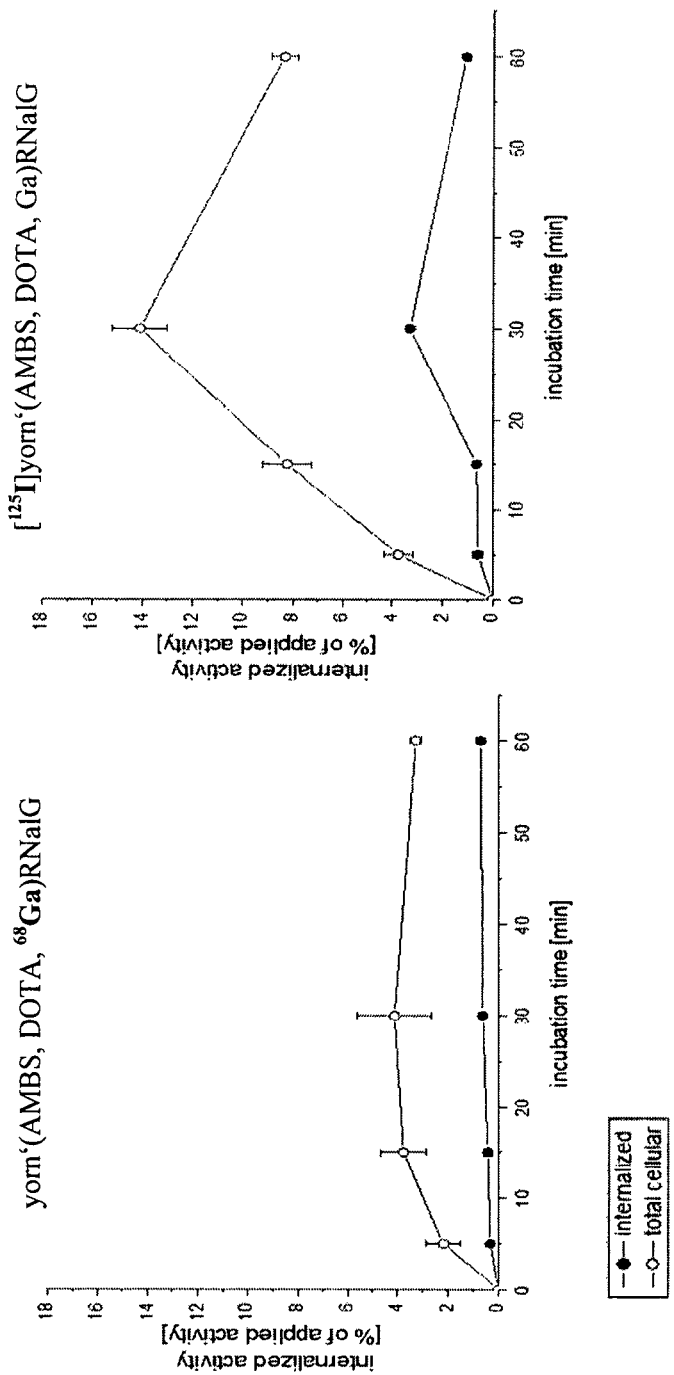
FIG. 2 Binding and internalization kinetics of yorn' (AMBS, DOTA, $^{68}$Ga)RNalG and [$^{125}$I]yorn'(AMBS, DOTA, Ga)RNalG in Jurkat cells. Data are corrected for non-specific binding in the presence of 100 μM AMD3100

To evaluate differences in internalization efficiency between yorn'(AMBS, DOTA, $^{68}$Ga)RNalG and [$^{125}$I]yorn' (AMBS, DOTA, Ga)RNalG, dual tracer internalization studies were performed in various human cancer cell lines, including Jurkat, Daudi and SUDHL-8 B-cell lymphoma cells as well as MCF-7 (breast), HT-29 (colon), SH—SY5Y (neuroblastoma) cell lines and the prostate carcinoma cell lines DU-145 and LNCaP. FIG. 2 shows exemplary kinetics for total cellular binding (membrane bound+internalized activity) and internalization of yorn'(AMBS, DOTA, $^{68}$Ga) RNalG and [$^{125}$I]yorn'(AMBS, DOTA, Ga)RNalG in Jurkat cells.

These data illustrate the anticipated fact—yorn'(AMBS, DOTA, $^{68}$Ga)RNalG and [$^{125}$I]yorn'(AMBS, DOTA, Ga)RNalG being CXCR4 antagonists—that the fraction of membrane bound activity is considerably higher than internalized activity for both ligands. Data were comparable for the other cell lines used in this study.

Figure 3A:
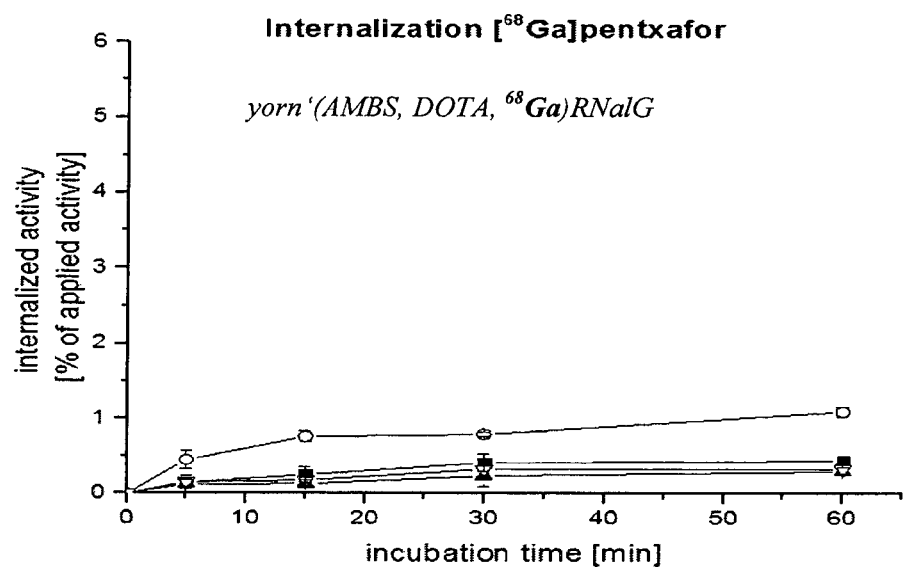
FIGS. 3a and b: Internalization kinetics of yorn'(AMBS, DOTA, $^{68}$Ga)RNalG and [$^{125}$I]yorn'(AMBS, DOTA, Ga)RNalG using SH—SY5Y, HT-29, MCF-7 and DU-145 cells. Data are corrected for non-specific binding in the presence of 100 μM AMD3100.
Figure 3B:
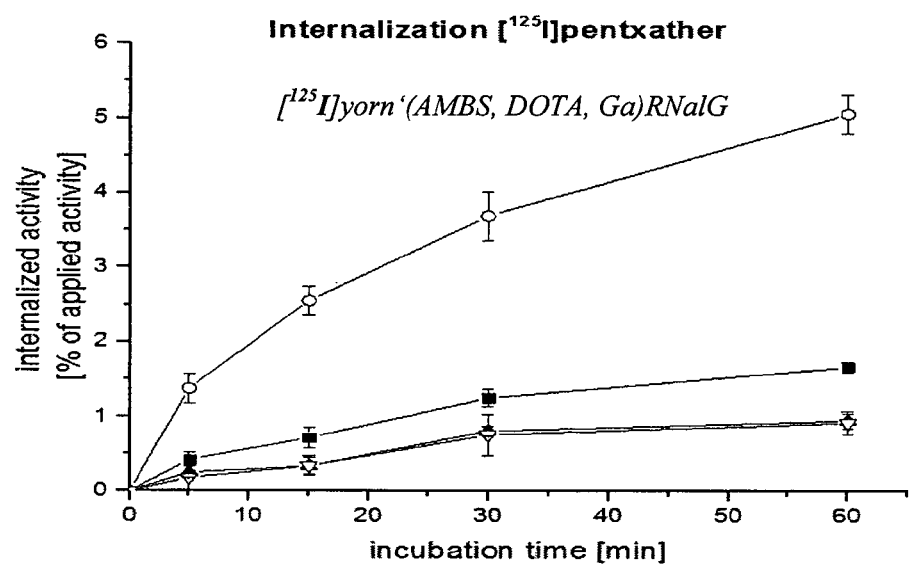

However, in all cell lines, [$^{125}$I]yorn'(AMBS, DOTA, Ga)RNalG showed significantly higher internalization than yorn'(AMBS, DOTA, $^{68}$Ga)RNalG (data for adherent cell lines are summarized in FIG. 3).

[$^{125}$I]yorn'(AMBS, DOTA, Ga)RNalG showed enhanced internalization efficiency (ratio of internalized to total cellular activity) compared to its non-iodinated counterpart, independently of the cell line used (table 6). Interestingly, the extent of absolute ligand internalization varies greatly between cell lines.

TABLE 6

Internalization efficiency of yorn'(AMBS, DOTA, $^{68}$Ga)RNalG and [$^{125}$I]yorn'(AMBS, DOTA, Ga)RNalG (30 min, 37° C.) using CXCR4 expressing cell lines. Data are corrected for non-specific binding in the presence of 100 μM AMD3100. Data represent internalized activity in % of total cellular activity.

| Cell linie | yorn'(AMBS, DOTA, $^{68}$Ga)RNalG | [$^{125}$I]yorn'(AMBS, DOTA, Ga)RNalG |
|---|---|---|
| Jurkat | 17.9 ± 4.0 | 27.4 ± 2.0 |
| Daudi | 29.2 ± 6.4 | 51.3 ± 4.4 |
| SUDHL-8 | 25.3 ± 7.9 | 29.9 ± 5.2 |
| HT-29 | 51.5 ± 9.3 | 77.9 ± 4.6 |
| SH-SY5Y | 33.8 ± 6.4 | 57.3 ± 7.1 |
| MCF-7 | 16.4 ± 5.2 | 37.6 ± 3.7 |
| DU-145 | 37.0 ± 7.5 | 69.1 ± 18.2 |

In summary, these data indicate an influence of ligand structure on internalization efficiency that is uncoupled from receptor affinity.

Figure 4A:
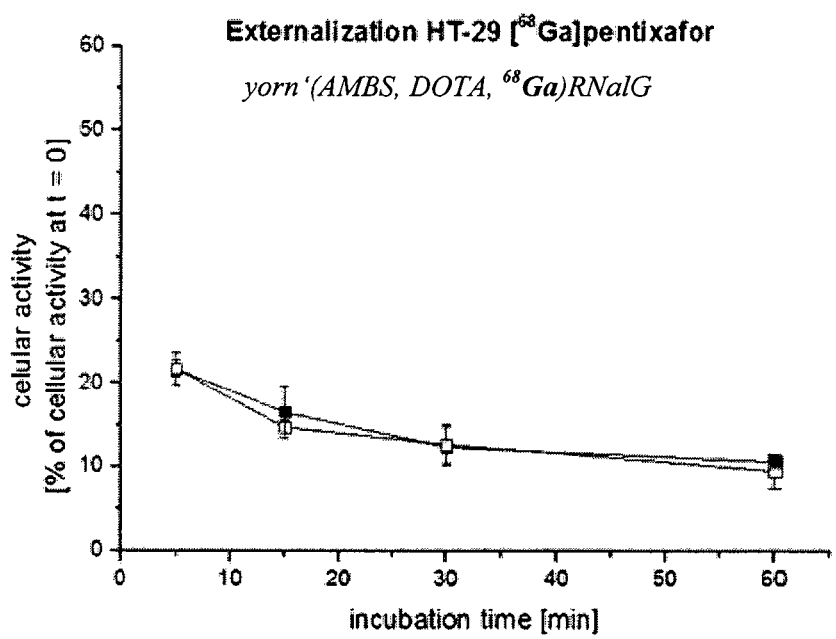
FIGS. 4a and b: Exemplary externalization kinetics of yorn'(AMBS, DOTA, $^{68}$Ga)RNalG and [$^{125}$I]yorn'(AMBS, DOTA, Ga)RNalG from HT-29 cells after a 30 min internalization incubation. The experiment was performed under conditions allowing ligand recycling (medium only) and inhibiting recycling (100 μM AMD3100). Data represent means ±SD (n=3).
Figure 4B:
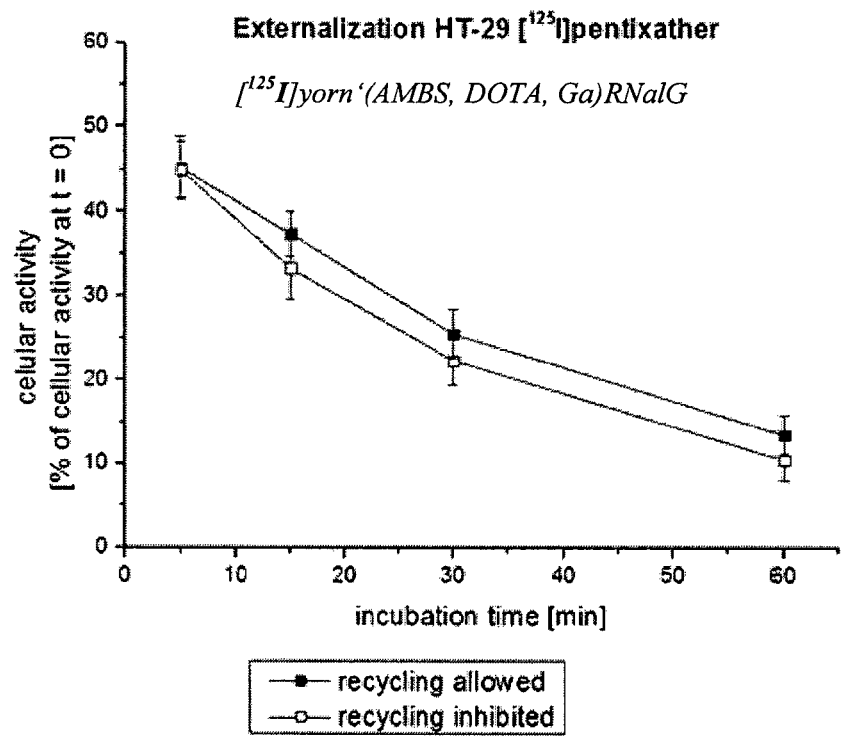

Given the importance of intracellular activity retention especially in an endoradiotherapeutic setting, exemplary comparative externalization kinetics of yorn'MBS, DOTA, $^{68}$Ga)RNalG and [$^{125}$I]yorn'(AMBS, DOTA, Ga)RNalG were also performed. Ligand release from HT-29 cells under conditions allowing and inhibiting ligand recycling are shown in FIG. 4.

It is important to mention, that the seemingly fast washout of cellular activity within the first five minutes is due to dissociation of membrane bound activity, which had not been removed by an acidic wash step previous to the externalization incubation to preserve receptor integrity. Thus, "true" externalization of internalized ligand only starts at app. t=5. Despite significantly enhanced internalization efficiency of [$^{125}$I]yorn'(AMBS, DOTA, Ga)RNalG, almost no ligand recycling was observed for both radioligands. Nearly identical results were obtained for the other cell lines used in this study. This finding is further illustrated in table 7, showing the remaining internalized activity for both radioligands under conditions allowing and inhibiting recycling in % of the total cellular activity at t=0 in different cell lines. As mentioned, ligand recycling does not contribute to cellular tracer retention, neither for yorn'(AMBS, DOTA, $^{68}$Ga)RNalG nor for [$^{125}$I]yorn'(AMBS, DOTA, Ga)RNalG.

TABLE 7

Residual internalized activity of yorn'(AMBS, DOTA, $^{68}$Ga)RNalG and [$^{125}$I]yorn'(AMBS, DOTA, Ga)RNalG in different CXCR4 expressing cell lines after a 60 min externalization incubation [% of total cellular activity at t = 0] under conditions allowing (medium only) or inhibiting (100 μM AMD3100 in external medium) ligand recycling. Data represent means ± SD (n = 3).

| | yorn'(AMBS, DOTA, $^{68}$Ga)RNalG | | [$^{125}$I]yorn'(AMBS, DOTA, Ga)RNalG | |
|---|---|---|---|---|
| | Recycling | | | |
| Cell linie | allowed | inhibited | allowed | inhibited |
| Jurkat | 6.8 ± 2.7 | 3.6 ± 0.3 | 8.0 ± 2.0 | 3.7 ± 1.3 |
| Daudi | 7.8 ± 1.6 | 5.2 ± 1.2 | 14.5 ± 2.0 | 7.0 ± 0.5 |
| HT-29 | 10.6 ± 0.8 | 9.5 ± 2.0 | 13.5 ± 2.6 | 10.5 ± 2.5 |
| SH-SY5Y | 10.9 ± 0.3 | 8.3 ± 1.5 | 11.2 ± 2.5 | 7.8 ± 1.0 |
| MCF-7 | 6.5 ± 2.0 | 8.7 ± 2.5 | 10.4 ± 1.4 | 8.7 ± 1.1 |

Figure 5:
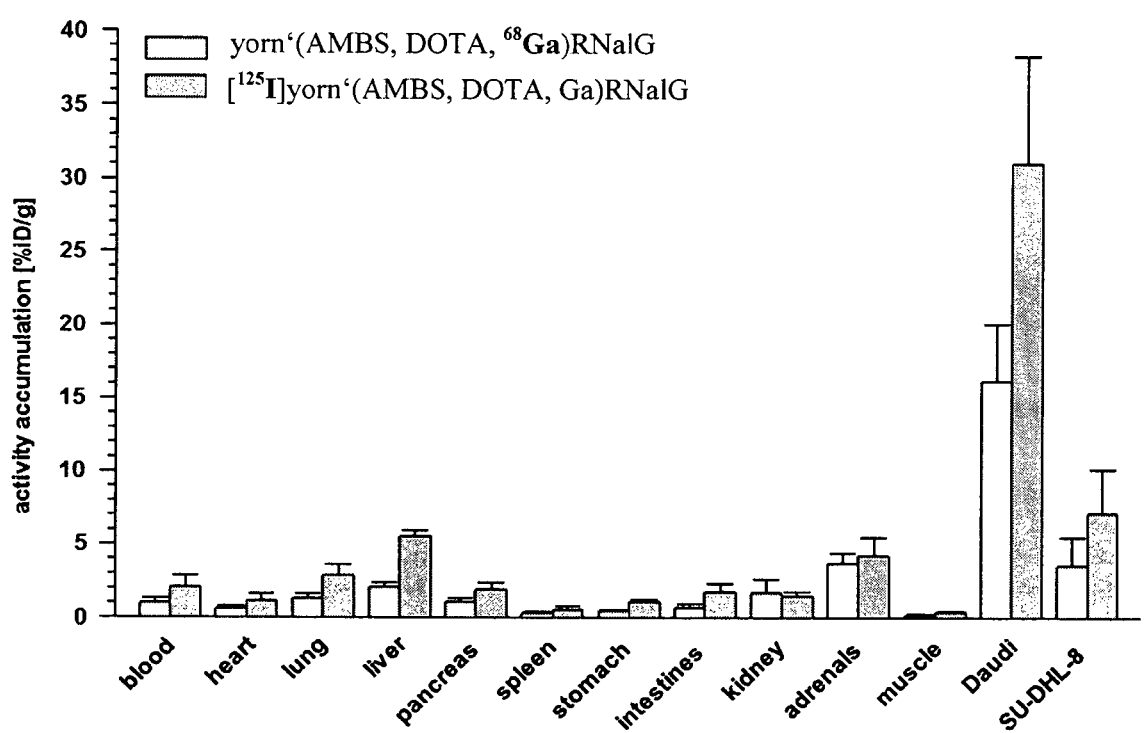
FIG. 5: Biodistribution of yorn'(AMBS, DOTA, $^{68}$Ga)RNalG and [$^{125}$I]yorn'(AMBS, DOTA, Ga)RNalG in Daudi (high CXCR4) and SU-DHL-8 (low CXCR4) lymphoma bearing SCID mice 60 min p.i., Data are given in % injected dose per gram tissue [% iD/g] and represent means +SD (n=5).

Based on the substantially improved in vitro targeting characteristics of [$^{125}$I]yorn'(AMBS, DOTA, Ga)RNalG compared to yorn'(AMBS, DOTA, $^{68}$Ga)RNalG, both compounds were also compared with respect to their in vivo pharmacokinetics. Both compounds were coinjected into Daudi (high CXCR4) and SU-DHL-8 (low CXCR4) xenograft bearing SCID mice (dual tracer study), and ligand biodistribution at 1 h p.i. was investigated in a first study. Data are summarized in FIG. 5.

As expected, [$^{125}$I]yorn'(AMBS, DOTA, Ga)RNalG shows substantially higher tumor uptake compared to yorn' (AMBS, DOTA, $^{68}$Ga)Na1G, both in Daudi and in SU-DHL-8 tumors, reflecting its increased CXCR4 affinity. However, due to the enhanced lipophilicity of [$^{125}$I]yorn' (AMBS, DOTA, Ga)RNalG, blood clearance of the tracer is slightly delayed, and non-specific uptake especially in the excretion organs (except kidney) is also increased. This leads despite the clearly superior CXCR4-targeting efficiency of [$^{125}$I]yorn'(AMBS, DOTA, Ga)RNalG to comparable tumor-to-non-tumor ratios for both compounds investigated. ⁻ ions of MIF in atherosclerosis, J. Mol. Med (2008), 86, 761-770.

Shah K, Weissleder R. (2005) Molecular optical imaging: applications leading to the development of present day therapeutics. NeuroRx.;2(2):215-25.

Taniuchi S, Masuda M, Fujii Y, Izawa K, Kanegane H, Kobayashi Y (2005) The role of a mutation of the CXCR4 gene in WHIM syndrome. Haematologica; 90(9):1271-2.

Van der Plas, S. E.; Gea, A.; Figaroli, S.; De Clercq, P. J. (2008) Madder, A. Synthesis of a tripodal scaffold for solid phase synthesis of artificial receptors. European Journal of Organic Chemistry, 1582-1588.

Weissleder R, Ntziachristos V (2003) Shedding light onto live molecular targets. Nat Med.; 9(1):123-8.

Weissleder R, Pittet M J (2008) Imaging in the era of molecular oncology, Nature; 452(7187):580-9.

Yang, P. Y.; Wu, H.; Lee, M. Y.; Xu, A. (2008) Srinivasan, R. et al. Solid-phase synthesis of azidomethylene inhibitors targeting cysteine proteases. Organic Letters, 10, 1881-1884.

Zhang et al., Inorg. Chem. 37(5), 1998, 956-963.

WO 89/07456
WO 97/31657
WO 2007/096662
WO 2008/08854
WO 2009/027706
WO 2009/109332

The invention claimed is:
1. A compound having a structure according to formula I

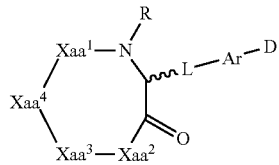
(I)

or a pharmaceutically acceptable salt thereof,
wherein Xaa$^1$ is selected from the group consisting of iodo-substituted D-Tyr; iodo-substituted L-Tyr; D-Tyr, which is methyl-substituted at the aromatic ring; L-Tyr, which is methyl-substituted at the aromatic ring; iodo-substituted or methyl-substituted D-homotyrosine; iodo-substituted or methyl-substituted L- homotyrosine; iodo-substituted or methyl-substituted D-Phe; iodo-substituted or methyl-substituted L-Phe iodo-substituted or methyl-substituted D-p-OH-phenylglycine; iodo-substituted or methyl-substituted p-OH-phenylglycine; iodo-substituted or methyl-substituted D-Trp; and iodo-substituted or methyl-substituted L-Trp;
Xaa$^2$ is arginine (Arg),
Xaa$^3$ is naphthylalanine (Nal),
Xaa$^4$ is glycine,
R is H or methyl,
L is a linker moiety selected from,

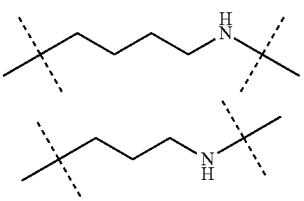

Ar is selected from the group consisting of
ABS-Avs: N-(5-aminoveratryl)-4-aminobenzoyl
ABS-Ahx: N-(5-aminohexanyl)-4-aminobenzoyl
AMBS-Gly: N-(glycinyl)-4-aminomethylbenzoyl
AMBS-Avs: N-(5-aminoveratryl)-4-aminomethylbenzoyl
AMBS: 4-aminomethylbenzoyl
wherein the free amino group of Ar is linked to D and the free acyl function of Ar is linked to L
and
D is
i) an organic complexation agent selected from NODASA, NODAGA, TETA, TRITA, TRAP, DTPA, CHX-DTPA EDTA, CDTA, CPTA, DOTP, DOTPI, EGTA, HBED, DTPA, DOT A, DOTAGA, NOTA, HP-DOA3, CBTE2a, TE2A, TMT, DPDP, HYNIC, DFO, HEDTA, NOPO, MAG3, NCS-MP-NODA, NH2-MPAA-NODA, and NODA;
ii) a nuclide or radionuclide selected from $^{11}$C, $^{18}$F, $^{47}$Sc, $^{51}$Cr, $^{52m}$Mn, $^{58}$Co, $^{52}$Fe, $^{56}$Ni, $^{57}$Ni, $^{62}$Cy, $^{64}$Cu, $^{67}$Cu, $^{66}$Ga, $^{68}$Ga, $^{67}$Ga $^{72}$As, $^{77}$As, $^{75}$Br, $^{76}$Br, $^{77}$Br, $^{82}$Br, $^{89}$Zr, $^{90}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{120}$I, $^{123}$I, $^{124}$I, $^{125}$I, $^{127}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{nat}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi and $^{225}$Ac and radioactive ion Al$^{18}$F$^{2+}$;
iii) a combination of a nuclide or radionuclide of ii) and a complexation agent of i), with the complexation agent being covalently bound to Ar;
iv) detectable label;
v) a combination of a detectable label and a nuclide or radionuclide of ii) or a complexation agent of i); or
vi) an active substance selected from cytotoxic agents, lipids, sugars, sugar conjugates, proteins and combinations thereof.

2. The compound of claim 1, wherein the compound is (3iodo)yorn'(AMBS, DOTA)RNalG:

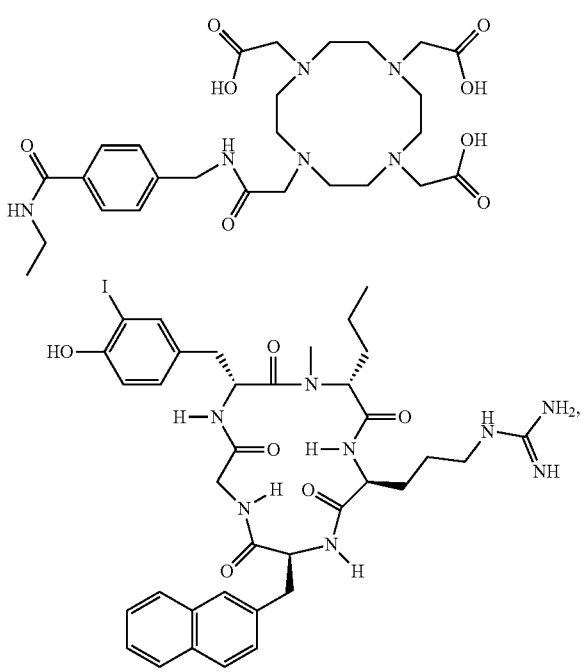

which is optionally complexed with a nuclide or radionuclide.

3. The compound of claim 1, wherein Xaa$^1$ is an iodo-substituted D- or L-tyrosine amino acid or an iodo-substituted D- or L-homotyrosine amino acid;

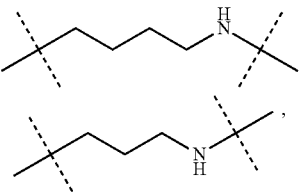

As is

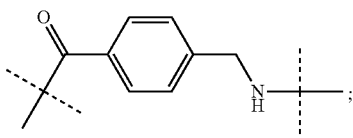

wherein D is a combination of a radionuclide and a complexation agent, with the complexation agent being covalently bound to Ar, wherein i) the complexation agent is selected from NODASA, NODAGA, TETA, TRITA, TRAP, DTPA, CHX-DTPA EDTA, CDTA, CPTA, DOTP, DOTPI, EGTA, HBED, TTHA, DTPA, DOTA, DOTAGA, NOTA, HP-DOA3, CBTE2a, TE2A, TMT, DPDP, HYNIC, DFO, HEDTA NOPO, MAG3, NCS-MP-NODA, NH2-MPAA-NODA and NODA; and ii) the nuclide or radionuclide is selected from $^{18}$F, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{72}$As, $^{77}$As, $^{75}$Br, $^{76}$Br, $^{77}$Br, $^{82}$Br, $^{89}$Zr, $^{90}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{120}$I, $^{123}$I, $^{124}$I, $^{125}$I, $^{127}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{nat}$Lu, $^{186}$Re, $^{188}$Re, $^{191}$Pt, $^{197}$Hg, $^{198}$Au, $^{199}$Au, $^{201}$Tl, $^{203}$Tb, $^{211}$At, $^{212}$Bi and $^{212}$Bi and $^{225}$Ac and radioactive ion Al$^{18}$F$^{2+}$.

4. The compound of claim 3, wherein Xaa$^1$ is the 3-iodinated D- or L-tyrosine amino acid or the 3-iodinated D- or L-homotyrosine amino acid.

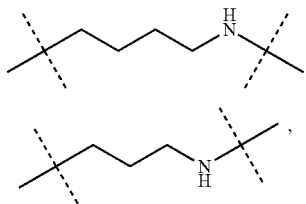

5. The compound of claim 3, wherein the tyrosine or homotyrosine is substituted with $^{127}$I.

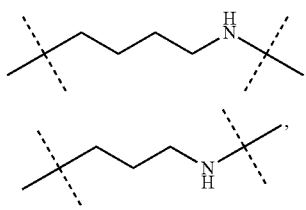

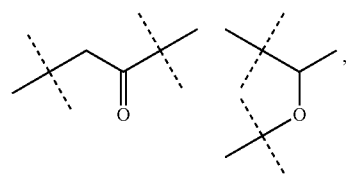

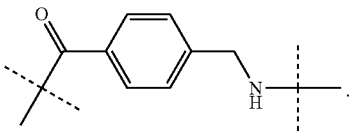

6. A pharmaceutical composition comprising a compound of claim 1 and at least one pharmaceutically acceptable excipient.

7. A pharmaceutical composition comprising a compound of claim 3 and at least one pharmaceutically acceptable excipient.

8. A method of treating CXCR4 receptor-related disease or disorder which comprises administering to a patient in need thereof an effective amount of a compound of claim 3, wherein the CXCR4 receptor-related disease or disorder is selected from multiple sclerosis (MS), lupus erythematosus, Sjogren's syndrome, ulcerative colitis, rheumatoid arthritis, atherosclerosis, hypertonic diseases, thrombosis, ischemic heart disease, myocardial infarction, vasculitis, asthma coronary heart disease (CHD), Alzheimer's disease, Stroke, HIV infection, leukaemia, kaemia, chronic lymphocytic B-cell leukaemia (B-CLL), lymphomas, myelomas, pain, sarcomas, melanomas, blastomas, lymphomas cancer metastases, astrocytoma, lymphoma, breast adenocarcinoma, breast carcinoma, cervical adenocarcinoma, colon adenocarcinoma, colorectal adenocarcinoma, colorectal carcinoma, glioblastoma, hepatocellular carcinoma, hepatoma and pancreatic carcinoma, leukaemia, large cell lung cancer, lung adenocarcinoma, lung carcinoma, lung mesothelioma, lung squamous cell carcinoma, melanoma, neuroblastoma, non-small cell and small cell lung cancer (NSCLC and SCLC), ovarian cancer, pancreatic adenocarcinoma, pancreatic carcinoma, prostate adenocarcinoma, prostate carcinoma, rectal adenocarcinoma, renal cell adenocarcinoma cinoma, adrenal carcinoma, Burkitt's B-cell lymphoma, cervical adenocarcinomas, oesophageal cancer, gliomas, glioblastomas, hepatocellular carcinomas (malignant hepatomas), hepatomas, mamma-carcinomas, nasopharyngeal adenocarcinoma, T-cell lymphoma, and thyroid cancer.

9. A method of imaging CXCR4 receptors and CXCR4 receptor related diseases or disorders, which comprises administering to a subject the compound of claim 3, wherein the compound comprises a radioactive or detectable label, and detecting said compound in association with CXCR4 receptors and imaging the CXCR4 receptors in association with said disease or disorder,
wherein the CXCR4 receptor-related disease or disorder is selected from multiple sclerosis (MS), lupus erythematosus, Sjogren's syndrome, ulcerative colitis, rheumatoid arthritis, atherosclerosis, hypertonic diseases, thrombosis, ischemic heart disease, myocardial infarction, vasculitis, asthma coronary heart disease (CHD), Alzheimer's disease, Stroke, HIV infection, leukaemia, kaemia, chronic lymphocytic B-cell leukaemia (B-CLL), lymphomas, myelomas, pain, sarcomas, melanomas, blastomas, lymphomas cancer metastases, astrocytoma, lymphoma, breast adenocarcinoma, breast carcinoma, cervical adenocarcinoma, colon adenocarcinoma, colorectal adenocarcinoma, colorectal carcinoma, glioblastoma, hepatocellular carcinoma, hepatoma and pancreatic carcinoma, leukaemia, large cell lung cancer, lung adenocarcinoma, lung carcinoma, lung mesothelioma, lung squamous cell carcinoma, melanoma, neuroblastoma, non-small cell and small cell lung cancer (NSCLC and SCLC), ovarian cancer, pancreatic adenocarcinoma, pancreatic carcinoma, prostate adenocarcinoma, prostate carcinoma, rectal adenocarcinoma, renal cell adenocarcinoma cinoma, adrenal carcinoma, Burkitt's B-cell lymphoma, cervical adenocarcinomas, oesophageal cancer, gliomas, glioblastomas, hepatocellular carcinomas (malignant hepatomas), hepatomas, mamma-carcinomas, nasopharyngeal adenocarcinoma, T-cell lymphoma, and thyroid cancer.

10. A method of peptide receptor radionuclide therapy or radioguided surgery, the method comprising administering a compound of claim 3 to a sample or a subject, wherein the compound comprises a radioactive or detectable label, and performing radionuclide therapy or radioguided surgery based on the location of the compound,
wherein the CXCR4 receptor-related disease or disorder is selected from multiple sclerosis (MS), lupus erythematosus, Sjogren's syndrome, ulcerative colitis, rheumatoid arthritis, atherosclerosis, hypertonic diseases, thrombosis, ischemic heart disease, myocardial infarction, vasculitis, asthma coronary heart disease (CHD), Alzheimer's disease, Stroke, HIV infection, leukaemia, kaemia, chronic lymphocytic B-cell leukaemia (B-CLL), lymphomas, myelomas, pain, sarcomas, melanomas, blastomas, lymphomas cancer metastases, astrocytoma, B-cell lymphoma, breast adenocarcinoma, breast carcinoma, cervical adenocarcinoma, colon adenocarcinoma, colorectal adenocarcinoma, colorectal carcinoma, glioblastoma, hepatocellular carcinoma, hepatoma and pancreatic carcinoma, leukaemia, large cell lung cancer, lung adenocarcinoma, lung carcinoma, lung mesothelioma, lung squamous cell carcinoma, melanoma, neuroblastoma, non-small cell and small cell lung cancer (NSCLC and SCLC), ovarian cancer, pancreatic adenocarcinoma, pancreatic carcinoma, prostate adenocarcinoma, prostate carcinoma, rectal adenocarcinoma, renal cell adenocarcinoma cinoma, adrenal carcinoma, Burkitt's B-cell lymphoma, cervical adenocarcinomas, oesophageal cancer, gliomas, glioblastomas, hepatocellular carcinomas (malignant hepatomas), hepatomas, mamma-carcinomas, nasopharyngeal adenocarcinoma, lymphoma, and thyroid cancer.

11. A method of diagnosing CXCR4 receptor-related disease or disorder which comprises administering to a patient in need thereof a compound as of claim 3, imaging the CXCR4 receptors, comparing CXCR4 receptor imaging data with standard values, correlating said comparison to the CXCR4 receptor-related disease or disorder,
wherein the CXCR4 receptor-related disease or disorder is selected from multiple sclerosis (MS), lupus erythematosus, Sjogren's syndrome, ulcerative colitis, rheumatoid arthritis, atherosclerosis, hypertonic diseases, thrombosis, ischemic heart disease, myocardial infarction, vasculitis, asthma coronary heart, disease (CHD), Alzheimer's disease, Stroke, HIV infection, leukaemia, kaemia, chronic lymphocytic B-cell leukaemia (B-CLL), lymphomas, myelomas, pain, sarcomas, melanomas, blastomas, lymphomas cancer metastases, astrocytoma, B-cell lymphoma, breast adenocarcinoma, breast carcinoma, cervical adenocarcinoma, colon adenocarcinoma, colorectal adenocarcinoma, colorectal carcinoma, glioblastoma, hepatocellular carcinoma, hepatoma and pancreatic carcinoma, leukaemia, large cell lung cancer, lung adenocarcinoma, lung carcinoma, lung mesothelioma, lung squamous cell carcinoma, melanoma;
neuroblastoma, non-small cell and small cell lung cancer (NSCLC and SCLC), ovarian cancer, pancreatic adenocarcinoma, pancreatic carcinoma, prostate adenocarcinoma, prostate carcinoma, rectal adenocarcinoma, renal cell adenocarcinoma cinoma, adrenal carcinoma, Burkitt's B-cell lymphoma, cervical adenocarcinomas, oesophageal cancer, gliomas, glioblastomas, hepatocellular carcinomas (malignant hepatomas), hepatomas, mamma-carcinomas, nasopharyngeal adenocarcinoma, I-cell lymphoma, and thyroid cancer.

* * * * *

UNITED STATES PATENT AND TRADEMARK OFFICE
CERTIFICATE OF CORRECTION

PATENT NO. : 10,919,938 B2
APPLICATION NO. : 15/315290
DATED : February 16, 2021
INVENTOR(S) : Hans-Jürgen Wester et al.

It is certified that error appears in the above-identified patent and that said Letters Patent is hereby corrected as shown below:

In the Specification

Column 5, Line 24:
Change "($3^{125}$iodo-y)" to -- (3-iodo-y) --

Column 5, Line 29:
Change "DO-TA" to -- DOTA --

Column 5, Lines 29 to 30:
Change "($^{125}$iodo-y)-or-tAAMBS," to -- ($^{125}$iodo-y)-orn´ (AMBS, --

Column 5, Line 30:
Change "($^{131}$iodoy)" to -- ($^{131}$iodo-y) --

Column 5, Line 34:
Change "-orni(AMBS" to -- -orn´(AMBS --

Column 6, Line 55:
Change "186Re, 188$_{Re}$, 191Pt," to -- $^{186}$Re, $^{188}$Re, $^{191}$Pt, --

Column 9, Line 3:
Change "$_{153}$Sm" to -- $^{153}$Sm --

Column 9, Line 4:
Change "$_{-188}$Re" to -- $^{188}$Re --

Column 9, Line 5:
Change "$_{212}$Bi" to -- $^{212}$Bi --

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)

Column 9, Line 7:
Change "64Cu" to -- $^{64}$Cu --

Column 10, Line 25:
Change "77Br" to -- $^{77}$Br --

Column 11, Line 48:
Change "77Br" to -- $^{77}$Br --

Column 18, Line 62:
Change "The terra unnatural basic amino acid" to -- The term unnatural basic amino acid --

Column 31, Line 65:
Change "DOT-PI" to -- DOTPI --

Column 32, Line 7:
Change "-$_{188}$Re" to -- $^{188}$Re --

Column 32, Line 48:
Change "$_{188}$Re" to -- $^{188}$Re --

Column 33, Line 37:
Change "$_{47}$Sc" to -- $^{47}$Sc --

Column 33, Line 38:
Change "$_{67}$Cu [ ] $_{72}$As" to -- $^{67}$CU [ ] $^{72}$As --

Column 33, Line 39:
Change "$_{82Br}$" to -- $^{82}$Br --

Column 33, Line 42:
Change "$_{166}$Ho" to -- $^{166}$Ho --

Column 33, Line 44:
Change "$_{203}$Pb" to -- $^{203}$Pb --

Column 35, Line 4:
Change "N$_t$S$_{(4-t)}$" to -- N$_t$S$_{(4-t)}$ --

Column 40, Line 67:
Change "folinula (22)" to -- formula (22) --

Column 55, Line 16:
Change "□ scale" to -- δ scale --

CERTIFICATE OF CORRECTION (continued)
U.S. Pat. No. 10,919,938 B2

Page 3 of 3

Column 75, Line 56:
Change "☐ Mercaptoethanol" to -- β mercaptoethanol --

Column 76, Line 8:
Change "IC$_{so}$" to -- IC$_{50}$ --

In the Claims

Column 84, Lines 15 through 41, in Claim 2:

Replace " 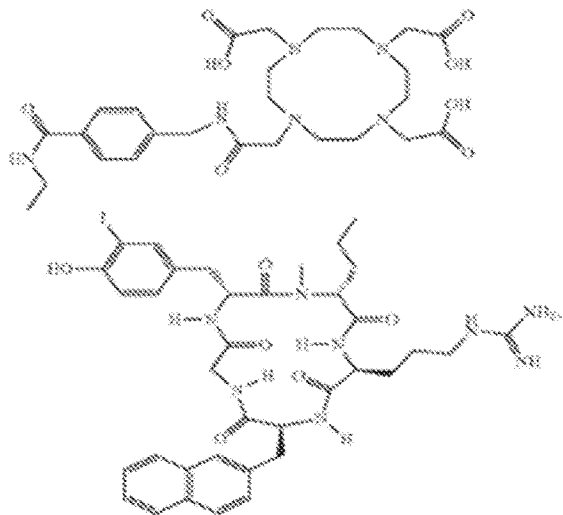 " with

" 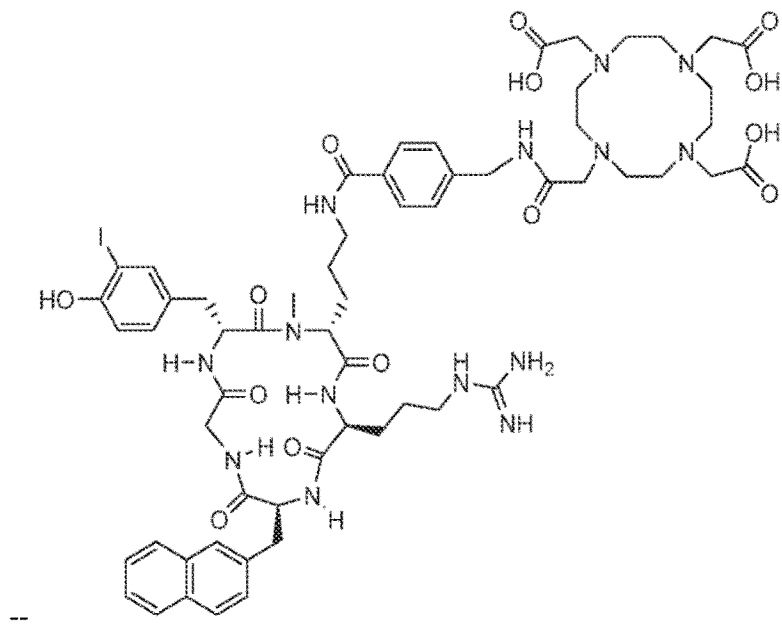 " --